(12) United States Patent
den Hartog et al.

(10) Patent No.: US 8,669,352 B2
(45) Date of Patent: Mar. 11, 2014

(54) ANTAGONISTIC ANTI-HUMAN CD40 MONOCLONAL ANTIBODY

(75) Inventors: Marcel Theodorus den Hartog, Monnickendam (NL); Ruprecht Jules Joost van Neerven, Almere (NL); Kevin Stuart Johnson, Herts (GB); Robert Duncan Casson, Herts (GB)

(73) Assignee: Fast Forward Pharmaceuticals B.V., Utrecht (NL)

( * ) Notice: Subject to any disclaimer, the term of this patent is extended or adjusted under 35 U.S.C. 154(b) by 809 days.

(21) Appl. No.: 11/801,344

(22) Filed: May 9, 2007

(65) Prior Publication Data

US 2008/0085531 A1 Apr. 10, 2008

Related U.S. Application Data

(60) Provisional application No. 60/798,819, filed on May 9, 2006.

(30) Foreign Application Priority Data

May 9, 2006 (EP) ..................................... 06076028

(51) Int. Cl.
*C07K 16/28* (2006.01)
(52) U.S. Cl.
USPC ................ 530/388.73; 530/387.1; 530/387.3; 530/388.1; 530/388.2; 530/388.22; 530/388.7
(58) Field of Classification Search
None
See application file for complete search history.

(56) References Cited

U.S. PATENT DOCUMENTS

| | | | |
|---|---|---|---|
| 6,413,514 | B1 | 7/2002 | Aruffo et al. |
| 7,288,251 | B2 | 10/2007 | Bedian et al. |
| 7,563,443 | B2 | 7/2009 | Grant et al. |

FOREIGN PATENT DOCUMENTS

| | | |
|---|---|---|
| EP | 0945465 A1 | 9/1999 |
| WO | WO93/010817 A1 | 6/1993 |
| WO | WO9731025 A1 | 8/1997 |
| WO | WO9803670 A1 | 1/1998 |
| WO | WO98/052976 A1 | 11/1998 |
| WO | WO9942075 A2 | 8/1999 |

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Roque-Navarro, L. et al., "Humanization of predicted T-cell epitopes reduces the immunogenicity of chimeric antibodies: New evidence supporting a simple method" Hybridoma and Hybridomics (2003), vol. 22(4), pp. 245-257 (see whole document).
Ranheim, E A, et al., "Activated T cells induce expression of B7/BB1 on normal or leukemic B cells through a CD40-dependent signal", J Exp Med (1993); 177: 925-35.
Hasbold, J. et al, "Properties of mouse CD40: cellular distribution of CD40 and B cell activation by monoclonal anti-mouse CD40 antibodies", Eur J Immunol (1994); 24: 1835-42.
Alderson, M R, et al., "CD40 expression by monocytes: regulation by cytokines and activation of monocytes by the ligand for CD40", J Exp Med (1993); 178: 669-74.
Kiener, P A, et al., "Stimulation of CD40 with purified soluble gp39 induces proinflammatory responses in human monocytes", J Immunol (1995); 155: 4917-25.
Shu U, et al., "Activated T cells induce interleukin-12 production by monocytes via CD40-CD40 ligand interaction", Eur J Immunol (1995); 25: 1125-8.
Cella M, et al., "Ligation of CD40 on dendritic cells triggers production of high levels of interleukin-12 and enhances T cell stimulatory capacity: T-T help via APC activation", J Exp Med (1996); 184: 747-52.
Van Kooten, C. et al., "Functions of CD40 on B cells, dendritic cells and other cells", Curr Opin Immunol (1997); 9: 330-7.
Cayabyab, M., et al., "CD40 preferentially costimulates activation of CD4+ T lymphocytes", J Immunol (1994); 152: 1523-31.
Hermann P, et al., "CD40 ligand-positive CD8+ T cell clones allow B cell growth and differentiation", Eur J Immunol (1995); 25: 2972-7.
Grewal, I. S., et al., "CD40 and CD154 in cell-mediated immunity", Annu Rev Immunol (1998); 16: 111-35.
Henn, V. et al., "CD40 ligand on activated platelets triggers an inflammatory reaction of endothelial cells", Nature (1998); 391: 591-4.
Clegg, C. H., et al., "Thymus dysfunction and chronic inflammatory disease in gp39 transgenic mice", Int Immunol (1997); 9: 1111-22.
Stuber, E., et al., "Blocking the CD40L-CD40 interaction in vivo specifically prevents the priming of T helper 1 cells through the inhibition of interleukin 12 secretion", J Exp Med (1996); 183: 693-8.
Liu, Z., et al., "Prevention of experimental colitis in SCID mice reconstituted with CD45RBhigh CD4+ T cells by blocking the CD40-CD154 interactions", J Immunol (2000); 164: 6005-14.
De Jong, Y. P., et al., "Chronic murine colitis is dependent on the CD154/CD40 pathway and can be attenuated by anti-CD154 administration", Gastroenterology (2000); 119: 715-23.
Kawai, T. et al., "Thromboembolic complications after treatment with monoclonal antibody against CD40 ligand", Nat Med (2000); 6: 114.
Buhler, L., et al., "Anti-CD154 monoclonal antibody and thromboembolism", Transplantation (2001); 71: 491.
Knossalla, C., et al, "Anti-CD154 monoclonal antibody and thromboembolism revisited", Transplantation (2002); 74: 416-17.
De Boer, M., et al., "Generation of monoclonal antibodies to human lymphocyte cell surface antigens using insect cells expressing recombinant proteins", J Immunol Meth (1992); 152: 15-23.
Kwekkeboom, J., et al., "CD40 plays an essential role in the activation of human B cells by murine EL4B5 cells", Immunology (1993); 79: 439-44.

(Continued)

*Primary Examiner* — Phillip Gambel
(74) *Attorney, Agent, or Firm* — Hoffmann & Baron, LLP

(57) ABSTRACT

The present invention provides novel antagonistic anti-human CD40 monoclonal antibodies, methods for generating them and uses thereof.

38 Claims, 22 Drawing Sheets

(56) References Cited

OTHER PUBLICATIONS

Kwekkeboom, J., et al., "Helper effector function of human T cells stimulated by anti-CD3 Mab can be enhanced by co-stimulatory signals and is partially dependent on CD40-CD40 ligand interaction", Eur J Immunol (1994); 24: 508-17.

Laman, J.D., et al., "Protection of marmoset monkeys against EAE by treatment with a murine antibody blocking CD40 (mu5D12)", Eur J Immunol (2002); 32: 2218-28.

Boon, L., et al., "Prevention of experimental autoimmune encephalomyelitis in the common marmoset (*Callithrix jacchus*) using a chimeric antagonist Mab against human CD40 is associated with altered B-cell responses", J Immunol (2001); 167: 2942-9.

Haanstra, K. G., et al., "Prevention of kidney allograft rejection using anti-CD40 and anti-CD86 in primates", Transplation (2003); 75: 637-43.

Haegel-Kronenberger, H., et al., "Inhibition of costimulation allows for repeated systemic administration of adenoviral vector in rhesus monkeys", Gene Ther (2004); 11: 241-52.

Boon, L., et al., "Preclinical assessment of anti-CD40 Mab 5D12 in cynomolgus monkeys", Toxicology (2002); 174: 53-65.

Sartor, R B., "Pathogenesis and immune mechanisms of chronic inflammatory bowel disease", Am J Gastroenterol (1997); 92: 5S-11S.

Fiocchi, C., "Inflammatory bowel disease: etiology and pathogenesis", Gastroenterology (1998); 15: 182-205.

Burgio, V. L., et al., "Peripheral monocyte and naive T-cell recruitment and activation in Crohn's disease", Gastroenterology (1995); 109: 1029-38.

Rugtveit, J., et al., "Increased macrophage subset in inflammatory bowel disease: apparent recruitment from peripheral blood monocytes", Gut (1994); 35: 669-74.

Fuss, I. J., "Disparate CD4+ lamina propria (LP) lymphokine secretion profiles in inflammatory bowel disease", J Immunol (1996); 157: 1261-70.

Mullin, G.E., et al., "Inflammatory bowel disease mucosal biopsies have specialized lymphokine mRNA profiles", Inflam Bowel Dis (1996); 2: 16-26.

Pospai, D., et al, "Crohn's disease stable remission after human immunodeficient virus infection", Dig Dis Sci (1998); 43: 412-9.

Stronkhorst, A., et al., "CD4 antibody treatment in patients with active Crohn's disease: a phase 1 dose finding study", Gut (1997); 40: 320-7.

Sadlack, B. et al., "Ulcerative colitis-like disease in mice with a disrupted interleukin-2 gene", Cell (1993); 75: 253-61.

Kuhn, R. et al., "Interleukin-10-deficient mice develop chronic enterocolitis", Cell (1993); 75: 263-74.

Powrie, F. et al., "Inhibition of Th1 responses prevents inflammatory bowel disease in SCID mice reconstituted with CD45RBhi CD4+ T cells", Immunity (1994); 1: 553-62.

Liu, Z. et al., "Hyperexpression of CD40 Ligand (CD154) in inflammatory bowel disease and its role in pathogenic cytokine production", J Immunol (1999); 163: 4049-57.

D'Haens, G. et al., "Early lesions caused by infusion of intestinal contents in excluded ileum in Crohn's disease", Gastroenterology (1998); 114: 262-7.

Cornillie, F. et al., "Infliximab induces potent anti-inflammatory and local immunomodulatory activity but no systemic immune suppression in patients with Crohn's disease", Aliment Pharmacol Ther (2001); 15: 2041-2.

Inwald, D.P., et al., "CD40 is constitutively expressed on platelets and provides a novel mechanism for platelet activation", Circ Res (2003); 92: 1041-8.

Van Assche, G, et al., "Anti-TNF agents in Crohn's disease", Expert Opin Investig Drugs (2000); 9: 103-11.

Stuber, E, et al., "Blocking the CD40L-CD40 interaction in vivo specifically prevents the priming of T helper 1 cells through the inhibition of interleukin 12 secretion", J Exp Med (1996);183:693-698.

Ranheim, E.A., et al., "Activated T cells induce expression of B7/BB1 on normal or leukemic B cells through a CD40-dependent signal", J Exp Med (1993);177:925-935.

Hasbold, J. et al., "Properties of mouse CD40: cellular distribution of CD40 and B cell activation by monoclonal anti-mouse CD40 antibodies", Eur J Immunol (1994);24:1835-1842.

Alderson, M R, et al., "CD40 expression by monocytes: regulation by cytokines and activation of monocytes by the ligand for CD40". J Exp Med (1993);178:669-674.

Kiener, P. A., et al. "Stimulation of CD40 with purified soluble gp39 induces proinflammatory responses in human monocytes", J Immunol (1995);155:4917-4925.

Shu U. et al., "Activated T cells induce interleukin-12 production by monocytes via CD40-CD40 ligand interaction", Eur J Immunol (1995);25:1125-1128.

Cella, M., et al., "Ligation of CD40 on dendritic cells triggers production of high levels of interleukin-12 and enhances T cell stimulatory capacity: T-T help via APC activation", J Exp Med (1996);184:747-752.

Van Kooten, C., et al., "Functions of CD40 on B cells, dendritic cells and other cells", Curr Opin Immunol (1997);9:330-337.

Cayabyab, M., et al., "CD40 preferentially costimulates activation of CD4+ T lymphocytes", J Immunol (1994);152:1523-1531.

Hermann, P. et al., "CD40 ligand-positive CD8+ T cell clones allow B cell growth and differentiation", Eur J Immunol (1995);25:2972-2977.

Grewal, I. S., et al., "CD40 and CD154 in cell-mediated immunity", Annu Rev Immunol (1998);16:111-135.

Henn V. et al., "CD40 ligand on activated platelets triggers an inflammatory reaction of endothelial cells", Nature (1998);391:591-594.

Banchereau, J. et al., "The CD40 antigen and its ligand", Annu Rev Immunol (1994);12:881-922.

Foy, T.M., et al., "Immune regulation by CD40 and its ligand gp39", Annu Rev Immunol (1996);14:591-617.

Kato, T., "Induction of IL-12 p40 messenger RNA expression and IL-12 production of macrophages via CD40-CD40 ligand interaction", J Immunol (1996);156:3932-3938.

Ludewig, B. et al., "Spontaneous apoptosis of dendritic cells is efficiently inhibited by TRAP (CD40-ligand) and TNF-a, but strongly enhanced by interleukin-10", Eur J Immunol (1995);25:1943-1950.

Allen, R. C., et al., "CD40 ligand gene defects responsible for X-linked hyper-IgM syndrome", Science (1993);259:990-993.

Xu J., et al., "Mice deficient for the CD40 ligand", Immunity (1994);1:423-431.

Grewal, I. S., et al., "Impairment of antigen-specific T-cell priming in mice lacking CD40 ligand", Nature (1995);378:617-620.

Stout, R.D., et al., "Impaired T cell-mediated macrophage activation in CD40 ligand-deficient mice", J Immunol (1996);156:8-11.

Levy, J., et al., Clinical spectrum of X-linked hyper-IgM sysdrome. J Pediatr (1997);131:47-54.

Soong, L., et al., "Disruption of CD40-CD40 ligand interactions results in an enhanced susceptibility to *Leishmania amazonensis* infection", Immunity (1996);4:263-273.

Campbell, K. A., et al., "CD40 ligand is required for protective cell-mediated immunity to *Leishmania major*", Immunity (1996);4:283-289.

Clegg, C. H., et al., "Thymus dysfunction and chronic inflammatory disease in gp39 transgenic mice", Int Immunol (1997);9:1111-1122.

Parker, et al., "Survival of Mouse Pancreatic Islet Allografts in Recipients Treated with Allogenic Small Lymphocytes and Antibody to CD-40 Ligand", Proc. Nat. Acad. Sci. USA (1995) 92:9560.

Haanstra, K. G., et al., "Prevention of kidney allograft rejection using anti-CD40 and anti-CD86 in primates", Transplantation. (2003);75(5):637-43.

Haanstra, K. G., et al., "Costimulation blockade followed by a 12-week period of cyclosporine A facilitates prolonged drug-free survival of Rhesus Monkey kidney allografts". Transplantation. (2005); 79: 1623-1626.

Boon, L. et al., "Prevention of experimental autoimmune encephalomyelitis in the common marmoset(*Callithrix jacchus*) using a chimeric antagonist monoclonal antibody against humanCD40 is associated with altered B cell responses", J Immunol (2001); 167:2942-2949.

(56) References Cited

OTHER PUBLICATIONS

Laman, J. D., et al., "Protection of marmoset monkeys against EAE by treatment with a murine antibody blocking CD40 (mu5D12)", Eur J Immunol (2002); 32:2218-2228.
Boon, L., et al., "Preclinical assessment of anti-CD40 Mab 5D12 in cynomolgus monkeys". Toxicology (2002); 174:53-65.
Kasran, A., et al., "Safety and tolerability of antagonist anti-human CD40 Mab ch5D12 in patients with moderate to severe Crohn's disease", Aliment Pharmacol Ther. (2005);22:111-22.
Haanstra, K. G., et al., "Costimulation blockade followed by a 12-week period of cyclosporine A facilitates prolonged drug-free survival of rhesus monkey kidney allografts", Transplantation. (2005);79:1623-6.
'T Hart B A, et al., "Treatment with chimeric anti-human CD40 antibody suppresses MRI-detectable inflammation and enlargement of pre-existing brain lesions in common marmosets affected by MOG-induced EAE", .J Neuroimmunol. (2005);163:31-9.
Koenen, H. J., et al., "A novel bispecific antihuman CD40/CD86 fusion protein with t-cell tolerizing potential", Transplantation. (2004); 78:1429-38.
De Vos, A. F., et al., "Antagonist anti-human CD40 antibody inhibits germinal center formation in cynomolgus monkeys", Eur J. Immunol. (2004);34:3446-55.
Laman, J. D., et al., "Protection of marmoset monkeys against EAE by treatment with a murine antibody blocking CD40 (mu5D12)", Eur J. Immunol. (2002);32:2218-28.
Samoilova, E. B., et al, "CD40L blockade prevents autoimmune encephalomyelitis and hampers TH1 but not TH2 pathway of T cell differentiation", J. Mol. Med. (1997);75: 603-608.
Boon, L. et al., "Prevention of experimental autoimmune encephalomyelitis in the common marmoset (*Callithrix jacchus*) using a chimeric antagonist monoclonal antibody against human CD40 is associated with altered B cell responses", J. Immunol. (2001);167:2942-9.
Antunes, S. G., et al., "The common marmoset: a new world primate species with limited Mhc class II variability", Proc. Natl. Acad. Sci. U.S. A. (1998);95:, 11745-11750.
Becher, B., et al., "The clinical course of experimental autoimmune encephalomyelitis and inflammation is controlled by the expression of CD40 within the central nervous system", J. Exp. Med. (2001);193:. 967-974.
Bontrop, R. E., et al., "Major histocompatibility complex class II polymorphisms in primates", Immunol. Rev. (1999);167:. 339-350.
Brok, H. P., et al., "Myelin/oligodendrocyte glycoprotein-induced autoimmune encephalomyelitis in common marmosets: the encephalitogenic T cell epitope pMOG24-36 is presented by a monomorphic MHC class II molecule", J. Immunol. (2000);165: 1093-1101.
Brok, H. P., et al., "Non-human primate models of multiple sclerosis", Immunol. Rev. (2001);183: 173-185.
Genain, C. P., et al., "Experimental allergic encephalomyelitis in the New World monkey *Callithrix jacchus*", Immunol. Rev. (2001);183: 159-172.
Gerritse, K., et al., "CD40-CD40 ligand interactions in experimental allergic encephalomyelitis and multiple sclerosis", Proc. Natl. Acad. Sci. U.S. A. (1996);93: 2499-2504.
Girvin, A. M., et al., "CD40/CD40L interaction is essential for the induction of EAE in the absence of CD28-mediated co-stimulation", J. Autoimmun.(2002);18:83-94.
Grewal, I. S., et al., "A central role of CD40 ligand in the regulation of CD4+ T-cell responses", Immunol. Today (1996);17:410-414.
Howard, L. M., et al., "Mechanisms of immunotherapeutic intervention by anti-CD40L (CD154) antibody in an animal model of multiple sclerosis", J. Clin. Invest. (1999);103:281-290.
Jordan, E. K., et al., "Serial M R imaging of experimental autoimmune encephalomyelitis induced by human white matter or by chimeric myelin-basic and proteolipid protein in the common marmoset", AJNR Am. J. Neuroradiol. (1999);20:965-976.
Laman, J. D., et al., "Functions of CD40 and its ligand, gp39 (CD40L)", Crit. Rev. Immunol.(1996);16:59-108.

J. D. Laman, et al., "Therapy with antibodies against CD40L (CD154) and CD44-variant isoforms reduces experimental autoimmune encephalomyelitis induced by a proteolipid protein peptide", Mult. Scler. (1998);4: 147-153.
Laman, J. D., et al., "Expression of accessory molecules and cytokines in acute EAE in marmoset monkeys (*Callithrix jacchus*)", J. Neuroimmunol. (1998);86:30-45.
Mestas, J., et al., "Of mice and not men: differences between mouse and human immunology", J. Immunol. (2004);172: 2731-2738.
Quezada, S. A., et al., "CD40/CD154 interactions at the interface of tolerance and immunity", Annu. Rev. Immunol. (2004);22:307-328.
Raine, C. S., et al., "Demyelination in primate autoimmune encephalomyelitis and acute multiple sclerosis lesions: a case for antigen-specific antibody mediation", Ann. Neurol. (1999);46:144-160.
Sachs, D. H., "Tolerance: of mice and men", J. Clin. Invest. (2003);111:1819-1821.
Pasch, M. C., et al., "In situ demonstration of CD40—and CD154-positive cells in psoriatic lesions and keratinocyte production of chemokines by CD40 ligation in vitro", J. Pathol (2004); 203:839-848.
Zebedee, et al., "Human Combinatorial Antibody Libraries to Hepatitis B Surface Antigen," Proc. Natl. Acad. Sci. USA, pp. 3175-3179, vol. 89 (Apr. 1992).
Kang, et al., "Antibody Redesign by Chain Shuffling From Random Combinatorial Immunoglobulin Libraries," Proc. Natl. Acad. Sci. USA, pp. 11120-11123, vol. 88 (Dec. 1991).
Roit, et al., "Immunology," M:Mir, pp. 110-111 (2000).
Diamond, et al., "Somatic Mutation of the T15 Heavy Chain Gives Rise to an Antibody with Autoantibody Specificity," Proc. Natl. Acad. Sci. USA, pp. 5841-5844, 81(18), Sep. 1984.
C.J. Epstein, "Non-Randomness of Amino-Acid Changes in the Evolution of Homologous Proteins", Nature, vol. 215, pp. 355-356 (1967).
B. A. 'T Hart, et al., "Histopathological characterization of magnetic resonance imaging-detectable brain white matter lesions in a primate model of multiple sclerosis: a correlative study in the experimental autoimmune encephalomyelitis model in common marmosets (*Callithrix jacchus*)", Am. J. Pathol. (1998);153:649-663.
B. A. 'T Hart, et al., "A new primate model for multiple sclerosis in the common marmoset", Immunol. Today (2000);21:290-297.
B. 'T Hart, et al., "Evaluating the validity of animal models for research into therapies for immune-based disorders", Drug Discov. Today (2004);9: 517-524.
B. 'T Hart et al., "Modelling of multiple sclerosis: lessons learned in a non-human primate", Lancet Neurol (2004);3: 589-597.
B. A. 'T Hart, et al., "Non-invasive measurement of brain damage in a primate model of multiple sclerosis", Trends Mol. Med. (2004);10: 85-91.
P. Villoslada, et al., "Frequency, heterogeneity and encephalitogenicity of T cells specific for myelin oligodendrocyte glycoprotein in naive outbred primates", Eur. J. Immunol. (2001);31: 2942-2950.
Bata-Csorgo, Z., et al., "Intralesional T-lymphocyte activation as a mediator of psoriatic epidermal hyperplasia", J Invest Dermatol (1995); 105(1 Suppl): 89S-94S.
Bos, J. D., et al., "The pathogenesis of psoriasis: immunological facts and speculations", Immunol Today (1999); 20: 40-46.
Lebwohl, M., "Psoriasis", Lancet (2003); 361: 1197-1204.
Van Kooten, C., et al., "CD40-CD40 ligand", J Leukoc Biol (2000); 67: 2-17.
Peguet-Navarro, J., et al., "CD40 ligation of human keratinocytes inhibits their proliferation and induces their differentiation", Immunol (1997); 158: 144-152.
Denfeld, R.W., et al., "CD40 is functionally expressed on human keratinocytes", Eur J Immunol (1996); 26: 2329-2334.
Gaspari, A. A., et al., "Human epidermal keratinocytes are induced to secrete interleukin-6 and co-stimulate T lymphocyte proliferation by a CD40-dependent mechanism", Eur J Immunol (1996); 26: 1371-1377.
Pasch, M. C., et al., "Activation of complement from psoriasis", Clin Exp Dermatol (1998); 23: 189-190.

* cited by examiner

Mu5D12 VH region

```
Q   V   K   L     E   E   S     G   P   G     L   V   A   P     S   Q   S     L   S   I
        10                20                30                40                50                60
CAGGTCAAGC    TCGAGGAGTC    TGGACCTGGC    CTGGTGGCAC    CCTCACAGAG    CCTGTCCATC
GTCCAGTTCG    AGCTCCTCAG    ACCTGGACCG    GACCACCGTG    GGAGTGTCTC    GGACAGGTAG

T   C   T   V     S   G   F     S   L   S     R   Y   S   V     Y   W   V     R   Q   P
        70                80                90               100               110               120
ACATGCACTG    TCTCTGGGTT    CTCATTATCC    AGATATAGTG    TATACTGGGT    TCGCCAGCCT
TGTACGTGAC    AGAGACCCAA    GAGTAATAGG    TCTATATCAC    ATATGACCCA    AGCGGTCGGA

P   G   K   G     L   E   W     L   G   M     M   W   G   G     G   S   T     D   Y   N
       130               140               150               160               170               180
CCAGGAAAGG    GTCTGGAGTG    GCTGGGAATG    ATGTGGGGTG    GTGGATCCAC    AGACTATAAT
GGTCCTTTCC    CAGACCTCAC    CGACCCTTAC    TACACCCCAC    CACCTAGGTG    TCTGATATTA

S   A   L   K     S   R   L     S   I   S     K   D   T   S     K   S   Q     V   F   L
       190               200               210               220               230               240
TCAGCTCTCA    AATCCAGACT    GAGCATCAGC    AAGGACACCT    CGAAGAGCCA    GGTCTTCTTA
AGTCGAGAGT    TTAGGTCTGA    CTCGTAGTCG    TTCCTGTGGA    GCTTCTCGGT    CCAGAAGAAT

K   M   N   S     L   R   T     D   D   T     A   M   Y   Y     C   V   R     T   D   G
       250               260               270               280               290               300
AAAATGAACA    GTCTGCGAAC    TGATGACACA    GCCATGTACT    ACTGTGTCAG    AACCGATGGG
TTTTACTTGT    CAGACGCTTG    ACTACTGTGT    CGGTACATGA    TGACACAGTC    TTGGCTACCC

D   Y   W   G     Q   G   T     S   V   T     V   S   S   (SEQ. ID. NO.: 46)
       310               320               330             339
GACTACTGGG    GTCAAGGAAC    CTCAGTCACC    GTCTCCTCA   (SEQ. ID. NO.: 45)
CTGATGACCC    CAGTTCCTTG    GAGTCAGTGG    CAGAGGAGT
```

Mu5D12 VL region

```
E   L   Q   L     T   Q   S     P   L   S     L   P   V   S     L   G   D     Q   A   S
        10                20                30                40                50                60
GAGCTCCAGC    TGACCCAGTC    TCCACTCTCC    CTGCCTGTCA    GTCTTGGAGA    TCAAGCCTCC
CTCGAGGTCG    ACTGGGTCAG    AGGTGAGAGG    GACGGACAGT    CAGAACCTCT    AGTTCGGAGG

I   S   C   R     S   S   Q     S   L   V     N   S   N   G     N   T   Y     L   H   W
        70                80                90               100               110               120
ATCTCTTGCA    GATCTAGTCA    GAGCCTTGTA    AACAGTAATG    GAAACACCTA    TTTACATTGG
TAGAGAACGT    CTAGATCAGT    CTCGGAACAT    TTGTCATTAC    CTTTGTGGAT    AAATGTAACC

Y   L   Q   K     P   G   Q     S   P   K     L   L   I   Y     K   V   S     N   R   F
       130               140               150               160               170               180
TACCTGCAGA    AGCCAGGCCA    GTCTCCAAAG    CTCCTGATCT    ACAAAGTTTC    CAACCGATTT
ATGGACGTCT    TCGGTCCGGT    CAGAGGTTTC    GAGGACTAGA    TGTTTCAAAG    GTTGGCTAAA

S   G   V   P     D   R   F     S   G   S     G   S   G   T     D   F   T     L   K   I
       190               200               210               220               230               240
TCTGGGGTCC    CAGACAGGTT    CAGTGGCAGT    GGATCAGGGA    CAGATTTCAC    ACTCAAGATT
AGACCCCAGG    GTCTGTCCAA    GTCACCGTCA    CCTAGTCCCT    GTCTAAAGTG    TGAGTTCTAA

S   R   V   E     A   E   D     L   G   V     Y   F   C   S     Q   S   T     H   V   P
       250               260               270               280               290               300
AGCAGAGTGG    AGGCTGAGGA    TCTGGGAGTT    TATTTCTGCT    CTCAAAGTAC    ACATGTTCCG
TCGTCTCACC    TCCGACTCCT    AGACCCTCAA    ATAAAGACGA    GAGTTTCATG    TGTACAAGGC

W   T   F   G     G   G   T     K   L   E     I   K   R   (SEQ. ID. NO.: 48)
       310               320               330             339
TGGACGTTCG    GTGGAGGCAC    CAAGCTGGAA    ATCAAACGT   (SEQ. ID. NO.: 47)
ACCTGCAAGC    CACCTCCGTG    GTTCGACCTT    TAGTTTGCA
```

Fig. 5

12 variants DI5D12VH

```
1.  Q5E       1  QVKLEESGPGLVKPSETLSITCTVSGFSISRYSVYWIRQPPGKGPEWMGMMWGGGSTDYS 60
2.  K13A      1  QVKLQESGPGLVAPSETLSITCTVSGFSISRYSVYWIRQPPGKGPEWMGMMWGGGSTDYS 60
3.  E16Q      1  QVKLQESGPGLVKPSQTLSITCTVSGFSISRYSVYWIRQPPGKGPEWMGMMWGGGSTDYS 60
4.  T17S      1  QVKLQESGPGLVKPSESLSITCTVSGFSISRYSVYWIRQPPGKGPEWMGMMWGGGSTDYS 60
5.  I29L      1  QVKLQESGPGLVKPSETLSITCTVSGFSLSRYSVYWIRQPPGKGPEWMGMMWGGGSTDYS 60
6.  I37V      1  QVKLQESGPGLVKPSETLSITCTVSGFSISRYSVYVVRQPPGKGPEWMGMMWGGGSTDYS 60
7.  P45L      1  QVKLQESGPGLVKPSETLSITCTVSGFSISRYSVYWIRQPPGKGLEWMGMMWGGGSTDYS 60
8.  M48L      1  QVKLQESGPGLVKPSETLSITCTVSGFSISRYSVYWIRQPPGKGPEWLGMMWGGGSTDYS 60
9.  STS60NSA  1  QVKLQESGPGLVKPSETLSITCTVSGFSISRYSVYWIRQPPGKGPEWMGMMWGGGSTDYN 60
10. T68S      1  QVKLQESGPGLVKPSETLSITCTVSGFSISRYSVYWIRQPPGKGPEWMGMMWGGGSTDYS 60
11. S79F      1  QVKLQESGPGLVKPSETLSITCTVSGFSISRYSVYWIRQPPGKGPEWMGMMWGGGSTDYS 60
12. T108S     1  QVKLQESGPGLVKPSETLSITCTVSGFSISRYSVYWIRQPPGKGPEWMGMMWGGGSTDYS 60

CH5D12    1  QVKLEESGPGLVAPSQSLSITCTVSGFSLSRYSVYWVRQPPGKGLEWLGMMWGGGSTDYN 60
    DI5D12    1  QVKLQESGPGLVKPSETLSITCTVSGFSISRYSVYWIRQPPGKGPEWMGMMWGGGSTDYS 60
```

```
1.   Q5E              61  TSLKSRLTISKDTSKSQVSLKMNSLRTDDTAMYYCVRTDGDYWGQGTTVTVSS 113
    (SEQ.ID. NO.: 53)
2.   K13A             61  TSLKSRLTISKDTSKSQVSLKMNSLRTDDTAMYYCVRTDGDYWGQGTTVTVSS 113
    (SEQ.ID. NO.: 54)
3.   E16Q             61  TSLKSRLTISKDTSKSQVSLKMNSLRTDDTAMYYCVRTDGDYWGQGTTVTVSS 113
    (SEQ.ID. NO.: 55)
4.   T17S             61  TSLKSRLTISKDTSKSQVSLKMNSLRTDDTAMYYCVRTDGDYWGQGTTVTVSS 113
    (SEQ.ID. NO.: 56)
5.   I29L             61  TSLKSRLTISKDTSKSQVSLKMNSLRTDDTAMYYCVRTDGDYWGQGTTVTVSS 113
    (SEQ.ID. NO.: 57)
6.   I37V             61  TSLKSRLTISKDTSKSQVSLKMNSLRTDDTAMYYCVRTDGDYWGQGTTVTVSS 113
    (SEQ.ID. NO.: 58)
7.   P45L             61  TSLKSRLTISKDTSKSQVSLKMNSLRTDDTAMYYCVRTDGDYWGQGTTVTVSS 113
    (SEQ.ID. NO.: 59)
8.   M48L             61  TSLKSRLTISKDTSKSQVSLKMNSLRTDDTAMYYCVRTDGDYWGQGTTVTVSS 113
    (SEQ.ID. NO.: 60)
9.   STS60NSA         61  SALKSRLTISKDTSKSQVSLKMNSLRTDDTAMYYCVRTDGDYWGQGTTVTVSS 113
    (SEQ.ID. NO.: 61)
10.  T68S             61  TSLKSRLSISKDTSKSQVSLKMNSLRTDDTAMYYCVRTDGDYWGQGTTVTVSS 113
    (SEQ.ID. NO.: 62)
11.  S79F             61  TSLKSRLTISKDTSKSQVFLKMNSLRTDDTAMYYCVRTDGDYWGQGTTVTVSS 113
    (SEQ.ID. NO.: 63)
12.  T108S            61  TSLKSRLTISKDTSKSQVSLKMNSLRTDDTAMYYCVRTDGDYWGQGTSVTVSS 113
    (SEQ.ID. NO.: 64)

CH5D12           61  SALKSRLSISKDTSKSQVFLKMNSLRTDDTAMYYCVRTDGDYWGQGTSVTVSS 113
    (SEQ.ID. NO.: 65)
     DI5D12           61  TSLKSRLTISKDTSKSQVSLKMNSLRTDDTAMYYCVRTDGDYWGQGTTVTVSS 113
    (SEQ.ID. NO.: 66)
```

Fig. 7

Fig. 8
Q5E
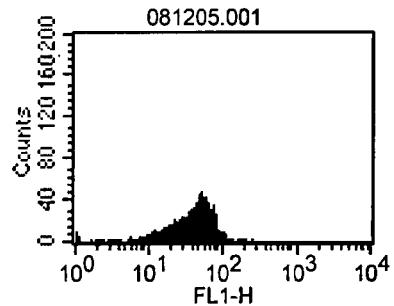
| % Gated | Mean | Median |
|---|---|---|
| 100.00 | 39.05 | 37.52 |
K13A
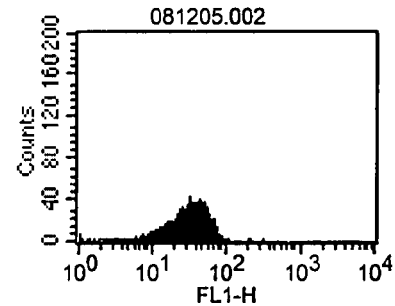
| % Gated | Mean | Median |
|---|---|---|
| 100.00 | 31.22 | 29.96 |
E16Q
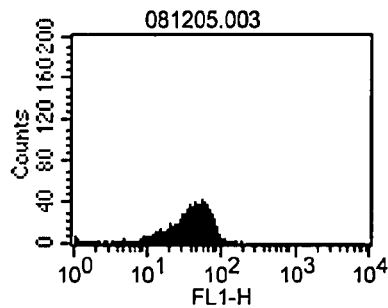
| % Gated | Mean | Median |
|---|---|---|
| 100.00 | 39.48 | 38.20 |
T17S
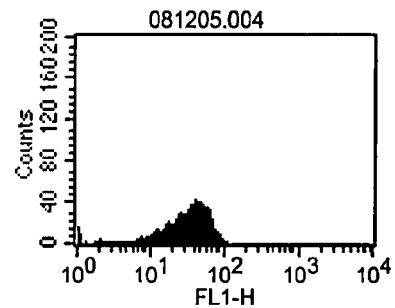
| % Gated | Mean | Median |
|---|---|---|
| 100.00 | 33.43 | 31.91 |
I29L
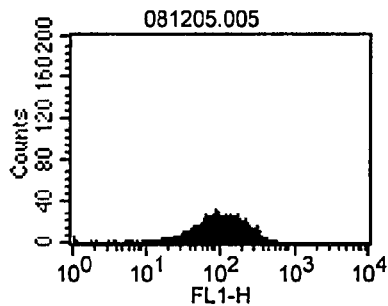
| % Gated | Mean | Median |
|---|---|---|
| 100.00 | 108.28 | 91.81 |
I37V
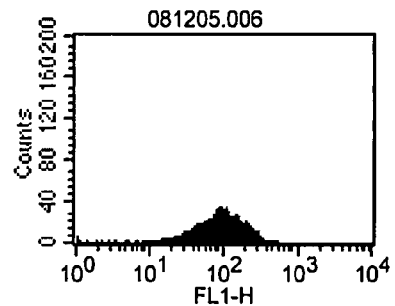
| % Gated | Mean | Median |
|---|---|---|
| 100.00 | 96.05 | 82.05 |

Fig. 8, Condt.
P45L
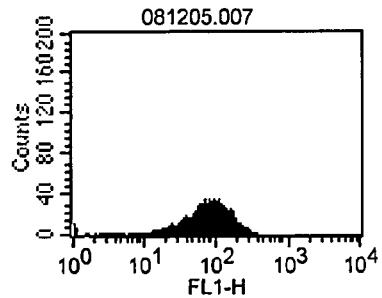
| % Gated | Mean | Median |
|---|---|---|
| 100.00 | 82.53 | 74.32 |
M48L
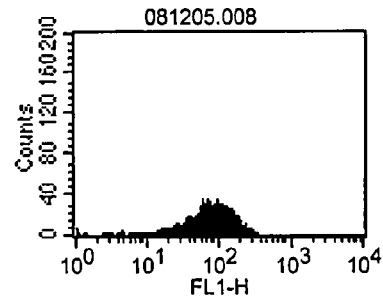
| % Gated | Mean | Median |
|---|---|---|
| 100.00 | 80.30 | 72.34 |
STS60NSA
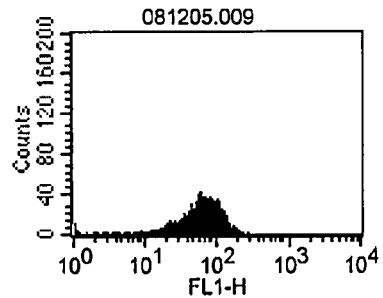
| % Gated | Mean | Median |
|---|---|---|
| 100.00 | 62.37 | 58.82 |
T68S
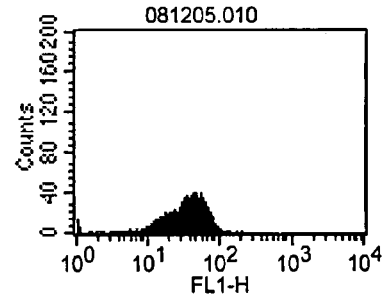
| % Gated | Mean | Median |
|---|---|---|
| 100.00 | 35.21 | 33.98 |
S79F
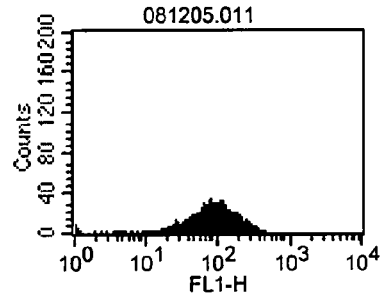
| % Gated | Mean | Median |
|---|---|---|
| 100.00 | 96.40 | 82.05 |
T108S
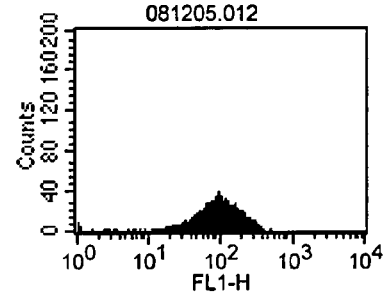
| % Gated | Mean | Median |
|---|---|---|
| 100.00 | 99.04 | 85.82 |

Fig. 8, Condt.
Ch5D12
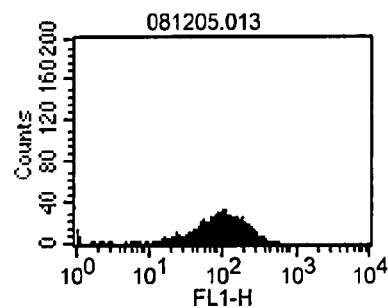
| % Gated | Mean | Median |
|---|---|---|
| 100.00 | 102.97 | 88.96 |
DI5D12
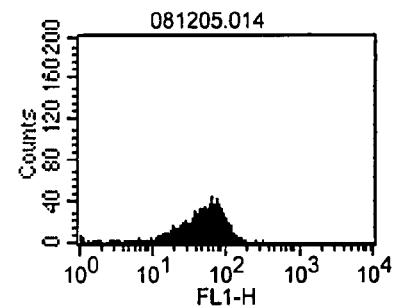
| % Gated | Mean | Median |
|---|---|---|
| 100.00 | 50.44 | 47.40 |
Mock Control
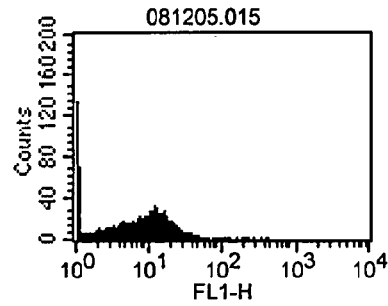
| % Gated | Mean | Median |
|---|---|---|
| 100.00 | 11.25 | 8.74 |
FACS control
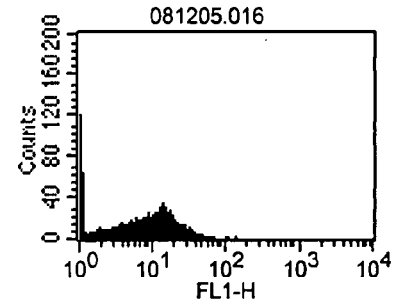
| % Gated | Mean | Median |
|---|---|---|
| 100.00 | 10.18 | 8.74 |

V-L-I variants of DI5D12 VH

```
1.   IV         1  QVKLQESGPGLVKPSETLSITCTVSGFSISRYSVYWVRQPPGKGPEWMGMMWGGGSTDYSTS  62
2.   VI         1  QVKLQESGPGLVKPSETLSITCTVSGFSVSRYSVYWIRQPPGKGPEWMGMMWGGGSTDYSTS  62
3.   IL         1  QVKLQESGPGLVKPSETLSITCTVSGFSISRYSVYWLRQPPGKGPEWMGMMWGGGSTDYSTS  62
4.   VV         1  QVKLQESGPGLVKPSETLSITCTVSGFSVSRYSVYWVRQPPGKGPEWMGMMWGGGSTDYSTS  62
5.   LL         1  QVKLQESGPGLVKPSETLSITCTVSGFSLSRYSVYWLRQPPGKGPEWMGMMWGGGSTDYSTS  62
6.   VL         1  QVKLQESGPGLVKPSETLSITCTVSGFSVSRYSVYWLRQPPGKGPEWMGMMWGGGSTDYSTS  62
7.   LV         1  QVKLQESGPGLVKPSETLSITCTVSGFSLSRYSVYWVRQPPGKGPEWMGMMWGGGSTDYSTS  62

CH5D12 (PG100) 1  QVKLEESGPGLVAPSQSLSITCTVSGFSLSRYSVYWVRQPPGKGLEWLGMMWGGGSTDYNSA  62
DI5D12 (II)    1  QVKLQESGPGLVKPSETLSITCTVSGFSISRYSVYWIRQPPGKGPEWMGMMWGGGSTDYSTS  62
PG102  (LI)    1  QVKLQESGPGLVKPSETLSITCTVSGFSLSRYSVYWIRQPPGKGPEWMGMMWGGGSTDYSTS  62

1.   IV        63  LKSRLTISKDTSKSQVSLKMNSLRTDDTAMYYCVRTDGDYWGQGTTVTVSS  113
(SEQ.ID. NO.: 67)
2.   VI        63  LKSRLTISKDTSKSQVSLKMNSLRTDDTAMYYCVRTDGDYWGQGTTVTVSS  113
(SEQ.ID. NO.: 68)
3.   IL        63  LKSRLTISKDTSKSQVSLKMNSLRTDDTAMYYCVRTDGDYWGQGTTVTVSS  113
(SEQ.ID. NO.: 69)
4.   VV        63  LKSRLTISKDTSKSQVSLKMNSLRTDDTAMYYCVRTDGDYWGQGTTVTVSS  113
(SEQ.ID. NO.: 70)
5.   LL        63  LKSRLTISKDTSKSQVSLKMNSLRTDDTAMYYCVRTDGDYWGQGTTVTVSS  113
(SEQ.ID. NO.: 71)
6.   VL        63  LKSRLTISKDTSKSQVSLKMNSLRTDDTAMYYCVRTDGDYWGQGTTVTVSS  113
(SEQ.ID. NO.: 72)
7.   LV        63  LKSRLTISKDTSKSQVSLKMNSLRTDDTAMYYCVRTDGDYWGQGTTVTVSS  113
(SEQ.ID. NO.: 73)

CH5D12 (PG102) 63  LKSRLSISKDTSKSQVFLKMNSLRTDDTAMYYCVRTDGDYWGQGTSVTVSS  113
(SEQ.ID. NO.: 74)
DI5D12 (II)    63  LKSRLTISKDTSKSQVSLKMNSLRTDDTAMYYCVRTDGDYWGQGTTVTVSS  113
(SEQ.ID. NO.: 75)
PG102  (LI)    63  LKSRLTISKDTSKSQVSLKMNSLRTDDTAMYYCVRTDGDYWGQGTTVTVSS  113
(SEQ.ID. NO.: 76)
```

Protein sequence of PG102 heavy and light chain

Signal sequences are underlined, variable regions in bold.

Heavy chain:

MEWSWVFLFFLSVTTGVHSQVKLQESGPGLVKPSETLSITCTVSGFSLSRYSVYWIRQPPGKGPEWMG
MMWGGGSTDYSTSLKSRLTISKDTSKSQVSLKMNSLRTDDTAMYYCVRTDGDYWGQGTTVTVSSASTK
GPSVFPLAPCSRSTSESTAALGCLVKDYFPEPVTVSWNSGALTSGVHTFPAVLQSSGLYSLSSVVTVP
SSSLGTKTYTCNVDHKPSNTKVDKRVESKYGPPCPSCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPP
VLDSDGSFFLYSRLTVDKSRWQEGNVFSCSVMHEALHNHYTQKSLSLSLGK (SEQ.ID. NO.: 78)

Light chain:

MSVPTQVLGLLLLWLTDARCELQLTQSPLSLPVTLGQPASISCRSSQSLANSNGNTYLHWYLQRPGQS
PRLLIYKVSNRFSGVPDRFSGSGSGTDFTLKISRVEAEDVGVYYCSQSTHVPWTFGGGTKLEIKRTVA
APSVFIFPPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC (SEQ.ID. NO.: 80)

Fig. 18, Condt.

DNA sequences encoding PG102 heavy and light chains

Signal sequences is indicated as underlined, variable regions in bold, and stop codons in lower case.

Heavy chain:
ATGGAGTGGTCTTGGGTGTTCCTGTTCTTCCTGTCTGTGACAACAGGAGTGCACTCT**CAGGTCAAGCT
GCAGGAGTCTGGACCAGGACTGGTGAAGCCATCTGAGACCCTGAGCATCACCTGTACAGTGAGCGGCT
TCAGCCTCTCTAGATACAGCGTGTACTGGATCAGACAGCCACCTGGAAAGGGACCAGAGTGGATGGGA
ATGATGTGGGGAGGAGGATCTACAGACTACAGCACCAGCCTGAAGTCTAGACTGACCATCAGCAAGGA
CACCTCTAAGTCTCAGGTCTCCCTGAAGATGAACTCTCTGAGAACAGACGACACCGCCATGTACTACT
GTGTGAGAACCGACGGAGATTATTGGGGACAGGGCACAACAGTGACAGTGTCCTCTGCCTCTACAAAG**
GGACCATCTGTGTTTCCACTGGCCCCATGTTCTAGATCTACCAGCGAGTCTACAGCTGCTCTGGGATG
TCTGGTGAAGGACTACTTTCCAGAGCCTGTGACAGTGTCTTGGAATAGTGGAGCCCTGACATCTGGAG
TGCACACATTTCCAGCTGTGCTGCAGTCTAGCGGACTGTATTCTCTGTCCAGCGTGGTGACAGTGCCA
TCTTCTTCTCTGGGCACCAAGACCTACACATGTAACGTGGACCACAAGCCATCTAACACCAAGGTGGA
CAAGAGAGTGGAGTCTAAGTACGGACCACCATGCCCATCTTGTCCAGCTCCAGAGTTTCTGGGAGGAC
CTAGCGTGTTTCTGTTCCCCCCAAAGCCAAAGGATACCCTGATGATCTCTAGAACCCCAGAGGTGACA
TGTGTGGTGGTGGATGTGTCTCAGGAGGATCCAGAGGTCCAGTTTAACTGGTACGTGGATGGAGTGGA
GGTGCACAACGCTAAGACAAAGCCAAGAGAGGAGCAGTTCAACAGCACATACAGAGTGGTGTCTGTGC
TGACAGTGCTGCATCAGGATTGGCTGAACGGCAAGGAATACAAGTGTAAGGTCTCCAACAAGGGCCTG
CCATCTTCTATCGAGAAAACCATCTCTAAGGCTAAGGGACAGCCAAGGGAGCCACAGGTGTACACACT
GCCACCATCTCAAGAGGAGATGACCAAGAACCAGGTGTCCCTGACATGCCTGGTGAAGGGATTCTACC
CATCTGATATCGCTGTGGAGTGGGAGTCTAATGGACAGCCCGAGAACAACTACAAGACCACACCACCA
GTGCTGGATTCTGACGGCTCTTTCTTCCTGTACAGCAGACTGACAGTGGACAAGTCTAGATGGCAGGA
GGGAAACGTCTTTAGCTGTAGCGTGATGCATGAGGCTCTGCACAACCACTACACCCAGAAGTCTCTGT
CTCTGAGTCTGGGAAAAtgatag (SEQ. ID. NO.: 77)

Light chain:
ATGTCTGTGCCAACACAGGTGCTGGGACTGCTGCTGCTGTGGCTGACAGATGCTAGATGT**GAGCTGCA
GCTGACACAGTCTCCACTGTCTCTGCCAGTGACACTGGGACAGCCAGCTAGCATCAGCTGTAGAAGCT
CTCAGTCTCTGGCCAACTCTAACGGCAACACATACCTGCATTGGTATCTGCAGAGACCAGGACAGTCT
CCAAGACTGCTGATCTACAAGGTGTCCAACAGATTCTCTGGAGTGCCAGACAGATTTTCTGGCTCTGG
CTCTGGAACAGACTTCACCCTGAAGATCTCTAGAGTGGAGGCTGAGGATGTGGGAGTGTACTACTGCT
CTCAGTCTACACATGTGCCATGGACATTCGGAGGAGGAACAAAGCTGGAGATCAAGAGA**ACAGTGGCT
GCCCATCTGTGTTTATCTTCCCCCCATCTGATGAGCAGCTGAAGTCTGGAACAGCTTCTGTGGTGTG
TCTGCTGAACAACTTCTACCCAAGGGAGGCTAAGGTGCAGTGGAAGGTGGACAATGCTCTGCAGTCTG
GAAACTCTCAGGAGTCTGTCACAGAGCAGGACAGCAAGGACTCTACCTACTCTCTGAGCAGCACACTG
ACACTGTCTAAGGCCGACTACGAGAAGCATAAGGTGTACGCCTGTGAGGTGACACATCAGGGACTGTC
TAGCCCAGTGACCAAGTCTTTCAACAGAGGCGAGTGCtgatag (SEQ. ID. NO.: 79)

SEQUENCE LISTING

```
<160> NUMBER OF SEQ ID NOS: 96

<210> SEQ ID NO 1
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
```

Aspartic acid, Glutamic acid, Lysine, Arginine or Histidine
<220> FEATURE:
<221> NAME/KEY: VARIANT
<222> LOCATION: (12)..(12)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lycine, Arginine or Histidine
<220> FEATURE:
<221> NAME/KEY: VARIANT
<222> LOCATION: (20)..(20)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (23)..(23)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (54)..(54)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine

<400> SEQUENCE: 1

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Ser Thr
            20              25                  30

Asp Tyr Ser Thr Ser Leu Lys Ser Arg Leu Thr Ile Ser Lys Asp Thr
            35                  40                  45

Ser Lys Ser Gln Val Xaa Leu Lys Met Asn Ser Leu Arg Thr Asp Asp
        50              55                  60

Thr Ala Met Tyr Tyr Cys Val Arg Thr Asp Gly Asp Tyr
65                  70                  75

<210> SEQ ID NO 2
<211> LENGTH: 113
<212> TYPE: PRT
<213> ORGANISM: Artificial
<220> FEATURE:
<223> OTHER INFORMATION: VH Formula I
<220> FEATURE:
<221> NAME/KEY: VARIANT
<222> LOCATION: (29)..(29)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (37)..(37)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (45)..(45)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (48)..(48)
<223> OTHER INFORMATION: Xaa is Glycine, Alanine, Valine, Leucine,
      Isoleucine, Proline, Phenylalanine, Methionine, Tryptophan, -continued Cysteine, Asparagine, Glutamine, Serine, Threonine, Tyrosine,
Aspartic acid, Glutamic acid, Lysine, Arginine or Histidine
<220> FEATURE:
<221> NAME/KEY: VARIANT
<222> LOCATION: (79)..(79)
<223> OTHER INFORMATION: Xaa is Glycine, Alanine, Valine, Leucine,
Isoleucine, Proline, Phenylalanine, Methionine, Tryptophan,
Cysteine, Asparagine, Glutamine, Serine, Threonine, Tyrosine,
Aspartic acid, Glutamic acid, Lysine, Arginine or Histidine

<400> SEQUENCE: 2

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Xaa Ser Arg Tyr
            20                  25                  30

Ser Val Tyr Trp Xaa Arg Gln Pro Pro Gly Lys Gly Xaa Glu Trp Xaa
        35                  40                  45

Gly Met Met Trp Gly Gly Ser Thr Asp Tyr Ser Thr Ser Leu Lys
    50                  55                  60

Ser Arg Leu Thr Ile Ser Lys Asp Thr Ser Lys Ser Gln Val Xaa Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 3
<211> LENGTH: 13
<212> TYPE: PRT
<213> ORGANISM: Artificial
<220> FEATURE:
<223> OTHER INFORMATION: Polypeptide with amino acid - modified CDR1 of
      a 5D12 heavy chain variable fragment

<400> SEQUENCE: 3

Gly Phe Ser Leu Ser Arg Tyr Ser Val Tyr Trp Ile Arg
1               5                   10

<210> SEQ ID NO 4
<211> LENGTH: 13
<212> TYPE: PRT
<213> ORGANISM: Artificial
<220> FEATURE:
<223> OTHER INFORMATION: Polypeptide with amino acid - modified CDR1 of
      a 5D12 heavy chain variable fragment

<400> SEQUENCE: 4

Gly Phe Ser Ile Ser Arg Tyr Ser Val Tyr Trp Val Arg
1               5                   10

<210> SEQ ID NO 5
<211> LENGTH: 89
<212> TYPE: PRT
<213> ORGANISM: Artificial
<220> FEATURE:
<223> OTHER INFORMATION: VL Part Formula II
<220> FEATURE:
<221> NAME/KEY: VARIANT
<222> LOCATION: (1)..(1)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (4)..(4)

```
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (5)..(5)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (17)..(17)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (75)..(75)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (79)..(79)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine

<400> SEQUENCE: 5

Xaa Leu Gly Xaa Xaa Ala Ser Ile Ser Cys Arg Ser Ser Gln Ser Leu
1               5                   10                  15

Xaa Asn Ser Asn Gly Asn Thr Tyr Leu His Trp Tyr Leu Gln Arg Pro
            20                  25                  30

Gly Gln Ser Pro Arg Leu Leu Ile Tyr Lys Val Ser Asn Arg Phe Ser
        35                  40                  45

Gly Val Pro Asp Arg Phe Ser Gly Ser Gly Ser Gly Thr Asp Phe Thr
    50                  55                  60

Leu Lys Ile Ser Arg Val Glu Ala Glu Asp Xaa Gly Val Tyr Xaa Cys
65                  70                  75                  80

Ser Gln Ser Thr His Val Pro Trp Thr
                85

<210> SEQ ID NO 6
<211> LENGTH: 113
<212> TYPE: PRT
<213> ORGANISM: Artificial
<220> FEATURE:
<223> OTHER INFORMATION: VL Formula II
<220> FEATURE:
<221> NAME/KEY: VARIANT
<222> LOCATION: (14)..(14)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (17)..(17)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (18)..(18)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
```

-continued

```
       Aspartic acid, Glutamic acid, Lysine, Arginine or Histidine
<220>  FEATURE:
<221>  NAME/KEY: VARIANT
<222>  LOCATION: (30)..(30)
<223>  OTHER INFORMATION: Xaa is Glycine, Alanine, Valine, Leucine,
       Isoleucine, Proline, Phenylalanine, Methionine, Tryptophan,
       Cysteine, Asparagine, Glutamine, Serine, Threonine, Tyrosine,
       Aspartic acid, Glutamic acid, Lysine, Arginine or Histidine
<220>  FEATURE:
<221>  NAME/KEY: VARIANT
<222>  LOCATION: (88)..(88)
<223>  OTHER INFORMATION: Xaa is Glycine, Alanine, Valine, Leucine,
       Isoleucine, Proline, Phenylalanine, Methionine, Tryptophan,
       Cysteine, Asparagine, Glutamine, Serine, Threonine, Tyrosine,
       Aspartic acid, Glutamic acid, Lysine, Arginine or Histidine
<220>  FEATURE:
<221>  NAME/KEY: VARIANT
<222>  LOCATION: (92)..(92)
<223>  OTHER INFORMATION: Xaa is Glycine, Alanine, Valine, Leucine,
       Isoleucine, Proline, Phenylalanine, Methionine, Tryptophan,
       Cysteine, Asparagine, Glutamine, Serine, Threonine, Tyrosine,
       Aspartic acid, Glutamic acid, Lysine, Arginine or Histidine

<400>  SEQUENCE: 6

Glu Leu Gln Leu Thr Gln Ser Pro Leu Ser Leu Pro Val Xaa Leu Gly
1               5                   10                  15

Xaa Xaa Ala Ser Ile Ser Cys Arg Ser Ser Gln Ser Leu Xaa Asn Ser
            20                  25                  30

Asn Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Xaa Cys Ser Gln Ser
                85                  90                  95

Thr His Val Pro Trp Thr Phe Gly Gly Gly Thr Lys Leu Glu Ile Lys
            100                 105                 110

Arg

<210>  SEQ ID NO 7
<211>  LENGTH: 113
<212>  TYPE: PRT
<213>  ORGANISM: Artificial
<220>  FEATURE:
<223>  OTHER INFORMATION: VH Sequence (1)

<400>  SEQUENCE: 7

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Val Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser
```

```
<210> SEQ ID NO 8
<211> LENGTH: 113
<212> TYPE: PRT
<213> ORGANISM: Artificial
<220> FEATURE:
<223> OTHER INFORMATION: VH Sequence (2)

<400> SEQUENCE: 8

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 9
<211> LENGTH: 113
<212> TYPE: PRT
<213> ORGANISM: Artificial
<220> FEATURE:
<223> OTHER INFORMATION: VH Sequence (3)

<400> SEQUENCE: 9

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Val Ser Arg Tyr
            20                  25                  30

Ser Val Tyr Trp Val Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 10
<211> LENGTH: 113
<212> TYPE: PRT
<213> ORGANISM: Artificial
<220> FEATURE:
<223> OTHER INFORMATION: VH Sequence (4)

<400> SEQUENCE: 10

Gln Val Lys Leu Gln Glu Ser Gly Pro Gly Leu Val Lys Pro Ser Glu
1               5                   10                  15
```

```
Thr Leu Ser Ile Thr Cys Val Ser Gly Phe Ser Leu Ser Arg Tyr
            20                  25                  30

Ser Val Tyr Trp Leu Arg Gln Pro Pro Gly Lys Gly Pro Glu Trp Met
            35                  40                  45

Gly Met Met Trp Gly Gly Ser Thr Asp Tyr Ser Thr Ser Leu Lys
50                      55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser
```

```
<210> SEQ ID NO 11
<211> LENGTH: 113
<212> TYPE: PRT
<213> ORGANISM: Artificial
<220> FEATURE:
<223> OTHER INFORMATION: VH Sequence (5)

<400> SEQUENCE: 11
```

```
Gln Val Lys Leu Gln Glu Ser Gly Pro Gly Leu Val Lys Pro Ser Glu
1               5                   10                  15

Thr Leu Ser Ile Thr Cys Val Ser Gly Phe Ser Leu Ser Arg Tyr
            20                  25                  30

Ser Val Tyr Trp Val Arg Gln Pro Pro Gly Lys Gly Pro Glu Trp Met
            35                  40                  45

Gly Met Met Trp Gly Gly Ser Thr Asp Tyr Ser Thr Ser Leu Lys
50                      55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser
```

```
<210> SEQ ID NO 12
<211> LENGTH: 113
<212> TYPE: PRT
<213> ORGANISM: Artificial
<220> FEATURE:
<223> OTHER INFORMATION: VL Sequence

<400> SEQUENCE: 12
```

```
Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Asn Ser
                20                  25                  30

Asn Gly Asn Thr Tyr Leu His Trp Tyr Leu Gln Arg Pro Gly Gln Ser
            35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95
```

Thr His Val Pro Trp Thr Phe Gly Gly Gly Thr Lys Leu Glu Ile Lys
            100                 105                 110

Arg

<210> SEQ ID NO 13
<211> LENGTH: 23
<212> TYPE: DNA
<213> ORGANISM: Artificial
<220> FEATURE:
<223> OTHER INFORMATION: Primer 1 to amplify VH region

<400> SEQUENCE: 13
caggtsmarc tssagsagtc wgg                                    23

<210> SEQ ID NO 14
<211> LENGTH: 37
<212> TYPE: DNA
<213> ORGANISM: Artificial
<220> FEATURE:
<223> OTHER INFORMATION: Primer 2 to amplify VH region

<400> SEQUENCE: 14
gcatgtacta gtaattttv ttgtccacyt tggtgct                      37

<210> SEQ ID NO 15
<211> LENGTH: 30
<212> TYPE: DNA
<213> ORGANISM: Artificial
<220> FEATURE:
<223> OTHER INFORMATION: Primer 1 to amplify VL region

<400> SEQUENCE: 15
cgatacgasm tycagctgac ccagtctcca                             30

<210> SEQ ID NO 16
<211> LENGTH: 38
<212> TYPE: DNA
<213> ORGANISM: Artificial
<220> FEATURE:
<223> OTHER INFORMATION: Primer 2 to amplify VL region

<400> SEQUENCE: 16
gactcatcta gatacactca ttcctgttga agctcttg                    38

<210> SEQ ID NO 17
<211> LENGTH: 33
<212> TYPE: DNA
<213> ORGANISM: Artificial
<220> FEATURE:
<223> OTHER INFORMATION: Primer - Mutagenic oligonucleotide Q5E

<400> SEQUENCE: 17
ctcccaggtt aagcttgagg agtctggacc tgg                         33

<210> SEQ ID NO 18
<211> LENGTH: 33
<212> TYPE: DNA
<213> ORGANISM: Artificial
<220> FEATURE:
<223> OTHER INFORMATION: Primer - Mutagenic oligonucleotide Q5Erev

<400> SEQUENCE: 18
ccaggtccag actcctcaag cttaacctgg gag                         33

<210> SEQ ID NO 19

```
<211> LENGTH: 30
<212> TYPE: DNA
<213> ORGANISM: Artificial
<220> FEATURE:
<223> OTHER INFORMATION: Primer - Mutagenic oligonucleotide K13A

<400> SEQUENCE: 19
gacctggcct ggtggcaccc tcagagaccc                                    30

<210> SEQ ID NO 20
<211> LENGTH: 30
<212> TYPE: DNA
<213> ORGANISM: Artificial
<220> FEATURE:
<223> OTHER INFORMATION: Primer - Mutagenic oligonucleotide K13Arev

<400> SEQUENCE: 20
gggtctctga gggtgccacc aggccaggtc                                    30

<210> SEQ ID NO 21
<211> LENGTH: 33
<212> TYPE: DNA
<213> ORGANISM: Artificial
<220> FEATURE:
<223> OTHER INFORMATION: Primer - Mutagenic oligonucleotide E16Q

<400> SEQUENCE: 21
cctggtgaaa ccctcacaga ccctgtccat cac                                33

<210> SEQ ID NO 22
<211> LENGTH: 33
<212> TYPE: DNA
<213> ORGANISM: Artificial
<220> FEATURE:
<223> OTHER INFORMATION: Primer - Mutagenic oligonucleotide E16Qrev

<400> SEQUENCE: 22
gtgatggaca gggtctgtga gggtttcacc agg                                33

<210> SEQ ID NO 23
<211> LENGTH: 33
<212> TYPE: DNA
<213> ORGANISM: Artificial
<220> FEATURE:
<223> OTHER INFORMATION: Primer - Mutagenic oligonucleotide T17S

<400> SEQUENCE: 23
gtgaaaccct cagagagcct gtccatcaca tgc                                33

<210> SEQ ID NO 24
<211> LENGTH: 33
<212> TYPE: DNA
<213> ORGANISM: Artificial
<220> FEATURE:
<223> OTHER INFORMATION: Primer - Mutagenic oligonucleotide T17Srev

<400> SEQUENCE: 24
gcatgtgatg gacaggctct ctgagggttt cac                                33

<210> SEQ ID NO 25
<211> LENGTH: 41
<212> TYPE: DNA
<213> ORGANISM: Artificial
<220> FEATURE:
<223> OTHER INFORMATION: Primer - Mutagenic oligonucleotide I29L

<400> SEQUENCE: 25
```

```
gcactgtctc tgggttctca ctctccagat atagtgtata c                           41
```

<210> SEQ ID NO 26
<211> LENGTH: 41
<212> TYPE: DNA
<213> ORGANISM: Artificial
<220> FEATURE:
<223> OTHER INFORMATION: Primer - Mutagenic oligonucleotide I29Lrev

<400> SEQUENCE: 26

```
gtatacacta tatctggaga gtgagaaccc agagacagtg c                           41
```

<210> SEQ ID NO 27
<211> LENGTH: 34
<212> TYPE: DNA
<213> ORGANISM: Artificial
<220> FEATURE:
<223> OTHER INFORMATION: Primer - Mutagenic oligonucleotide I37V

<400> SEQUENCE: 27

```
gatatagtgt atactgggtt cgccagcctc cagg                                   34
```

<210> SEQ ID NO 28
<211> LENGTH: 34
<212> TYPE: DNA
<213> ORGANISM: Artificial
<220> FEATURE:
<223> OTHER INFORMATION: Primer - Mutagenic oligonucleotide I37Vrev

<400> SEQUENCE: 28

```
cctggaggct ggcgaaccca gtatacacta tatc                                   34
```

<210> SEQ ID NO 29
<211> LENGTH: 33
<212> TYPE: DNA
<213> ORGANISM: Artificial
<220> FEATURE:
<223> OTHER INFORMATION: Primer - Mutagenic oligonucleotide P45L

<400> SEQUENCE: 29

```
cctccaggaa agggtctgga gtggatggga atg                                    33
```

<210> SEQ ID NO 30
<211> LENGTH: 33
<212> TYPE: DNA
<213> ORGANISM: Artificial
<220> FEATURE:
<223> OTHER INFORMATION: Primer - Mutagenic oligonucleotide P45Lrev

<400> SEQUENCE: 30

```
cattcccatc cactccagac cctttcctgg agg                                    33
```

<210> SEQ ID NO 31
<211> LENGTH: 27
<212> TYPE: DNA
<213> ORGANISM: Artificial
<220> FEATURE:
<223> OTHER INFORMATION: Primer - Mutagenic oligonucleotide M48L

<400> SEQUENCE: 31

```
gggtccggag tggctgggaa tgatgtg                                           27
```

<210> SEQ ID NO 32
<211> LENGTH: 27
<212> TYPE: DNA
<213> ORGANISM: Artificial
<220> FEATURE:

<223> OTHER INFORMATION: Primer - Mutagenic oligonucleotide M48Lrev

<400> SEQUENCE: 32
cacatcattc ccagccactc cggaccc                                27

<210> SEQ ID NO 33
<211> LENGTH: 47
<212> TYPE: DNA
<213> ORGANISM: Artificial
<220> FEATURE:
<223> OTHER INFORMATION: Primer - Mutagenic oligonucleotide STS60NSA

<400> SEQUENCE: 33
gtggtggttc cacagactat aattcagctc tcaaatccag actgacc          47

<210> SEQ ID NO 34
<211> LENGTH: 47
<212> TYPE: DNA
<213> ORGANISM: Artificial
<220> FEATURE:
<223> OTHER INFORMATION: Primer - Mutagenic oligonucleotide STS60NSArev

<400> SEQUENCE: 34
ggtcagtctg gatttgagag ctgaattata gtctgtggaa ccaccac          47

<210> SEQ ID NO 35
<211> LENGTH: 33
<212> TYPE: DNA
<213> ORGANISM: Artificial
<220> FEATURE:
<223> OTHER INFORMATION: Primer - Mutagenic oligonucleotide T68S

<400> SEQUENCE: 35
ctcaaatcca gactgagcat cagcaaggac acc                         33

<210> SEQ ID NO 36
<211> LENGTH: 33
<212> TYPE: DNA
<213> ORGANISM: Artificial
<220> FEATURE:
<223> OTHER INFORMATION: Primer - Mutagenic oligonucleotide T68Srev

<400> SEQUENCE: 36
ggtgtccttg ctgatgctca gtctggattt gag                         33

<210> SEQ ID NO 37
<211> LENGTH: 41
<212> TYPE: DNA
<213> ORGANISM: Artificial
<220> FEATURE:
<223> OTHER INFORMATION: Primer - Mutagenic oligonucleotide S79F

<400> SEQUENCE: 37
cacctcgaag agccaggtct tcttaaaaat gaacagtctg c                41

<210> SEQ ID NO 38
<211> LENGTH: 41
<212> TYPE: DNA
<213> ORGANISM: Artificial
<220> FEATURE:
<223> OTHER INFORMATION: Primer - Mutagenic oligonucleotide S79Frev

<400> SEQUENCE: 38
gcagactgtt catttttaag aagacctggc tcttcgaggt g                41

<210> SEQ ID NO 39

```
<211> LENGTH: 27
<212> TYPE: DNA
<213> ORGANISM: Artificial
<220> FEATURE:
<223> OTHER INFORMATION: Primer - Mutagenic oligonucleotide T108S

<400> SEQUENCE: 39
gggtcaagga acctcggtca ccgtctc                                              27

<210> SEQ ID NO 40
<211> LENGTH: 27
<212> TYPE: DNA
<213> ORGANISM: Artificial
<220> FEATURE:
<223> OTHER INFORMATION: Primer - Mutagenic oligonucleotide T108Srev

<400> SEQUENCE: 40
gagacggtga ccgaggttcc ttgaccc                                              27

<210> SEQ ID NO 41
<211> LENGTH: 41
<212> TYPE: DNA
<213> ORGANISM: Artificial
<220> FEATURE:
<223> OTHER INFORMATION: I29V primer

<400> SEQUENCE: 41
gcactgtctc tgggttctca gtctctagat atagtgtata c                              41

<210> SEQ ID NO 42
<211> LENGTH: 41
<212> TYPE: DNA
<213> ORGANISM: Artificial
<220> FEATURE:
<223> OTHER INFORMATION: I29Vrev primer

<400> SEQUENCE: 42
gtatacacta tatctagaga ctgagaaccc agagacagtg c                              41

<210> SEQ ID NO 43
<211> LENGTH: 34
<212> TYPE: DNA
<213> ORGANISM: Artificial
<220> FEATURE:
<223> OTHER INFORMATION: I37L primer

<400> SEQUENCE: 43
gatatagtgt atactggctg cgccagcctc cagg                                      34

<210> SEQ ID NO 44
<211> LENGTH: 34
<212> TYPE: DNA
<213> ORGANISM: Artificial
<220> FEATURE:
<223> OTHER INFORMATION: I37Lrev primer

<400> SEQUENCE: 44
cctggaggct ggcgcagcca gtatacacta tatc                                      34

<210> SEQ ID NO 45
<211> LENGTH: 339
<212> TYPE: DNA
<213> ORGANISM: Artificial
<220> FEATURE:
<223> OTHER INFORMATION: Murine 5D12 VH region - Consensus DNA
<220> FEATURE:
<221> NAME/KEY: CDS
<222> LOCATION: (1)..(339)
```

<223> OTHER INFORMATION: Mu5D12 VH region

<400> SEQUENCE: 45

```
cag gtc aag ctc gag gag tct gga cct ggc ctg gtg gca ccc tca cag      48
Gln Val Lys Leu Glu Glu Ser Gly Pro Gly Leu Val Ala Pro Ser Gln
1               5                   10                  15 agc ctg tcc atc aca tgc act gtc tct ggg ttc tca tta tcc aga tat      96
Ser Leu Ser Ile Thr Cys Thr Val Ser Gly Phe Ser Leu Ser Arg Tyr
                20                  25                  30 agt gta tac tgg gtt cgc cag cct cca gga aag ggt ctg gag tgg ctg     144
Ser Val Tyr Trp Val Arg Gln Pro Pro Gly Lys Gly Leu Glu Trp Leu
            35                  40                  45 gga atg atg tgg ggt ggt gga tcc aca gac tat aat tca gct ctc aaa     192
Gly Met Met Trp Gly Gly Gly Ser Thr Asp Tyr Asn Ser Ala Leu Lys
        50                  55                  60 tcc aga ctg agc atc agc aag gac acc tcg aag agc cag gtc ttc tta     240
Ser Arg Leu Ser Ile Ser Lys Asp Thr Ser Lys Ser Gln Val Phe Leu
65                  70                  75                  80 aaa atg aac agt ctg cga act gat gac aca gcc atg tac tac tgt gtc     288
Lys Met Asn Ser Leu Arg Thr Asp Asp Thr Ala Met Tyr Tyr Cys Val
                85                  90                  95 aga acc gat ggg gac tac tgg ggt caa gga acc tca gtc acc gtc tcc     336
Arg Thr Asp Gly Asp Tyr Trp Gly Gln Gly Thr Ser Val Thr Val Ser
                100                 105                 110 tca                                                                  339
Ser
```

<210> SEQ ID NO 46
<211> LENGTH: 113
<212> TYPE: PRT
<213> ORGANISM: Artificial
<220> FEATURE:
<223> OTHER INFORMATION: Synthetic Construct

<400> SEQUENCE: 46

```
Gln Val Lys Leu Glu Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
                20                  25                  30

Ser Val Tyr Trp Val Arg Gln Pro Pro Gly Lys Gly Leu Glu Trp Leu
            35                  40                  45

Gly Met Met Trp Gly Gly Gly Ser Thr Asp Tyr Asn Ser Ala Leu Lys
        50                  55                  60

Ser Arg Leu Ser Ile Ser Lys Asp Thr Ser Lys Ser Gln Val Phe Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Ser Val Thr Val Ser
                100                 105                 110

Ser
```

<210> SEQ ID NO 47
<211> LENGTH: 339
<212> TYPE: DNA
<213> ORGANISM: Artificial
<220> FEATURE:
<223> OTHER INFORMATION: Murine 5D12 VL region - consensus DNA
<220> FEATURE:
<221> NAME/KEY: CDS
<222> LOCATION: (1)..(339)
<223> OTHER INFORMATION: Mu5D12 VL region

```
<400> SEQUENCE: 47 gag ctc cag ctg acc cag tct cca ctc tcc ctg cct gtc agt ctt gga      48
Glu Leu Gln Leu Thr Gln Ser Pro Leu Ser Leu Pro Val Ser Leu Gly
1               5                   10                  15 gat caa gcc tcc atc tct tgc aga tct agt cag agc ctt gta aac agt      96
Asp Gln Ala Ser Ile Ser Cys Arg Ser Ser Gln Ser Leu Val Asn Ser
            20                  25                  30 aat gga aac acc tat tta cat tgg tac ctg cag aag cca ggc cag tct     144
Asn Gly Asn Thr Tyr Leu His Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag att     240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt     288
Ser Arg Val Glu Ala Glu Asp Leu Gly Val Tyr Phe Cys Ser Gln Ser
                85                  90                  95 aca cat gtt ccg tgg acg ttc ggt gga ggc acc aag ctg gaa atc aaa     336
Thr His Val Pro Trp Thr Phe Gly Gly Gly Thr Lys Leu Glu Ile Lys
            100                 105                 110 cgt                                                                 339
Arg

<210> SEQ ID NO 48
<211> LENGTH: 113
<212> TYPE: PRT
<213> ORGANISM: Artificial
<220> FEATURE:
<223> OTHER INFORMATION: Synthetic Construct

<400> SEQUENCE: 48

Glu Leu Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val Asn Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg

<210> SEQ ID NO 49
<211> LENGTH: 113
<212> TYPE: PRT
<213> ORGANISM: Artificial
<220> FEATURE:
<223> OTHER INFORMATION: Murine V region with veneered and de-immunised
      V regions of 5D12 - 5d12mvh

<400> SEQUENCE: 49

Gln Val Lys Leu Glu Glu Ser Gly Pro Gly Leu Val Ala Pro Ser Gln
1               5                   10                  15
```

-continued

Ser Leu Ser Ile Thr Cys Thr Val Ser Gly Phe Ser Leu Ser Arg Tyr
            20                  25                  30

Ser Val Tyr Trp Val Arg Gln Pro Pro Gly Lys Gly Leu Glu Trp Leu
        35                  40                  45

Gly Met Met Trp Gly Gly Gly Ser Thr Asp Tyr Asn Ser Ala Leu Lys
50                      55                  60

Ser Arg Leu Ser Ile Ser Lys Asp Thr Ser Lys Ser Gln Val Phe Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Ser Val Thr Val Ser
            100                 105                 110

Ser

<210> SEQ ID NO 50
<211> LENGTH: 113
<212> TYPE: PRT
<213> ORGANISM: Artificial
<220> FEATURE:
<223> OTHER INFORMATION: Murine V region with veneered and de-immunised
      V regions of 5D12 - 5d12divh

<400> SEQUENCE: 50

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
50                      55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 51
<211> LENGTH: 113
<212> TYPE: PRT
<213> ORGANISM: Artificial
<220> FEATURE:
<223> OTHER INFORMATION: Murine V region with veneered and de-immunised
      V regions of 5D12 - 5d12mvkl

<400> SEQUENCE: 51

Glu Leu Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val Asn Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                      55                  60

Asp Arg Phe Ser Gly Ser Gly Ser Gly Thr Asp Phe Thr Leu Lys Ile
65                  70                  75                  80

```
Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg

<210> SEQ ID NO 52
<211> LENGTH: 113
<212> TYPE: PRT
<213> ORGANISM: Artificial
<220> FEATURE:
<223> OTHER INFORMATION: Murine V region with veneered and de-immunised
      V regions of 5D12 - 5d12divkl

<400> SEQUENCE: 52

Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Asn Ser
            20                  25                  30

Asn Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg

<210> SEQ ID NO 53
<211> LENGTH: 113
<212> TYPE: PRT
<213> ORGANISM: Artificial
<220> FEATURE:
<223> OTHER INFORMATION: Amino acid variant Q5E

<400> SEQUENCE: 53

Gln Val Lys Leu Glu Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Ser Leu Lys
50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 54
<211> LENGTH: 113
<212> TYPE: PRT
<213> ORGANISM: Artificial
```

<220> FEATURE:
<223> OTHER INFORMATION: Amino acid variant K13A

<400> SEQUENCE: 54

Gln Val Lys Leu Gln Glu Ser Gly Pro Gly Leu Val Ala Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 55
<211> LENGTH: 113
<212> TYPE: PRT
<213> ORGANISM: Artificial
<220> FEATURE:
<223> OTHER INFORMATION: Amino acid variant E16Q

<400> SEQUENCE: 55

Gln Val Lys Leu Gln Glu Ser Gly Pro Gly Leu Val Lys Pro Ser Gln
1               5                   10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 56
<211> LENGTH: 113
<212> TYPE: PRT
<213> ORGANISM: Artificial
<220> FEATURE:
<223> OTHER INFORMATION: Amino acid variant T17S

<400> SEQUENCE: 56

Gln Val Lys Leu Gln Glu Ser Gly Pro Gly Leu Val Lys Pro Ser Glu
1               5                   10                  15

Ser Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
            50                  55                  60

Ser Arg Leu Thr Ile Ser Lys Asp Thr Ser Lys Ser Gln Val Ser Leu
65                      70                  75                  80

Lys Met Asn Ser Leu Arg Thr Asp Asp Thr Ala Met Tyr Tyr Cys Val
                    85                  90                  95

Arg Thr Asp Gly Asp Tyr Trp Gly Gln Gly Thr Thr Val Thr Val Ser
                100                 105                 110

Ser

<210> SEQ ID NO 57
<211> LENGTH: 113
<212> TYPE: PRT
<213> ORGANISM: Artificial
<220> FEATURE:
<223> OTHER INFORMATION: Amino acid variant I29L

<400> SEQUENCE: 57

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
                20                  25                  30

Ser Val Tyr Trp Ile Arg Gln Pro Pro Gly Lys Gly Pro Glu Trp Met
            35                  40                  45

Gly Met Met Trp Gly Gly Gly Ser Thr Asp Tyr Ser Thr Ser Leu Lys
            50                  55                  60

Ser Arg Leu Thr Ile Ser Lys Asp Thr Ser Lys Ser Gln Val Ser Leu
65                      70                  75                  80

Lys Met Asn Ser Leu Arg Thr Asp Asp Thr Ala Met Tyr Tyr Cys Val
                    85                  90                  95

Arg Thr Asp Gly Asp Tyr Trp Gly Gln Gly Thr Thr Val Thr Val Ser
                100                 105                 110

Ser

<210> SEQ ID NO 58
<211> LENGTH: 113
<212> TYPE: PRT
<213> ORGANISM: Artificial
<220> FEATURE:
<223> OTHER INFORMATION: Amino acid variant I37V

<400> SEQUENCE: 58

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
                20                  25                  30

Ser Val Tyr Trp Val Arg Gln Pro Pro Gly Lys Gly Pro Glu Trp Met
            35                  40                  45

Gly Met Met Trp Gly Gly Gly Ser Thr Asp Tyr Ser Thr Ser Leu Lys
            50                  55                  60

Ser Arg Leu Thr Ile Ser Lys Asp Thr Ser Lys Ser Gln Val Ser Leu
65                      70                  75                  80

Lys Met Asn Ser Leu Arg Thr Asp Asp Thr Ala Met Tyr Tyr Cys Val
                    85                  90                  95

Arg Thr Asp Gly Asp Tyr Trp Gly Gln Gly Thr Thr Val Thr Val Ser
                100                 105                 110

Ser

-continued

```
<210> SEQ ID NO 59
<211> LENGTH: 113
<212> TYPE: PRT
<213> ORGANISM: Artificial
<220> FEATURE:
<223> OTHER INFORMATION: Amino acid variant P45L

<400> SEQUENCE: 59

Gln Val Lys Leu Gln Glu Ser Gly Pro Gly Leu Val Lys Pro Ser Glu
 1               5                  10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Leu Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 60
<211> LENGTH: 113
<212> TYPE: PRT
<213> ORGANISM: Artificial
<220> FEATURE:
<223> OTHER INFORMATION: Amino acid variant M48L

<400> SEQUENCE: 60

Gln Val Lys Leu Gln Glu Ser Gly Pro Gly Leu Val Lys Pro Ser Glu
 1               5                  10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Leu
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 61
<211> LENGTH: 113
<212> TYPE: PRT
<213> ORGANISM: Artificial
<220> FEATURE:
<223> OTHER INFORMATION: Amino acid variant STS60NSA

<400> SEQUENCE: 61

Gln Val Lys Leu Gln Glu Ser Gly Pro Gly Leu Val Lys Pro Ser Glu
 1               5                  10                  15

Thr Leu Ser Ile Thr Cys Thr Val Ser Gly Phe Ser Ile Ser Arg Tyr
```

-continued

```
                    20                  25                  30
Ser Val Tyr Trp Ile Arg Gln Pro Pro Gly Lys Gly Pro Glu Trp Met
                35                  40                  45

Gly Met Met Trp Gly Gly Gly Ser Thr Asp Tyr Asn Ser Ala Leu Lys
 50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Thr Ala Met Tyr Tyr Cys Val
                85                  90                  95

Arg Thr Asp Gly Asp Tyr Trp Gly Gln Gly Thr Thr Val Thr Val Ser
                100                 105                 110

Ser

<210> SEQ ID NO 62
<211> LENGTH: 113
<212> TYPE: PRT
<213> ORGANISM: Artificial
<220> FEATURE:
<223> OTHER INFORMATION: Amino acid variant T68S

<400> SEQUENCE: 62

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
                20                  25                  30

Ser Val Tyr Trp Ile Arg Gln Pro Pro Gly Lys Gly Pro Glu Trp Met
                35                  40                  45

Gly Met Met Trp Gly Gly Gly Ser Thr Asp Tyr Ser Thr Ser Leu Lys
 50                  55                  60

Ser Arg Leu Ser Ile Ser Lys Asp Thr Ser Lys Ser Gln Val Ser Leu
65                  70                  75                  80

Lys Met Asn Ser Leu Arg Thr Asp Thr Ala Met Tyr Tyr Cys Val
                85                  90                  95

Arg Thr Asp Gly Asp Tyr Trp Gly Gln Gly Thr Thr Val Thr Val Ser
                100                 105                 110

Ser

<210> SEQ ID NO 63
<211> LENGTH: 113
<212> TYPE: PRT
<213> ORGANISM: Artificial
<220> FEATURE:
<223> OTHER INFORMATION: Amino acid variant S79F

<400> SEQUENCE: 63

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
                20                  25                  30

Ser Val Tyr Trp Ile Arg Gln Pro Pro Gly Lys Gly Pro Glu Trp Met
                35                  40                  45

Gly Met Met Trp Gly Gly Gly Ser Thr Asp Tyr Ser Thr Ser Leu Lys
 50                  55                  60

Ser Arg Leu Thr Ile Ser Lys Asp Thr Ser Lys Ser Gln Val Phe Leu
65                  70                  75                  80

Lys Met Asn Ser Leu Arg Thr Asp Thr Ala Met Tyr Tyr Cys Val
                85                  90                  95
```

Arg Thr Asp Gly Asp Tyr Trp Gly Gln Gly Thr Thr Val Thr Val Ser
                100                 105                 110
Ser

<210> SEQ ID NO 64
<211> LENGTH: 113
<212> TYPE: PRT
<213> ORGANISM: Artificial
<220> FEATURE:
<223> OTHER INFORMATION: Amino acid variant T108S

<400> SEQUENCE: 64

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Ser Val Thr Val Ser
                100                 105                 110
Ser

<210> SEQ ID NO 65
<211> LENGTH: 113
<212> TYPE: PRT
<213> ORGANISM: Artificial
<220> FEATURE:
<223> OTHER INFORMATION: Parent murine sequence ch5D12

<400> SEQUENCE: 65

Gln Val Lys Leu Glu Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val Tyr Trp Val Arg Gln Pro Pro Gly Lys Gly Leu Glu Trp Leu
        35                  40                  45

Gly Met Met Trp Gly Gly Gly Ser Thr Asp Tyr Asn Ser Ala Leu Lys
    50                  55                  60

Ser Arg Leu Ser Ile Ser Lys Asp Thr Ser Lys Ser Gln Val Phe Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Ser Val Thr Val Ser
                100                 105                 110
Ser

<210> SEQ ID NO 66
<211> LENGTH: 113
<212> TYPE: PRT
<213> ORGANISM: Artificial
<220> FEATURE:
<223> OTHER INFORMATION: Parent murine sequence DI5D12

<400> SEQUENCE: 66

```
Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Ser Thr Asp Tyr Ser Thr Ser Leu Lys
50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 67
<211> LENGTH: 113
<212> TYPE: PRT
<213> ORGANISM: Artificial
<220> FEATURE:
<223> OTHER INFORMATION: Amino acid variant IV

<400> SEQUENCE: 67

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Val Arg Gln Pro Pro Gly Lys Gly Pro Glu Trp Met
        35                  40                  45

Gly Met Met Trp Gly Gly Ser Thr Asp Tyr Ser Thr Ser Leu Lys
50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 68
<211> LENGTH: 113
<212> TYPE: PRT
<213> ORGANISM: Artificial
<220> FEATURE:
<223> OTHER INFORMATION: Amino acid variant VI

<400> SEQUENCE: 68

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Val Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Ser Thr Asp Tyr Ser Thr Ser Leu Lys
50                  55                  60

Ser Arg Leu Thr Ile Ser Lys Asp Thr Ser Lys Ser Gln Val Ser Leu
```

```
                65                  70                  75                  80
Lys Met Asn Ser Leu Arg Thr Asp Asp Thr Ala Met Tyr Tyr Cys Val
                    85                  90                  95
Arg Thr Asp Gly Asp Tyr Trp Gly Gln Gly Thr Thr Val Thr Val Ser
                100                 105                 110
Ser

<210> SEQ ID NO 69
<211> LENGTH: 113
<212> TYPE: PRT
<213> ORGANISM: Artificial
<220> FEATURE:
<223> OTHER INFORMATION: Amino acid variant IL

<400> SEQUENCE: 69

Gln Val Lys Leu Gln Glu Ser Gly Pro Gly Leu Val Lys Pro Ser Glu
1               5                   10                  15
Thr Leu Ser Ile Thr Cys Thr Val Ser Gly Phe Ser Ile Ser Arg Tyr
                20                  25                  30
Ser Val Tyr Trp Leu Arg Gln Pro Pro Gly Lys Gly Pro Glu Trp Met
            35                  40                  45
Gly Met Met Trp Gly Gly Gly Ser Thr Asp Tyr Ser Thr Ser Leu Lys
        50                  55                  60
Ser Arg Leu Thr Ile Ser Lys Asp Thr Ser Lys Ser Gln Val Ser Leu
65                  70                  75                  80
Lys Met Asn Ser Leu Arg Thr Asp Asp Thr Ala Met Tyr Tyr Cys Val
                    85                  90                  95
Arg Thr Asp Gly Asp Tyr Trp Gly Gln Gly Thr Thr Val Thr Val Ser
                100                 105                 110
Ser

<210> SEQ ID NO 70
<211> LENGTH: 113
<212> TYPE: PRT
<213> ORGANISM: Artificial
<220> FEATURE:
<223> OTHER INFORMATION: Amino acid variant VV

<400> SEQUENCE: 70

Gln Val Lys Leu Gln Glu Ser Gly Pro Gly Leu Val Lys Pro Ser Glu
1               5                   10                  15
Thr Leu Ser Ile Thr Cys Thr Val Ser Gly Phe Ser Val Ser Arg Tyr
                20                  25                  30
Ser Val Tyr Trp Val Arg Gln Pro Pro Gly Lys Gly Pro Glu Trp Met
            35                  40                  45
Gly Met Met Trp Gly Gly Gly Ser Thr Asp Tyr Ser Thr Ser Leu Lys
        50                  55                  60
Ser Arg Leu Thr Ile Ser Lys Asp Thr Ser Lys Ser Gln Val Ser Leu
65                  70                  75                  80
Lys Met Asn Ser Leu Arg Thr Asp Asp Thr Ala Met Tyr Tyr Cys Val
                    85                  90                  95
Arg Thr Asp Gly Asp Tyr Trp Gly Gln Gly Thr Thr Val Thr Val Ser
                100                 105                 110
Ser

<210> SEQ ID NO 71
<211> LENGTH: 113
<212> TYPE: PRT
```

<213> ORGANISM: Artificial
<220> FEATURE:
<223> OTHER INFORMATION: Amino acid variant LL

<400> SEQUENCE: 71

```
Gln Val Lys Leu Gln Glu Ser Gly Pro Gly Leu Val Lys Pro Ser Glu
  1               5                  10                  15

Thr Leu Ser Ile Thr Cys Thr Val Ser Gly Phe Ser Leu Ser Arg Tyr
             20                  25                  30

Ser Val Tyr Trp Leu Arg Gln Pro Pro Gly Lys Gly Pro Glu Trp Met
         35                  40                  45

Gly Met Met Trp Gly Gly Ser Thr Asp Tyr Ser Thr Ser Leu Lys
     50                  55                  60

Ser Arg Leu Thr Ile Ser Lys Asp Thr Ser Lys Ser Gln Val Ser Leu
 65                  70                  75                  80

Lys Met Asn Ser Leu Arg Thr Asp Asp Thr Ala Met Tyr Tyr Cys Val
                 85                  90                  95

Arg Thr Asp Gly Asp Tyr Trp Gly Gln Gly Thr Thr Val Thr Val Ser
                100                 105                 110

Ser
```

<210> SEQ ID NO 72
<211> LENGTH: 113
<212> TYPE: PRT
<213> ORGANISM: Artificial
<220> FEATURE:
<223> OTHER INFORMATION: Amino acid variant VL

<400> SEQUENCE: 72

```
Gln Val Lys Leu Gln Glu Ser Gly Pro Gly Leu Val Lys Pro Ser Glu
  1               5                  10                  15

Thr Leu Ser Ile Thr Cys Thr Val Ser Gly Phe Ser Val Ser Arg Tyr
             20                  25                  30

Ser Val Tyr Trp Leu Arg Gln Pro Pro Gly Lys Gly Pro Glu Trp Met
         35                  40                  45

Gly Met Met Trp Gly Gly Ser Thr Asp Tyr Ser Thr Ser Leu Lys
     50                  55                  60

Ser Arg Leu Thr Ile Ser Lys Asp Thr Ser Lys Ser Gln Val Ser Leu
 65                  70                  75                  80

Lys Met Asn Ser Leu Arg Thr Asp Asp Thr Ala Met Tyr Tyr Cys Val
                 85                  90                  95

Arg Thr Asp Gly Asp Tyr Trp Gly Gln Gly Thr Thr Val Thr Val Ser
                100                 105                 110

Ser
```

<210> SEQ ID NO 73
<211> LENGTH: 113
<212> TYPE: PRT
<213> ORGANISM: Artificial
<220> FEATURE:
<223> OTHER INFORMATION: Amino acid variant LV

<400> SEQUENCE: 73

```
Gln Val Lys Leu Gln Glu Ser Gly Pro Gly Leu Val Lys Pro Ser Glu
  1               5                  10                  15

Thr Leu Ser Ile Thr Cys Thr Val Ser Gly Phe Ser Leu Ser Arg Tyr
             20                  25                  30

Ser Val Tyr Trp Val Arg Gln Pro Pro Gly Lys Gly Pro Glu Trp Met
         35                  40                  45
```

```
Gly Met Met Trp Gly Gly Gly Ser Thr Asp Tyr Ser Thr Ser Leu Lys
         50                  55                  60
Ser Arg Leu Thr Ile Ser Lys Asp Thr Ser Lys Ser Gln Val Ser Leu
 65                  70                  75                  80
Lys Met Asn Ser Leu Arg Thr Asp Thr Ala Met Tyr Tyr Cys Val
                 85                  90                  95
Arg Thr Asp Gly Asp Tyr Trp Gly Gln Gly Thr Thr Val Thr Val Ser
                100                 105                 110
Ser
```

<210> SEQ ID NO 74
<211> LENGTH: 113
<212> TYPE: PRT
<213> ORGANISM: Artificial
<220> FEATURE:
<223> OTHER INFORMATION: CH5D12 (PG100)

<400> SEQUENCE: 74

```
Gln Val Lys Leu Glu Glu Ser Gly Pro Gly Leu Val Ala Pro Ser Gln
 1               5                  10                  15
Ser Leu Ser Ile Thr Cys Thr Val Ser Gly Phe Ser Leu Ser Arg Tyr
                 20                  25                  30
Ser Val Tyr Trp Val Arg Gln Pro Pro Gly Lys Gly Leu Glu Trp Leu
                 35                  40                  45
Gly Met Met Trp Gly Gly Gly Ser Thr Asp Tyr Asn Ser Ala Leu Lys
         50                  55                  60
Ser Arg Leu Ser Ile Ser Lys Asp Thr Ser Lys Ser Gln Val Phe Leu
 65                  70                  75                  80
Lys Met Asn Ser Leu Arg Thr Asp Thr Ala Met Tyr Tyr Cys Val
                 85                  90                  95
Arg Thr Asp Gly Asp Tyr Trp Gly Gln Gly Thr Ser Val Thr Val Ser
                100                 105                 110
Ser
```

<210> SEQ ID NO 75
<211> LENGTH: 113
<212> TYPE: PRT
<213> ORGANISM: Artificial
<220> FEATURE:
<223> OTHER INFORMATION: DI5D12 (II)

<400> SEQUENCE: 75

```
Gln Val Lys Leu Gln Glu Ser Gly Pro Gly Leu Val Lys Pro Ser Glu
 1               5                  10                  15
Thr Leu Ser Ile Thr Cys Thr Val Ser Gly Phe Ser Ile Ser Arg Tyr
                 20                  25                  30
Ser Val Tyr Trp Ile Arg Gln Pro Pro Gly Lys Gly Pro Glu Trp Met
                 35                  40                  45
Gly Met Met Trp Gly Gly Gly Ser Thr Asp Tyr Ser Thr Ser Leu Lys
         50                  55                  60
Ser Arg Leu Thr Ile Ser Lys Asp Thr Ser Lys Ser Gln Val Ser Leu
 65                  70                  75                  80
Lys Met Asn Ser Leu Arg Thr Asp Thr Ala Met Tyr Tyr Cys Val
                 85                  90                  95
Arg Thr Asp Gly Asp Tyr Trp Gly Gln Gly Thr Thr Val Thr Val Ser
                100                 105                 110
Ser
```

<210> SEQ ID NO 76
<211> LENGTH: 113
<212> TYPE: PRT
<213> ORGANISM: Artificial
<220> FEATURE:
<223> OTHER INFORMATION: PG102 (LI)

<400> SEQUENCE: 76

```
Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser
```

<210> SEQ ID NO 77
<211> LENGTH: 1383
<212> TYPE: DNA
<213> ORGANISM: Artificial
<220> FEATURE:
<223> OTHER INFORMATION: PG102 HEAVY CHAIN
<220> FEATURE:
<221> NAME/KEY: CDS
<222> LOCATION: (1)..(1383)

<400> SEQUENCE: 77

```
atg gag tgg tct tgg gtg ttc ctg ttc ttc ctg tct gtg aca aca gga      48
Met Glu Trp Ser Trp Val Phe Leu Phe Phe Leu Ser Val Thr Thr Gly
1               5                   10                  15 gtg cac tct cag gtc aag ctg cag gag tct gga cca gga ctg gtg aag      96
Val His Ser Gln Val Lys Leu Gln Glu Ser Gly Pro Gly Leu Val Lys
            20                  25                  30 cca tct gag acc ctg agc atc acc tgt aca gtg agc ggc ttc agc ctc     144
Pro Ser Glu Thr Leu Ser Ile Thr Cys Thr Val Ser Gly Phe Ser Leu
        35                  40                  45 tct aga tac agc gtg tac tgg atc aga cag cca cct gga aag gga cca     192
Ser Arg Tyr Ser Val Tyr Trp Ile Arg Gln Pro Pro Gly Lys Gly Pro
    50                  55                  60 gag tgg atg gga atg atg tgg gga gga gga tct aca gac tac agc acc     240
Glu Trp Met Gly Met Met Trp Gly Gly Gly Ser Thr Asp Tyr Ser Thr
65                  70                  75                  80 agc ctg aag tct aga ctg acc atc agc aag gac acc tct aag tct cag     288
Ser Leu Lys Ser Arg Leu Thr Ile Ser Lys Asp Thr Ser Lys Ser Gln
                85                  90                  95 gtc tcc ctg aag atg aac tct ctg aga aca gac gac acc gcc atg tac     336
Val Ser Leu Lys Met Asn Ser Leu Arg Thr Asp Asp Thr Ala Met Tyr
            100                 105                 110 tac tgt gtg aga acc gac gga gat tat tgg gga cag ggc aca aca gtg     384
Tyr Cys Val Arg Thr Asp Gly Asp Tyr Trp Gly Gln Gly Thr Thr Val
        115                 120                 125 aca gtg tcc tct gcc tct aca aag gga cca tct gtg ttt cca ctg gcc     432
Thr Val Ser Ser Ala Ser Thr Lys Gly Pro Ser Val Phe Pro Leu Ala
```

```
                Thr Val Ser Ser Ala Ser Thr Lys Gly Pro Ser Val Phe Pro Leu Ala
                    130                 135                 140 cca tgt tct aga tct acc agc gag tct aca gct gct ctg gga tgt ctg          480
Pro Cys Ser Arg Ser Thr Ser Glu Ser Thr Ala Ala Leu Gly Cys Leu
145                 150                 155                 160 gtg aag gac tac ttt cca gag cct gtg aca gtg tct tgg aat agt gga          528
Val Lys Asp Tyr Phe Pro Glu Pro Val Thr Val Ser Trp Asn Ser Gly
                165                 170                 175 gcc ctg aca tct gga gtg cac aca ttt cca gct gtg ctg cag tct agc          576
Ala Leu Thr Ser Gly Val His Thr Phe Pro Ala Val Leu Gln Ser Ser
            180                 185                 190 gga ctg tat tct ctg tcc agc gtg gtg aca gtg cca tct tct tct ctg          624
Gly Leu Tyr Ser Leu Ser Ser Val Val Thr Val Pro Ser Ser Ser Leu
        195                 200                 205 ggc acc aag acc tac aca tgt aac gtg gac cac aag cca tct aac acc          672
Gly Thr Lys Thr Tyr Thr Cys Asn Val Asp His Lys Pro Ser Asn Thr
    210                 215                 220 aag gtg gac aag aga gtg gag tct aag tac gga cca cca tgc cca tct          720
Lys Val Asp Lys Arg Val Glu Ser Lys Tyr Gly Pro Pro Cys Pro Ser
225                 230                 235                 240 tgt cca gct cca gag ttt ctg gga gga cct agc gtg ttt ctg ttc ccc          768
Cys Pro Ala Pro Glu Phe Leu Gly Gly Pro Ser Val Phe Leu Phe Pro
                245                 250                 255 cca aag cca aag gat acc ctg atg atc tct aga acc cca gag gtg aca          816
Pro Lys Pro Lys Asp Thr Leu Met Ile Ser Arg Thr Pro Glu Val Thr
            260                 265                 270 tgt gtg gtg gtg gat gtg tct cag gag gat cca gag gtc cag ttt aac          864
Cys Val Val Val Asp Val Ser Gln Glu Asp Pro Glu Val Gln Phe Asn
        275                 280                 285 tgg tac gtg gat gga gtg gag gtg cac aac gct aag aca aag cca aga          912
Trp Tyr Val Asp Gly Val Glu Val His Asn Ala Lys Thr Lys Pro Arg
    290                 295                 300 gag gag cag ttc aac agc aca tac aga gtg gtg tct gtg ctg aca gtg          960
Glu Glu Gln Phe Asn Ser Thr Tyr Arg Val Val Ser Val Leu Thr Val
305                 310                 315                 320 ctg cat cag gat tgg ctg aac ggc aag gaa tac aag tgt aag gtc tcc         1008
Leu His Gln Asp Trp Leu Asn Gly Lys Glu Tyr Lys Cys Lys Val Ser
                325                 330                 335 aac aag ggc ctg cca tct tct atc gag aaa acc atc tct aag gct aag         1056
Asn Lys Gly Leu Pro Ser Ser Ile Glu Lys Thr Ile Ser Lys Ala Lys
            340                 345                 350 gga cag cca agg gag cca cag gtg tac aca ctg cca cca tct caa gag         1104
Gly Gln Pro Arg Glu Pro Gln Val Tyr Thr Leu Pro Pro Ser Gln Glu
        355                 360                 365 gag atg acc aag aac cag gtg tcc ctg aca tgc ctg gtg aag gga ttc         1152
Glu Met Thr Lys Asn Gln Val Ser Leu Thr Cys Leu Val Lys Gly Phe
    370                 375                 380 tac cca tct gat atc gct gtg gag tgg gag tct aat gga cag ccc gag         1200
Tyr Pro Ser Asp Ile Ala Val Glu Trp Glu Ser Asn Gly Gln Pro Glu
385                 390                 395                 400 aac aac tac aag acc aca cca cca gtg ctg gat tct gac ggc tct ttc         1248
Asn Asn Tyr Lys Thr Thr Pro Pro Val Leu Asp Ser Asp Gly Ser Phe
                405                 410                 415 ttc ctg tac agc aga ctg aca gtg gac aag tct aga tgg cag gag gga         1296
Phe Leu Tyr Ser Arg Leu Thr Val Asp Lys Ser Arg Trp Gln Glu Gly
            420                 425                 430 aac gtc ttt agc tgt agc gtg atg cat gag gct ctg cac aac cac tac         1344
Asn Val Phe Ser Cys Ser Val Met His Glu Ala Leu His Asn His Tyr
        435                 440                 445 acc cag aag tct ctg tct ctg agt ctg gga aaa tga tag                     1383
Thr Gln Lys Ser Leu Ser Leu Ser Leu Gly Lys
```

Thr Gln Lys Ser Leu Ser Leu Ser Leu Gly Lys
            450                 455

<210> SEQ ID NO 78
<211> LENGTH: 459
<212> TYPE: PRT
<213> ORGANISM: Artificial
<220> FEATURE:
<223> OTHER INFORMATION: Synthetic Construct

<400> SEQUENCE: 78

Met Glu Trp Ser Trp Val Phe Leu Phe Phe Leu Ser Val Thr Thr Gly
1               5                   10                  15

Val His Ser Gln Val Lys Leu Gln Glu Ser Gly Pro Gly Leu Val Lys
            20                  25                  30

Pro Ser Glu Thr Leu Ser Ile Thr Cys Thr Val Ser Gly Phe Ser Leu
        35                  40                  45

Ser Arg Tyr Ser Val Tyr Trp Ile Arg Gln Pro Pro Gly Lys Gly Pro
    50                  55                  60

Glu Trp Met Gly Met Met Trp Gly Gly Ser Thr Asp Tyr Ser Thr Ser
65                  70                  75                  80

Ser Leu Lys Ser Arg Leu Thr Ile Ser Lys Asp Thr Ser Lys Ser Gln
                85                  90                  95

Val Ser Leu Lys Met Asn Ser Leu Arg Thr Asp Asp Thr Ala Met Tyr
            100                 105                 110

Tyr Cys Val Arg Thr Asp Gly Asp Tyr Trp Gly Gln Gly Thr Thr Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Ser
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu

```
                      355                 360                 365
Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
                420                 425                 430

Asn Val Phe Ser Cys Ser Val Met His Glu Ala Leu His Asn His Tyr
                435                 440                 445

Thr Gln Lys Ser Leu Ser Leu Ser Leu Gly Lys
    450                 455

<210> SEQ ID NO 79
<211> LENGTH: 723
<212> TYPE: DNA
<213> ORGANISM: Artificial
<220> FEATURE:
<223> OTHER INFORMATION: PG102 LIGHT CHAIN
<220> FEATURE:
<221> NAME/KEY: CDS
<222> LOCATION: (1)..(723)

<400> SEQUENCE: 79 atg tct gtg cca aca cag gtg ctg gga ctg ctg ctg tgg ctg aca         48
Met Ser Val Pro Thr Gln Val Leu Gly Leu Leu Leu Trp Leu Thr
1               5                   10                  15 gat gct aga tgt gag ctg cag ctg aca cag tct cca ctg tct ctg cca    96
Asp Ala Arg Cys Glu Leu Gln Leu Thr Gln Ser Pro Leu Ser Leu Pro
                20                  25                  30 gtg aca ctg gga cag cca gct agc atc agc tgt aga agc tct cag tct   144
Val Thr Leu Gly Gln Pro Ala Ser Ile Ser Cys Arg Ser Ser Gln Ser
            35                  40                  45 ctg gcc aac tct aac ggc aac aca tac ctg cat tgg tat ctg cag aga   192
Leu Ala Asn Ser Asn Gly Asn Thr Tyr Leu His Trp Tyr Leu Gln Arg
        50                  55                  60 cca gga cag tct cca aga ctg ctg atc tac aag gtg tcc aac aga ttc   240
Pro Gly Gln Ser Pro Arg Leu Leu Ile Tyr Lys Val Ser Asn Arg Phe
65                  70                  75                  80 tct gga gtg cca gac aga ttt tct ggc tct ggc tct gga aca gac ttc   288
Ser Gly Val Pro Asp Arg Phe Ser Gly Ser Gly Ser Gly Thr Asp Phe
                85                  90                  95 acc ctg aag atc tct aga gtg gag gct gag gat gtg gga gtg tac tac   336
Thr Leu Lys Ile Ser Arg Val Glu Ala Glu Asp Val Gly Val Tyr Tyr
                100                 105                 110 tgc tct cag tct aca cat gtg cca tgg aca ttc gga gga gga aca aag   384
Cys Ser Gln Ser Thr His Val Pro Trp Thr Phe Gly Gly Gly Thr Lys
            115                 120                 125 ctg gag atc aag aga aca gtg gct gcc cca tct gtg ttt atc ttc ccc   432
Leu Glu Ile Lys Arg Thr Val Ala Ala Pro Ser Val Phe Ile Phe Pro
        130                 135                 140 cca tct gat gag cag ctg aag tct gga aca gct tct gtg gtg tgt ctg   480
Pro Ser Asp Glu Gln Leu Lys Ser Gly Thr Ala Ser Val Val Cys Leu
145                 150                 155                 160 ctg aac aac ttc tac cca agg gag gct aag gtg cag tgg aag gtg gac   528
Leu Asn Asn Phe Tyr Pro Arg Glu Ala Lys Val Gln Trp Lys Val Asp
                165                 170                 175 aat gct ctg cag tct gga aac tct cag gag tct gtc aca gag cag gac   576
Asn Ala Leu Gln Ser Gly Asn Ser Gln Glu Ser Val Thr Glu Gln Asp
                180                 185                 190
```

```
agc aag gac tct acc tac tct ctg agc agc aca ctg aca ctg tct aag      624
Ser Lys Asp Ser Thr Tyr Ser Leu Ser Ser Thr Leu Thr Leu Ser Lys
        195                 200                 205 gcc gac tac gag aag cat aag gtg tac gcc tgt gag gtg aca cat cag      672
Ala Asp Tyr Glu Lys His Lys Val Tyr Ala Cys Glu Val Thr His Gln
210                 215                 220 gga ctg tct agc cca gtg acc aag tct ttc aac aga ggc gag tgc tga      720
Gly Leu Ser Ser Pro Val Thr Lys Ser Phe Asn Arg Gly Glu Cys
225                 230                 235 tag                                                                   723

<210> SEQ ID NO 80
<211> LENGTH: 239
<212> TYPE: PRT
<213> ORGANISM: Artificial
<220> FEATURE:
<223> OTHER INFORMATION: Synthetic Construct

<400> SEQUENCE: 80

Met Ser Val Pro Thr Gln Val Leu Gly Leu Leu Leu Leu Trp Leu Thr
1               5                   10                  15

Asp Ala Arg Cys Glu Leu Gln Leu Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Ala Asn Ser Asn Gly Asn Thr Tyr Leu His Trp Tyr Leu Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 81
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
```

```
<223> OTHER INFORMATION: Xaa is Glycine, Alanine, Valine, Leucine,
      Proline, Phenylalanine or Methionine
<220> FEATURE:
<221> NAME/KEY: VARIANT
<222> LOCATION: (12)..(12)
<223> OTHER INFORMATION: Xaa is Glycine, Alanine, Valine, Leucine,
      Isoleucine, Proline, Phenylalanine or Methionine
<220> FEATURE:
<221> NAME/KEY: VARIANT
<222> LOCATION: (20)..(20)
<223> OTHER INFORMATION: Xaa is Glycine, Alanine, Valine, Leucine,
      Isoleucine, Proline, Phenylalanine or Methionine
<220> FEATURE:
<221> NAME/KEY: VARIANT
<222> LOCATION: (23)..(23)
<223> OTHER INFORMATION: Xaa is Glycine, Alanine, Valine, Leucine,
      Isoleucine, Proline, Phenylalanine or Methionine
<220> FEATURE:
<221> NAME/KEY: VARIANT
<222> LOCATION: (54)..(54)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine or Tyrosine

<400> SEQUENCE: 81

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Gly Ser Thr
            20                  25                  30

Asp Tyr Ser Thr Ser Leu Lys Ser Arg Leu Thr Ile Ser Lys Asp Thr
        35                  40                  45

Ser Lys Ser Gln Val Xaa Leu Lys Met Asn Ser Leu Arg Thr Asp Asp
    50                  55                  60

Thr Ala Met Tyr Tyr Cys Val Arg Thr Asp Gly Asp Tyr
65                  70                  75

<210> SEQ ID NO 82
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Glycine, Alanine, Valine, Leucine,
      Proline, Phenylalanine, Methionine, Tryptophan, Cysteine,
      Asparagine, Glutamine, Serine, Threonine, Tyrosine, Aspartic acid,
      Glutamic acid, Lysine, Arginine or Histidine
<220> FEATURE:
<221> NAME/KEY: VARIANT
<222> LOCATION: (12)..(12)
<223> OTHER INFORMATION: Xaa is Glycine, Alanine, Valine, Leucine,
      Proline, Phenylalanine, Methionine, Tryptophan, Cysteine,
      Asparagine, Glutamine, Serine, Threonine, Tyrosine, Aspartic acid,
      Glutamic acid, Lysine, Arginine or Histidine
<220> FEATURE:
<221> NAME/KEY: VARIANT
<222> LOCATION: (20)..(20)
<223> OTHER INFORMATION: Xaa is Glycine, Alanine, Valine, Leucine,
      Proline, Phenylalanine, Methionine, Tryptophan, Cysteine,
      Asparagine, Glutamine, Serine, Threonine, Tyrosine, Aspartic acid,
      Glutamic acid, Lysine, Arginine or Histidine
<220> FEATURE:
<221> NAME/KEY: VARIANT
<222> LOCATION: (23)..(23)
<223> OTHER INFORMATION: Xaa is Glycine, Alanine, Valine, Leucine,
      Proline, Phenylalanine, Methionine, Tryptophan, Cysteine,
      Asparagine, Glutamine, Serine, Threonine, Tyrosine, Aspartic acid,
      Glutamic acid, Lysine, Arginine or Histidine
<220> FEATURE:
<221> NAME/KEY: VARIANT
<222> LOCATION: (54)..(54)
<223> OTHER INFORMATION: Xaa is Glycine, Alanine, Valine, Leucine,
```

-continued

Proline, Phenylalanine, Methionine, Tryptophan, Cysteine,
Asparagine, Glutamine, Serine, Threonine, Tyrosine, Aspartic acid,
Glutamic acid, Lysine, Arginine or Histidine

<400> SEQUENCE: 82

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Gly Ser Thr
            20              25                  30

Asp Tyr Ser Thr Ser Leu Lys Ser Arg Leu Thr Ile Ser Lys Asp Thr
            35              40              45

Ser Lys Ser Gln Val Xaa Leu Lys Met Asn Ser Leu Arg Thr Asp Asp
    50              55                  60

Thr Ala Met Tyr Tyr Cys Val Arg Thr Asp Gly Asp Tyr
65              70                  75

<210> SEQ ID NO 83
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Leucine
<220> FEATURE:
<221> NAME/KEY: VARIANT
<222> LOCATION: (12)..(12)
<223> OTHER INFORMATION: Xaa is Isoleucine
<220> FEATURE:
<221> NAME/KEY: VARIANT
<222> LOCATION: (20)..(20)
<223> OTHER INFORMATION: Xaa is Proline
<220> FEATURE:
<221> NAME/KEY: VARIANT
<222> LOCATION: (23)..(23)
<223> OTHER INFORMATION: Xaa is Methionine
<220> FEATURE:
<221> NAME/KEY: VARIANT
<222> LOCATION: (54)..(54)
<223> OTHER INFORMATION: Xaa Serine

<400> SEQUENCE: 83

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Gly Ser Thr
            20              25                  30

Asp Tyr Ser Thr Ser Leu Lys Ser Arg Leu Thr Ile Ser Lys Asp Thr
            35              40              45

Ser Lys Ser Gln Val Xaa Leu Lys Met Asn Ser Leu Arg Thr Asp Asp
    50              55                  60

Thr Ala Met Tyr Tyr Cys Val Arg Thr Asp Gly Asp Tyr
65              70                  75

<210> SEQ ID NO 84
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Glycine, Alanine, Valine, Leucine or
      Methionine
<220> FEATURE:
<221> NAME/KEY: VARIANT

```
<222> LOCATION: (12)..(12)
<223> OTHER INFORMATION: Xaa is Glycine, Alanine, Valine, Leucine,
      Isoleucine or Methionine
<220> FEATURE:
<221> NAME/KEY: VARIANT
<222> LOCATION: (20)..(20)
<223> OTHER INFORMATION: Xaa is Glycine, Alanine, Valine, Leucine,
      Isoleucine, Proline, Phenylalanine or Methionine
<220> FEATURE:
<221> NAME/KEY: VARIANT
<222> LOCATION: (23)..(23)
<223> OTHER INFORMATION: Xaa is Glycine, Alanine, Valine, Leucine,
      Isoleucine or Methionine
<220> FEATURE:
<221> NAME/KEY: VARIANT
<222> LOCATION: (54)..(54)
<223> OTHER INFORMATION: Xaa is Proline, Phenylalanine, Tryptophan,
      Asparagine, Glutamine, Serine, Threonine or Tyrosine

<400> SEQUENCE: 84

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Ser Thr
            20                  25                  30

Asp Tyr Ser Thr Ser Leu Lys Ser Arg Leu Thr Ile Ser Lys Asp Thr
            35                  40                  45

Ser Lys Ser Gln Val Xaa Leu Lys Met Asn Ser Leu Arg Thr Asp Asp
    50                  55                  60

Thr Ala Met Tyr Tyr Cys Val Arg Thr Asp Gly Asp Tyr
65                  70                  75

<210> SEQ ID NO 85
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Isoleucine
<220> FEATURE:
<221> NAME/KEY: VARIANT
<222> LOCATION: (12)..(12)
<223> OTHER INFORMATION: Xaa is Valine
<220> FEATURE:
<221> NAME/KEY: VARIANT
<222> LOCATION: (20)..(20)
<223> OTHER INFORMATION: Xaa is Proline
<220> FEATURE:
<221> NAME/KEY: VARIANT
<222> LOCATION: (23)..(23)
<223> OTHER INFORMATION: Xaa is Methionine
<220> FEATURE:
<221> NAME/KEY: VARIANT
<222> LOCATION: (54)..(54)
<223> OTHER INFORMATION: Xaa Serine

<400> SEQUENCE: 85

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Ser Thr
            20                  25                  30

Asp Tyr Ser Thr Ser Leu Lys Ser Arg Leu Thr Ile Ser Lys Asp Thr
            35                  40                  45

Ser Lys Ser Gln Val Xaa Leu Lys Met Asn Ser Leu Arg Thr Asp Asp
    50                  55                  60

Thr Ala Met Tyr Tyr Cys Val Arg Thr Asp Gly Asp Tyr
65                  70                  75
```

```
<210> SEQ ID NO 86
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is  Isoleucine
<220> FEATURE:
<221> NAME/KEY: VARIANT
<222> LOCATION: (12)..(12)
<223> OTHER INFORMATION: Xaa is Valine
<220> FEATURE:
<221> NAME/KEY: VARIANT
<222> LOCATION: (20)..(20)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (23)..(23)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (54)..(54)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine

<400> SEQUENCE: 86

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Gly Ser Thr
            20                  25                  30

Asp Tyr Ser Thr Ser Leu Lys Ser Arg Leu Thr Ile Ser Lys Asp Thr
        35                  40                  45

Ser Lys Ser Gln Val Xaa Leu Lys Met Asn Ser Leu Arg Thr Asp Asp
    50                  55                  60

Thr Ala Met Tyr Tyr Cys Val Arg Thr Asp Gly Asp Tyr
65                  70                  75

<210> SEQ ID NO 87
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Isoleucine
<220> FEATURE:
<221> NAME/KEY: VARIANT
<222> LOCATION: (12)..(12)
<223> OTHER INFORMATION: Xaa is Isoleucine
<220> FEATURE:
<221> NAME/KEY: VARIANT
<222> LOCATION: (20)..(20)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (23)..(23)
```

-continued

```
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (54)..(54)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine

<400> SEQUENCE: 87

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Gly Ser Thr
            20              25                  30

Asp Tyr Ser Thr Ser Leu Lys Ser Arg Leu Thr Ile Ser Lys Asp Thr
            35                  40                  45

Ser Lys Ser Gln Val Xaa Leu Lys Met Asn Ser Leu Arg Thr Asp Asp
        50                  55                  60

Thr Ala Met Tyr Tyr Cys Val Arg Thr Asp Gly Asp Tyr
65                  70                  75

<210> SEQ ID NO 88
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Leucine
<220> FEATURE:
<221> NAME/KEY: VARIANT
<222> LOCATION: (12)..(12)
<223> OTHER INFORMATION: Xaa is Isoleucine
<220> FEATURE:
<221> NAME/KEY: VARIANT
<222> LOCATION: (20)..(20)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (23)..(23)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (54)..(54)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine

<400> SEQUENCE: 88

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Gly Ser Thr
            20              25                  30

Asp Tyr Ser Thr Ser Leu Lys Ser Arg Leu Thr Ile Ser Lys Asp Thr
            35                  40                  45

Ser Lys Ser Gln Val Xaa Leu Lys Met Asn Ser Leu Arg Thr Asp Asp
        50                  55                  60
```

```
Thr Ala Met Tyr Tyr Cys Val Arg Thr Asp Gly Asp Tyr
 65                  70                  75

<210> SEQ ID NO 89
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Leucine
<220> FEATURE:
<221> NAME/KEY: VARIANT
<222> LOCATION: (12)..(12)
<223> OTHER INFORMATION: Xaa is Valine
<220> FEATURE:
<221> NAME/KEY: VARIANT
<222> LOCATION: (20)..(20)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (23)..(23)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (54)..(54)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine

<400> SEQUENCE: 89

Gly Phe Ser Xaa Ser Arg Tyr Ser Val Tyr Trp Xaa Arg Gln Pro Pro
 1               5                  10                  15

Gly Lys Gly Xaa Glu Trp Xaa Gly Met Met Trp Gly Gly Gly Ser Thr
                20                  25                  30

Asp Tyr Ser Thr Ser Leu Lys Ser Arg Leu Thr Ile Ser Lys Asp Thr
             35                  40                  45

Ser Lys Ser Gln Val Xaa Leu Lys Met Asn Ser Leu Arg Thr Asp Asp
     50                  55                  60

Thr Ala Met Tyr Tyr Cys Val Arg Thr Asp Gly Asp Tyr
 65                  70                  75

<210> SEQ ID NO 90
<211> LENGTH: 77
<212> TYPE: PRT
<213> ORGANISM: Artificial
<220> FEATURE:
<223> OTHER INFORMATION: VH Part Formula I
<220> FEATURE:
<221> NAME/KEY: VARIANT
<222> LOCATION: (4)..(4)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (12)..(12)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lycine, Arginine or Histidine
<220> FEATURE:
<221> NAME/KEY: VARIANT
```

```
<222> LOCATION: (20)..(20)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (23)..(23)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine
<220> FEATURE:
<221> NAME/KEY: VARIANT
<222> LOCATION: (54)..(54)
<223> OTHER INFORMATION: Xaa is Glycine, Alanine, Valine, Leucine,
      Isoleucine, Proline, Phenylalanine, Methionine, Tryptophan,
      Cysteine, Asparagine, Glutamine, Serine, Threonine, Tyrosine,
      Aspartic acid, Glutamic acid, Lysine, Arginine or Histidine

<400> SEQUENCE: 90

Gly Phe Ser Xaa Ser Arg Tyr Ser Val Tyr Trp Xaa Arg Gln Pro Pro
1               5                   10                  15

Gly Lys Gly Xaa Glu Trp Xaa Gly Met Met Trp Gly Gly Gly Ser Thr
            20              25                  30

Asp Tyr Ser Thr Ser Leu Lys Ser Arg Leu Thr Ile Ser Lys Asp Thr
        35                  40                  45

Ser Lys Ser Gln Val Xaa Leu Lys Met Asn Ser Leu Arg Thr Asp Asp
50                  55                  60

Thr Ala Met Tyr Tyr Cys Val Arg Thr Asp Gly Asp Tyr
65                  70                  75

<210> SEQ ID NO 91
<211> LENGTH: 113
<212> TYPE: PRT
<213> ORGANISM: Artificial
<220> FEATURE:
<223> OTHER INFORMATION: VH Part Formula I

<400> SEQUENCE: 91

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Ile Ser Arg Tyr
            20                  25                  30

Ser Val Tyr Trp Val Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 92
<211> LENGTH: 113
<212> TYPE: PRT
<213> ORGANISM: Artificial
<220> FEATURE:
<223> OTHER INFORMATION: VH Part Formula I

<400> SEQUENCE: 92
```

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Lys Ser Arg Tyr
                20                  25                  30

Ser Val Tyr Trp Ile Arg Gln Pro Pro Gly Lys Gly Pro Glu Trp Met
            35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Thr Ala Met Tyr Tyr Cys Val
                85                  90                  95

Arg Thr Asp Gly Asp Tyr Trp Gly Gln Gly Thr Thr Val Thr Val Ser
                100                 105                 110

Ser

<210> SEQ ID NO 93
<211> LENGTH: 113
<212> TYPE: PRT
<213> ORGANISM: Artificial
<220> FEATURE:
<223> OTHER INFORMATION: VH Part Formula I

<400> SEQUENCE: 93

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Val Ser Arg Tyr
                20                  25                  30

Ser Val Tyr Trp Val Arg Gln Pro Pro Gly Lys Gly Pro Glu Trp Met
            35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Thr Ala Met Tyr Tyr Cys Val
                85                  90                  95

Arg Thr Asp Gly Asp Tyr Trp Gly Gln Gly Thr Thr Val Thr Val Ser
                100                 105                 110

Ser

<210> SEQ ID NO 94
<211> LENGTH: 113
<212> TYPE: PRT
<213> ORGANISM: Artificial
<220> FEATURE:
<223> OTHER INFORMATION: VH Part Formula I

<400> SEQUENCE: 94

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
                20                  25                  30

Ser Val Tyr Trp Leu Arg Gln Pro Pro Gly Lys Gly Pro Glu Trp Met
            35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 95
<211> LENGTH: 113
<212> TYPE: PRT
<213> ORGANISM: Artificial
<220> FEATURE:
<223> OTHER INFORMATION: VH Part Formula I

<400> SEQUENCE: 95

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Val Arg Gln Pro Pro Gly Lys Gly Pro Glu Trp Met
        35                  40                  45

Gly Met Met Trp Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser

<210> SEQ ID NO 96
<211> LENGTH: 113
<212> TYPE: PRT
<213> ORGANISM: Artificial
<220> FEATURE:
<223> OTHER INFORMATION: VL Formula II

<400> SEQUENCE: 96

Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Asn Ser
            20                  25                  30

Asn Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg

ANTAGONISTIC ANTI-HUMAN CD40 MONOCLONAL ANTIBODY

CROSS REFERENCE TO RELATED APPLICATION

This application claims the benefit of U.S. Provisional Application No. 60/798,819, filed on May 9, 2006, which is incorporated herein by reference.

BACKGROUND OF THE INVENTION

The invention relates to human, humanized and monoclonal antibodies with decreased immunogenicity, uses and methods of production thereof. The invention in particular relates to antagonistic anti-human CD40 monoclonal antibodies.

The CD40 molecule is a 50 kDa type I membrane glycoprotein and is expressed on B cells, monocytes/macrophages, dendritic cells (DCs) and activated endothelial cells.[1-6] Under certain conditions, CD40 can also be found on fibroblasts, epithelial cells and keratinocytes.[7] CD40 ligand (CD40L, CD154), a 32 kDa type II integral membrane glycoprotein, is transiently expressed on activated CD4+ T cells and a small population of activated CD8+ T cells.[8, 9] In addition, CD40L has been found on a number of other cell types after activation, including mast cells, basophils, B cells, eosinophils, DCs and platelets.[10, 11]

Studies in murine models have clearly demonstrated the involvement of the CD40L-CD40 interaction in the pathophysiology of various autoimmune diseases (for review, see reference[12]). Evidence from CD40L transgenic mice, which acquire lethal inflammatory bowel disease, provided the first evidence that CD40-CD40L interactions might also play a role in the pathogenesis of inflammatory bowel diseases.[13] An anti-mouse CD40L monoclonal antibody (Mab) effectively prevents mucosal inflammation and interferon-γ production by lamina propria CD4+ T cells in TNBS-induced colitis.[14] In a Severe Combined Immunodeficiency (SCID) mouse inflammatory bowel disease model it was shown that treatment with anti-CD40L from the day of T-cell reconstitution completely prevented clinical and histological appearance of experimental colitis.[15] Furthermore, anti-CD40L administration from week 5 after T-cell reconstitution could still prevent progression of the disease and treated animals showed improvement in disease symptoms and histology compared with control animals.[15] In addition, reconstitution of SCID mice with T cells from CD40L knock-out mice, further demonstrated the essential role of CD40L-expressing T cells in disease development and interleukin-12 production.[16]

The CD40-CD40L interaction can be antagonized with monoclonal antibodies (Mabs) against either CD40L or CD40. The expression of CD40L on activated platelets has resulted in thrombo-embolic events during treatment of humans with IgG$_1$ anti-human CD40L Mabs at higher dose levels and termination of the development of these Mabs.[17, 19] Antagonizing CD40 therefore seems a more attractive approach. The non-stimulatory antagonistic activity of Mab 5D12 (anti-human CD40) was demonstrated in various in vitro studies using different CD40-bearing cell types[20, 22] and chimeric 5D12 (ch5D12) antagonist activity was validated in vivo using various non-human primate disease models.[23, 27] ch5D12 is a molecularly engineered human IgG$_4$ antibody containing the murine variable domains of the heavy and light chains of 5D12 and was constructed to reduce the potential for immunogenicity and to enhance the in vivo half-life of the murine 5D12 Mab when used in humans.

Patients with Crohn's disease suffer from a debilitating inflammatory disorder of the gastrointestinal tract of which the precise aetiology and pathogenesis remain elusive.[28, 29] The disease is characterized by an influx into diseased mucosa of activated T cells, B cells and macrophages,[30, 31] local production of soluble mediators of inflammation, and damage of involved tissues.[28, 29] Mucosal CD4+ T cells and macrophages and cytokines such as tumour necrosis factor (TNF)-α and IL-12 have been shown to play a central role in initiating an inflammatory loop in Crohn's disease.[32, 38] T cells from inflamed mucosa exhibit a higher proliferative capacity,[28, 29] and secrete increased amounts of IFN-γ and IL-2. Increased levels of T-cell associated cytokine mRNA transcripts have been found in mucosal biopsies from Crohn's disease patients.[33] A dominant role of CD40L on the activated CD4+ T cells has been suggested in our studies on CD40/CD40L expression in Crohn's disease lesions.[39] CD40L can mediate a strong activation of CD40-bearing cells, predominantly B cells and macrophages, thus resulting in increased production of TNF-α and IL-12 in lesions. Using immunohistochemistry, increased staining with 5D12 was found in all samples of diseased areas from Crohn's disease patients compared to non-diseased areas. Double staining for CD40 and CD20 (B cells) or CD68 (macrophages) indicated that in the sections from patients with Crohn's disease, CD40+ cells were mainly B cells in the lymphoid follicles and macrophages in the lamina propria. Lamina propria T cells from inflamed mucosa of Crohn's disease patients induced monocytes to produce significant amounts of IL-12 and TNF-α after 48 h of co-culture. Addition of 5D12 resulted in reduced IL-12 and TNF-α production; levels of production were reduced to the levels observed using control lamina propria T cells both in the absence and presence of IFN-γ.[39]

SUMMARY OF THE INVENTION

It is an object of the invention to provide alternative molecules that share at least the kind of safety and/or efficacy of 5D12 in vivo, not necessarily the amount of said safety and/or efficacy. The antibody 5D12, or at least the variable domains thereof, have a murine background. The present invention provides variants of the heavy and light chain variable domains of 5D12. To this end the invention provides a polypeptide comprising an amino acid sequence of formula (I)

```
1             11            21            31
|             |             |             |
GFSX1S RYSVY WX2RQP PGKGX3 EWX4GM MWGGG STDYS 41            51            61
       |             |             |
TSLKS RLTIS KDTSK SQVX5L KMNSL RTDDT AMYYC

71
|
VRTDG DY (SEQ. ID. NO.: 1)
``` wherein:
X$_1$ is G, A, V, L, I, P, F, M, W, C, N, Q, S, T, Y, D, E, K, R or H;
X$_2$ is G, A, V, L, I, P, F, M, W, C, N, Q, S, T, Y, D, E, K, R or H;
X$_3$ is G, A, V, L, I, P, F, M, W, C, N, Q, S, T, Y, D, E, K, R or H;

X₄ is G, A, V, L, I, P, F, M, W, C, N, Q, S, T, Y, D, E, K, R or H; and

X₅ is G, A, V, L, I, P, F, M, W, C, N, Q, S, T, Y, D, E, K, R or H.

Said polypeptide comprises extensive sequence identity with the heavy chain variable domain of the 5D12 antibody, however, the polypeptide is less immunogenic in a human individual administered as such or in the context of an antibody comprising said polypeptide. At the indicated positions $X_1$-$X_5$ several amino acids may be present as indicated. A binding molecule comprising a polypeptide of the invention has good CD40 binding properties. It has been noted that production of the antibody in a cell varies somewhat with the kind of amino acid at the indicated positions. This will be detailed elsewhere herein below.

The invention further provides a polypeptide according to the invention comprising an amino acid sequence

```
1          11         21         31
|          |          |          |
QVKLQ ESGPG LVKPS ETLSI TCTVS GFSX1S RYSVY WX2RQP 41             51     61         71
|              |      |          |
PGKGX3 EWX4GM MWGGG STDYS TSLKS RLTIS KDTSK 81          91         101        111
     |           |          |          |
SQVX5L KMNSL RTDDT AMYYC VRTDG DYWGQ GTTVT VSS.

(SEQ. ID. NO.: 2)
```

The abovementioned polypeptide essentially spans the variable domain of the heavy chain of the murine 5D12 antibody. The amino acid sequence is altered at several positions with respect to murine sequence. The altered polypeptide couples good binding properties, while at the same time being well tolerated by humans provided with the polypeptide. At the indicated positions various amino acids can be inserted without dramatically reducing and/or altering at least immunological properties of the polypeptide when compared to the original murine polypeptide. It is preferred that a polypeptide of the invention comprises a G, A, V, L, P, F, M, W, C, N, Q, S, T, Y, D, E, K, R or H at position $X_1$. In this way at least the production properties of the polypeptide in a mammalian cell are not dramatically reduced and/or altered when compared to the original murine or chimeric polypeptide. In a particularly preferred embodiment $X_1$ is G, A, V, L, P, F or M;

$X_2$ is G, A, V, L, I, P, F or M;

$X_3$ is G, A, V, L, I, P, F, M;

$X_4$ is G, A, V, L, I, P, F, M; and $X_5$ is G, A, V, L, I, P, F, M, W, C, N, Q, S, T or Y.

These polypeptides are better suited for high level production in a mammalian cell. Particularly in the context of an antibody.

The invention further provides a polypeptide according to the invention, wherein:

$X_1$ is G, A, V, L or M;

$X_2$ is G, A, V, L, I or M;

$X_3$ is GA, V, L, I, P, F, M;

$X_4$ is G, A, V, L, I or M; and $X_5$ is P, F, W, N, Q, S, T or Y.

These polypeptides are better suited for high level antibody production while at the same time exhibiting good tolerance properties in a human. The invention further provides a polypeptide of formula (I) wherein $X_1$ is L; $X_2$ is I; $X_3$ is P; $X_4$ is M; and/or $X_5$ is S. This polypeptide is particularly preferred because of its excellent production properties in the context of an antibody that mimics the binding and pharmacological properties of antibody ch5D12 whereas immunological properties are improved in humans when compared to the murine or ch5D12 antibody and wherein at least production of the polypeptide is not dramatically reduced when compared to the murine or chimeric counterpart.

The invention further provides a polypeptide of formula (I) wherein $X_1$ is I; $X_2$ is V; $X_3$ is P; $X_4$ is M; and/or $X_5$ is S. This polypeptide is particularly preferred because of its excellent production properties in the context of an antibody that mimics the binding and pharmacological properties of antibody ch5D12 whereas immunological properties are improved in humans when compared to the murine or ch5D12 antibody and wherein at least production of the polypeptide is not dramatically reduced when compared to the murine or chimeric counterpart.

An antibody that deviates at least at one position $X_1$-$X_5$ when compared to chimeric 5D12 at the corresponding positions, has better immunological properties than the chimeric 5D12 antibody in humans. In a preferred embodiment of such antibodies the invention preferably provides a polypeptide according to the invention, wherein: $X_1$ is I and $X_2$ is V; $X_1$ is I and $X_2$ is I; $X_1$ is L and $X_2$ is I; or $X_1$ is L and $X_2$ is V. The polypeptides are particularly preferred in combination with an $X_3$ is P; $X_4$ is M; and $X_5$ is either F or S; In one embodiment the invention provides a polypeptide according to the invention, wherein: $X_1$ is L; $X_2$ is V; $X_3$ is L; $X_4$ is L and $X_5$ is F. Production of antibodies comprising said polypeptide is very good, while simultaneously providing improved immunological properties in humans when compared to ch5D12. The invention further provides a polypeptide comprising amino acid sequence GFS$X_1$S RYSVY W$X_2$R, wherein: $X_1$ is L and $X_2$ is I (SEQ. ID. NO.: 3); or $X_1$ is I and $X_2$ is V (SEQ. ID. NO.:4). This polypeptide comprises a modified CDR1 of a 5D12 heavy chain variable fragment. This CDR1 comprises at least one different amino acid when compared to the CDR1 of the heavy chain variable fragment of antibody 5D12. This amino acid change both leads to improved immunological properties of a modified 5D12 or ch5D12 antibody wherein the modification comprises at least a replacement of the corresponding sequence of said polypeptide in 5D12 or ch5D12 with a polypeptide of the invention, whereas at the same time enabling good production of the antibody in a mammalian cell.

The invention further provides a heavy chain variable domain comprising a polypeptide of formula (I). Said variable domain comprises preferably 90-130, more preferably 100-120, more preferably 105-115, most preferably 113 amino acids. The polypeptide can be generated synthetically or by a cell. Preferably said heavy chain variable domain is produced by a cell. In nature at least five types of heavy chain exist: $\gamma$, $\epsilon$, $\alpha$, $\mu$ and $\epsilon$, wherein each type defines a class of immunoglobulins. A polypeptide of the invention may be used as a binding body directly or may be incorporated into an antibody. When incorporated into an antibody the polypeptide is preferably combined with a constant part of an antibody heavy chain. To this end the invention further provides an antibody heavy chain comprising a polypeptide of formula (I). The art knows many derivatives and analogues of variable domain antibodies. However, currently many different parts, derivatives and/or analogues of antibodies are in use. Non-limiting examples of such parts, derivatives and/or analogues are, single chain Fv-fragments, monobodies, VHH, Fab-fragments, artificial binding proteins such as for example avimers, and the like. A common denominator of such specific binding bodies is the presence of a heavy chain variable domain. Thus the invention further provides a binding body comprising a polypeptide of formula (I). A preferred binding body of the invention is an antibody, as an antibody comprises a naturally occurring structure. Therefore, the invention in a preferred embodiment provides an antibody comprising a polypeptide according to the invention.

A binding body according to the invention is preferably a binding body that is well tolerated in an animal. Tolerance of an animal for a polypeptide is governed by many different aspects. Immunity, be it T-cell mediated, B-cell mediated or other is one of the variables that are encompassed in tolerance of the animal for a polypeptide. As mentioned above, the 5D12 antibody has a murine background. The polypeptide of formula (I) has a reduced immunogenicity in human. It is therefore sometimes referred to as a deimmunized variant of the heavy chain variable domain of 5D12. Thus in an aspect the invention provides an antibody comprising an epitope specificity of a 5D12 antibody, wherein the heavy chain of said antibody is a polypeptide of formula (I). Deimmunized as used herein is defined as less immunogenic in an animal than the original antibody. A polypeptide of formula (I) is deimmunized when compared to the heavy chain in 5D12 through the removal of known human T cell epitopes. T cell epitopes are amino acid sequences within proteins with the capacity to bind to MHC class II molecules. By removal of the T cell epitopes the antibody is less immunogenic. Preferably a variable domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

An antibody according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG, IgA, IgM, IgD, and IgE constant regions, more preferably said constant region comprises an IgG constant region, more preferably an $IgG_1$ constant region, preferably a mutated $IgG_1$ constant region, most preferably said constant region is an $IgG_4$ constant region. Furthermore, said $IgG_4$ constant region is preferably a human $IgG_4$ constant region. Preferably, the $IgG_4$ antibody of the invention comprises the constant regions of the heavy and light chain amino acid sequence as depicted in FIG. 18. Preferably, the $IgG_4$ antibody of the invention comprises the heavy and light chain amino acid sequence as depicted in FIG. 18. Some variation in the constant region of $IgG_4$ occurs in nature and/or is allowed without changing the immunological properties of the resulting antibody. Typically between about 1-5 amino acid substitutions are allowed in the constant region. An antibody with an $IgG_4$ constant region or a mutated $IgG_1$ constant region has at least most of the pharmacological properties of an antibody but does not bind complement, and will thus not induce depletion of the cell its binds to in vivo. Preferably said constant region is a constant region of a human antibody.

In one embodiment the invention provides a nucleic acid encoding a polypeptide according to the invention, and/or a binding body according to the invention, and/or an antibody according to the invention. A nucleic acid as used in the invention is typically but not exclusively a ribonucleic acid (RNA) or a deoxyribonucleic acid (DNA). Alternative nucleic acids are available for a person skilled in the art, such as for instance peptide nucleic acids (PNA). A nucleic acid according to the invention is for instance comprised in a cell. When said nucleic acid is expressed in said cell, said cell produces a polypeptide and/or a binding body and/or an antibody according to the invention. Therefore, the invention in one embodiment provides a cell comprising a polypeptide according to the invention, a binding body according to the invention, an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing a polypeptide according to the invention, a binding body according to the invention, an antibody according to the invention and/or a nucleic acid according to the invention.

The invention further provides a cell comprising an antibody according to the invention. Preferably said cell produces said antibody. In a preferred embodiment said cell is a hybridoma cell, a Chinese hamster ovary (CHO) cell, an NSo cell or a PER.C6™ cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NSo cells or PER.C6™ cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of protein and/or antibody for the production of an antibody of the invention.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, an NSo cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof. Preferably a variant that makes use of a Glutamine synthetase (GS) vector system for expression of an antibody.

It has been noted that some amino acids at the mentioned positions $X_1$-$X_5$ are less suited for high level production of an antibody comprising a polypeptide of formula (I) in an antibody producing cell. In a preferred embodiment a polypeptide of formula (I) in said antibody comprises $X_1$-$X_5$ wherein:
$X_1$ is G, A, V, L, I, P, F, M, W, C, N, Q, S, T, Y, D, E, K, R or H. In a particularly preferred embodiment $X_1$ is G, A, V, L, I, P, F or M; $X_2$ is G, A, V, L, I, P, F or M; $X_3$ is G, A, V, L, I, P, F, M; $X_4$ is G, A, V, L, I, P, F, M; and $X_5$ is G, A, V, L, I, P, F, M, W, C, N, Q, S, T or Y. More preferably, said antibody comprises a polypeptide of formula I wherein $X_1$ is G, A, V, L, I or M; $X_2$ is G, A, V, L, I or M; $X_3$ is G, A, V, L, I, P, F, M; $X_4$ is G, A, V, L, I or M; and $X_5$ is P, F, W, N, Q, S, T or Y. More preferably $X_1$ is L; $X_2$ is I; $X_3$ is P; $X_4$ is M; and/or $X_5$ is S. Particularly preferred is when $X_1$ is I and $X_2$ is V; $X_1$ is I and $X_2$ is I; $X_1$ is L and $X_2$ is I; $X_1$ is L and $X_2$ is L; $X_1$ is V and $X_2$ is I; $X_1$ is V and $X_2$ is V; $X_1$ is L and $X_2$ is L; $X_1$ is V and $X_2$ is L; or $X_1$ is L and $X_2$ is V. These latter polypeptides are particularly preferred in combination with an $X_3$ is P; $X_4$ is M; and $X_5$ is either F or S, preferably S; In one embodiment the invention provides a polypeptide according to the invention, wherein: $X_1$ is L; $X_2$ is V; $X_3$ is L; $X_4$ is L and $X_5$ is F. Production of antibodies comprising said polypeptide is good, while simultaneously providing improved immunological properties in humans when compared to ch5D12.

In another preferred embodiment the invention provides a polypeptide according to the invention wherein at least one of $X_1$, $X_2$, $X_3$, $X_4$ or $X_5$ is the same as an amino acid at the corresponding position in a sequence that is shown by the invention to yield specifically good expression levels and wherein further at least one of $X_1$, $X_2$, $X_3$, $X_4$ or $X_5$ is the same as an amino acid at the corresponding position in a 5D12 amino acid sequence. An advantage of a polypeptide according to the invention wherein at least one of $X_1$, $X_2$, $X_3$, $X_4$ or $X_5$ is the same as an amino acid at the corresponding position in a 5D12 amino acid sequence, is that a binding body according to the invention comprising such a polypeptide shows a better expression level than a polypeptide according to the invention wherein none of $X_1$, $X_2$, $X_3$, $X_4$ or $X_5$ are the same as an amino acid at the corresponding position in a 5D12 amino acid sequence. Without being bound by theory, said better expression level is believed to be due to the fact that an amino acid at the position of $X_1$, $X_2$, $X_3$, $X_4$ and/or $X_5$ contributes to a proper assembly of a binding body according to the invention when said amino acid is the same as an amino acid at the corresponding position in a 5D12 amino acid sequence.

An antibody comprising a polypeptide of formula (I) shows non-stimulatory antagonistic activity. As the CD40L-CD40 interaction is involved in the pathophysiology of various inflammatory disorders such as autoimmune diseases and graft rejection, a polypeptide according to the invention is therefore particularly suited for ameliorating a symptom of an inflammatory disorder. In one embodiment an antibody comprises a binding body of the invention. In a preferred embodiment said antibody is a monoclonal antibody. Monoclonal antibody technology allows for production of large amounts of essentially pure antibodies, thus obtaining predictable products. Therefore, the invention in one embodiment provides an antagonistic anti-human CD40 monoclonal antibody comprising a polypeptide according to the invention. A binding body according to the invention is all the more suitable for that purpose since it is in one embodiment deimmunized compared to a mouse 5D12 and/or a chimeric 5D12. Therefore, a binding body of the invention has a reduced immunogenicity and an enhanced half-life in humans compared to a mouse 5D12 and/or a chimeric 5D12. As a result thereof, a binding body of the invention has a sustainable pharmaceutical potential against various inflammatory disorders. Thus, in a preferred embodiment the invention provides a deimmunized antagonistic anti-human CD40 monoclonal antibody according to the invention.

As referred to previously, the present invention provides 5D12 like molecules that comprise amino acid alterations with respect to the 5D12 amino acid sequence, wherein the alterations are at least in the heavy chain variable domain and preferably also in the light chain variable domain. In this context the invention further provides a binding body according to the invention comprising an amino acid sequence of formula (II)

```
1            11           21           31
|            |            |            |
X6LGX7X8 ASISC RSSQS LX9NSN GNTYL HWYLQ RPGQS 41           51           61           71
|            |            |            |
PRLLI YKVSN RFSGV PDRFS GSGSG TDFTL KISRV EAEDX10

81           91
|            |
GVYX11C SQSTH VPWT (SEQ. ID. NO.: 5)
``` wherein:
$X_6$ is G, A, V, L, I, P, F, M, W, C, N, Q, S, T, Y, D, E, K, R or H;
$X_7$ is G, A, V, L, I, P, F, M, W, C, N, Q, S, T, Y, D, E, K, R or H;
$X_8$ is G, A, V, L, I, P, F, M, W, C, N, Q, S, T, Y, D, E, K, R or H;
$X_9$ is G, A, V, L, I, P, F, M, W, C, N, Q, S, T, Y, D, E, K, R or H;
$X_{10}$ is G, A, V, L, I, P, F, M, W, C, N, Q, S, T, Y, D, E, K, R or H; and
$X_{11}$ is G, A, V, L, I, P, F, M, W, C, N, Q, S, T, Y, D, E, K, R or H.

Said binding body is preferably an antagonistic anti-human CD40 monoclonal antibody according to the invention. In a preferred embodiment an X selected from $X_6$, $X_7$, $X_8$, $X_9$, $X_{10}$ or $X_{11}$ is selected from a group resembling an amino acid at a corresponding position in a 5D12 amino acid sequence and/or resembling an amino acid at a corresponding position in a sequence that is shown by the invention to yield good expression levels, as shown in example 2. Therefore, a binding body according to the invention preferably comprises an amino acid sequence of formula (II) wherein:
$X_6$ is N, Q, S, T, Y, W or C;
$X_7$ is D, E, N, Q, S, T, Y, W or C;
$X_8$ is N, Q, S, T, Y, G, A, V, L, I, P, F, M, W or C;
$X_9$ is G, A, V, L, I, P, F, M;
$X_{10}$ is G, A, V, L, I, P, F, M; and
$X_{11}$ is N, Q, S, T, Y, G, A, V, L, I, P, F, M, W or C.

In another embodiment the invention provides an antagonistic anti-human CD40 monoclonal antibody according to the invention comprising a polypeptide of formula (II) of the invention comprising an amino acid sequence as follows.

```
1            11           21           31
|            |            |            |
ELQLT QSPLS LPVX6L GX7X8AS ISCRS SQSLX9 NSNGN TYLHW 41           51           61           71
|            |            |            |
YLQRP GQSPR LLIYK VSNRF SGVPD RFSGS GSGTD FTLKI 81           91          101          111
|            |            |            |
SRVEA EDX10GV YX11CSQ STHVP WTFGG GTKLE IKR.

(SEQ. ID. NO.: 6)
```

In a preferred embodiment the invention provides a polypeptide of formula (II) of the invention wherein $X_6$ is T or S, $X_7$ is D or Q, $X_8$ is Q or P, $X_9$ is V or A, $X_{10}$ is V or L and $X_{11}$ is F or Y. More preferably wherein: $X_6$ is T, $X_7$ is Q, $X_8$ is P, $X_9$ is A, $X_{10}$ is V and $X_{11}$ is Y. 5D12-like antibodies comprising a polypeptide of formula (I) and the preferred polypeptide of formula (II) combine good expression levels in a producing cell with good tolerance properties and pharmacodynamic properties in a human.

An anti human-CD40 antagonist antibody of the invention preferably comprises a heavy chain variable domain amino acid sequence of formula (I) and a light chain variable domain amino acid sequence of formula (II). Such an antibody has good characteristics. It is of course possible to generate variants of such an original antibody by modifying one or more amino acids therein. Many of such variants will behave more or less similar when compared to said original. Such variants are also included in the scope of the invention. There are many ways to modify an antibody of the invention. A non-limiting example of such a modification is an antibody comprising a pyro-glutamate instead of a glutamate. Other non-limiting examples of such modifications are an insertion, deletion, inversion and/or substitution of one or more amino acids when compared to said original antibody. The present invention provides means and methods for generating such a variant. It also provides tests for determining the characteristics of said a variant. In a preferred embodiment the invention provides a variant of an original antibody of the invention said variant comprising an insertion, deletion, inversion and/or substitution of between about 1 to 10 amino acids when compared to the amino acid sequence of said original antibody. Preferably said insertion, deletion, inversion and/or substitution does not comprise the amino acids at position $X_1$ and position $X_2$ of the heavy chain variable domain of formula (I) of the original antibody.

In a preferred embodiment the invention provides a method for selecting an anti-human CD40 antagonist antibody comprising generating a first cell line that produces an original anti-human CD40 antagonist antibody and determining the amount of original antibody that is produced by said first cell line, said original antibody comprising the heavy chain variable domain amino acid sequence

```
1           11          21          31
|           |           |           |
QVKLQ ESGPG LVKPS ETLSI TCTVS GFSX₁S RYSVY WX₂RQP 41          51          61          71
|           |           |           |
PGKGP EWMGM MWGGG STDYS TSLKS RLTIS KDTSK 81          91          101         111
        |           |           |           |
SQVSL KMNSL RTDDT AMYYC VRTDG DYWGQ GTTVT VSS
``` wherein $X_1$ and $X_2$ are pair wise selected from the group consisting of $X_1$=I and $X_2$=V (SEQ. ID. NO.: 7); $X_1$=L and $X_2$=I (SEQ. ID. NO.: 8); $X_1$=V and $X_2$=V (SEQ. ID. NO.:9); $X_1$=L and $X_2$=L (SEQ. ID. NO.:10); or $X_1$=L and $X_2$=V (SEQ. ID. NO.: 11), said method further comprising generating at least one further cell line that produces a variant of said original antibody wherein said variant antibody is a modified original antibody comprising an insertion, deletion, inversion, and/or substitution of between about 1 to 5 amino acids when compared to said original antibody, wherein said modification does not consist of a modification of the amino acids at the position(s) identified by $X_1$ and $X_2$, and determining the amount of variant antibody that is produced by said at least one further cell line, said method further comprising selecting a variant antibody that was produced at an amount that was at least 50% of the amount of original antibody. Preferably said original antibody comprises the light chain amino acid sequence

```
1           11          21          31
|           |           |           |
ELQLT QSPLS LPV T L G Q P AS ISCRS SQSL A NSNGN
TYLHW 41          51          61          71
|           |           |           |
YLQRP GQSPR LLIYK VSNRF SGVPD RFSGS GSGTD FTLKI 81              91          101         111
|               |           |           |
SRVEA ED V GV Y Y CSQ STHVP WTFGG GTKLE IKR.
```

(SEQ. ID. NO.: 12)

Said insertion, deletion, inversion, and/or substitution of between about 1 to 5 amino acids can be in any part of the antibody not being or involving the amino acids at positions $X_1$ and $X_2$. Preferably, said insertion, deletion, inversion, and/or substitution of between about 1 to 5 amino acids is in said heavy chain amino acid sequence or said light chain amino acid sequence when compared to the corresponding chain amino acid sequence in said original antibody. Preferably said insertion, deletion, inversion, and/or substitution of between about 1 to 5 amino acids is in said heavy chain amino acid sequence when compared to said heavy chain sequence of said original antibody.

Preferably said method further comprises generating an antibody producer cell line that produces said selected antibody. This producer cell line can be said further cell line, or yet another cell line that produces said selected antibody. Preferably said method further comprises collecting said selected antibody. The invention further provides an isolated and/or recombinant anti-human CD40 antagonist antibody obtainable by a method according to the invention. In a preferred embodiment said anti-human CD40 antagonist antibody comprises a modification of the heavy chain amino acid sequence

```
1           11          21          31
|           |           |           |
QVKLQ ESGPG LVKPS ETLSI TCTVS GFSX₁S RYSVY WX₂RQP 41          51          61          71
|           |           |           |
PGKGP EWMGM MWGGG STDYS TSLKS RLTIS KDTSK 81          91          101         111
        |           |           |           |
SQVSL KMNSL RTDDT AMYYC VRTDG DYWGQ GTTVT VSS
``` wherein $X_1$ and $X_2$ are pair wise selected from the group consisting of $X_1$=I and $X_2$=V (SEQ. ID. NO.: 7); $X_1$=L and $X_2$=I (SEQ. ID. NO.: 8); $X_1$=V and $X_2$=V (SEQ. ID. NO.: D; $X_1$=L and $X_2$=L (SEQ. ID. NO.: 10); or $X_1$=L and $X_2$=V (SEQ. ID. NO.: 11), said modification comprising an insertion, deletion, inversion, and/or substitution of between about 1 to 5 amino acids when compared to said heavy chain amino acid sequence and wherein said modification does not consist of a modification of the amino acids at the position(s) identified by $X_1$ and $X_2$.

In one embodiment the invention provides a pharmaceutical composition comprising a polypeptide according to the invention, a binding body according to the invention, an antibody according to the invention, a nucleic acid according to the invention and/or a cell according to the invention. Also, the invention provides a polypeptide according to the invention, a binding body according to the invention, an antibody according to the invention, a nucleic acid according to the invention and/or a cell according to the invention for use as a medicament. Preferably a medicament for ameliorating a symptom of an autoimmune disorder and/or an inflammatory disorder and/or for reducing graft rejection and/or for the treatment of CD40 positive cancers. In a preferred embodiment said autoimmune and/or an inflammatory disorder is selected from the group of inflammatory bowel disease, rheumatoid arthritis, systemic lupus erythematosus, multiple sclerosis, psoriasis, bullous pemphigoides and atopic dermatitis.

As a polypeptide according to the invention is particularly suited for ameliorating a symptom of an inflammatory disorder because of its non-stimulatory CD40 antagonizing properties, a polypeptide according to the invention is suitable for ameliorating a symptom of several disorders. An inflammatory disorder as used in the invention is defined as any disease that involves an inflammatory component. For the interest of the invention, an inflammatory disorder specifically includes an autoimmune disorder and/or graft rejection. The central role of CD40-CD40L interaction in the initiation, amplification and prolongation of immune responses makes a polypeptide of the invention specifically suitable for immune modulation in an autoimmune disorder.

DETAILED DESCRIPTION OF THE INVENTION

Herein below information is provided on CD40 and CD40L in order to illustrate the role of CD40 and its ligand in inflammatory disorders. The CD40 molecule is a 50 kDa type I membrane glycoprotein and is expressed on B cells, monocytes/macrophages, and dendritic cells (DCS)[45-50]. Moreover, under pathological conditions CD40 can be found on endothelial cells (ECs), fibroblasts, epithelial cells and keratinocytes[51]. CD40 ligand (gp39, TBAM, TRAP, CD40L, CD154), a 32 kDa type II integral membrane glycoprotein, is transiently expressed on activated CD4+ T cells and a small population of activated CD8+ T cells[52, 53]. In addition, CD40L has been found on a number of other cell types after activation, including mast cells, basophils, B cells, eosinophils, DCs and platelets[54, 55].

Engagement of CD40 by CD40L triggers a number of biological events in B cells including proliferation, expression of activation markers, immunoglobulin (Ig) production, isotype switching, homotypic adhesion and rescue from apoptosis[56, 57]. However, as described above, the distribution of the CD40 molecule is not restricted to B cells as was originally postulated. Freshly isolated human monocytes express low levels of the CD40 molecule, which can be up-regulated by culture in the presence of IFN-$\gamma$[47-49, 58]. CD40 ligation of monocyte/macrophages induces the secretion of large amounts of pro-inflammatory mediators such as IL-1, TNF-$\alpha$ and IL-12, which induce inflammatory responses and tumoricidal activity[47-49, 58], and rescue them from apoptosis[48]. CD40 ligation also causes DCs to enhance their differentiation and: activation, to enhance expression of costimulatory molecules such as CD86, CD80 and CD58, to increase cytokine production, and to inhibit apoptosis[50, 59]. Furthermore, when expressed under inflammatory conditions, CD40 signaling can induce expression of intercellular adhesion molecule 1 (ICAM-1), vascular cell adhesion molecule 1 (VCAM-1) and E-selectin on ECs[55]. These results suggest that signaling through CD40 during T cell-EC interactions may be an important step in the regulation of EC activation and leukocyte recruitment into non-lymphoid tissues. In vivo studies have indicated the importance of the CD40-CD40L interactions in the generation of humoral immune responses[60, 61], in the priming and activation of antigen-specific T cells[62], in the temporal activation of macrophages[633], as well as in the protective cell-mediated immune responses through T-cell mediated macrophage activation against intracellular parasite infections such as *Pneumocystis, Cryptosporidium*, and *Leishmania*[64-66].

A specific role for CD40 and its ligand is demonstrated in murine models of autoimmune disease. Animal model studies have clearly indicated the involvement of the CD40L-CD40 interaction in the pathophysiology of various autoimmune diseases. In these studies, using mice suffering from spontaneous or experimental autoimmune diseases, interfering with CD40L-CD40 interactions had clear beneficial effects. A Mab to murine CD40L was shown to prevent or reduce disease symptoms in collagen-induced arthritis, experimental allergic encephalomyelitis (EAE; an animal model for MS), in (SWR×NZB)F1 lupus mice and in non-obese diabetic (NOD) mice that spontaneously develop T-cell dependent autoimmune diabetes. Evidence indicates that CD40-CD40L interactions also play a role in the pathogenesis of inflammatory bowel diseases, which includes Crohn's disease and ulcerative colitis. CD40L transgenic mice with high transgene copy numbers were shown to acquire lethal inflammatory bowel disease marked by infiltration of CD40+ cells and CD40L+ T cells into diseased tissues[67]. Anti-CD40L Mab effectively prevent mucosal inflammation and IFN-$\gamma$ production by lamina propria CD4+ T cells in animals with colitis that had been induced by 2,4,6-trinitrobenzene sulfonic acid[44]. Very recently a direct comparison was made between anti-TNF-$\alpha$ treatment and interference of the CD40-CD40L pathway using an anti-CD40L Mab in a SCID mouse experimental inflammatory bowel disease model. In this model, syngeneic CD45RB$^{high}$ CD4+ cells are injected into SCID mice that subsequently develop diarrhea or soft stools and show progressive weight loss starting 3-5 weeks after T-cell reconstitution, as symptoms of experimental inflammatory bowel disease. Treatment with either anti-TNF-$\alpha$ or anti-CD40L from the day of T-cell reconstitution completely prevented clinical and histological appearance of experimental inflammatory bowel disease. Furthermore, anti-CD40L administration from week 5 after T-cell reconstitution could still prevent progression of the disease and treated animals showed improvement in disease symptoms and histology compared to control animals (unpublished observations).

Recent work has also demonstrated that interference with the CD40-CD40L pathway is strongly immunosuppressive in transplantation models. Combined treatment with allogeneic small lymphocytes or T cell-depleted small lymphocytes plus an antibody to mouse CD40L permitted indefinite pancreatic islet allograft survival in 37 out of 40 recipients that differed in major and minor histocompatibility loci[68]. From these experiments it was concluded that the effective interference of the CD40L-CD40 interaction most likely had resulted in preventing the induction of costimulatory molecules on the small resting lymphocytes by the alloreactive host T cells. In another recent study, it was demonstrated that administration of a Mab to mouse CD40L at the time of transplantation markedly prolonged survival of fully disparate murine cardiac allografts in both naive and sensitized hosts. However, when anti-CD40L therapy was delayed until postoperative day 5, anti-CD40L failed to prolong graft survival. From this study, it was concluded that anti-CD40L therapy inhibited allograft rejection primarily by interfering with T cell help for effector functions. It has further been shown that interfering with CD80/CD86-CD28 and CD40-CD40L pathways simultaneously effectively aborts T cell clonal expansion in vitro and in vivo, promotes long-term survival of fully allogeneic skin grafts, and inhibits the development of chronic vascular rejection of primarily vascularized cardiac allografts. Furthermore, interfering with a CD40-CD40L pathway, optionally in combination with interference with a CD80/CD86-CD28 pathway, prevents kidney allograft rejection in a rhesus monkey kidney allograft model[69, 70]. For further information on the effects of 5D12 in inflammatory disorders, see for instance references[71-81].

Multiple sclerosis is an autoimmune disease of the central (cerebrospinal) nervous system. In this disorder, the white matter surrounding nerve fibers becomes hardened. The term multiple sclerosis (MS) literally means "many scars." The hardened areas of nerve tissue are called plaques. The symptoms, severity, and course of multiple sclerosis are highly variable, depending partly on the sites of the plaques and the extent of the deterioration of the white matter. The deterioration of white matter in the nervous system slows nerve impulses leading to nervous system incoordination.

Experimental autoimmune encephalomyelitis (EAE) in the common marmoset (*Callithrix jacchus*) is a useful preclinical model of multiple sclerosis (reviewed in[86, 87, 102, 104]). The central nervous system (CNS) white matter lesions that develop in the various versions of this EAE model share pathomorphological, radiological and immunological features with MS[95, 98, 101]. Hence, the marmoset EAE model can bridge the wide immunological gap between humans and rodents that hampers the selection of promising treatments in the drug development pipeline at a preclinical stage[96, 99, 103].

Marmosets immunized with rhMOG, a recombinant protein representing the extracellular fragment of human MOG (amino acids 1-125) develop EAE in 100% of the cases, which is due to the presence of the monomorphic MHC class II susceptibility element Caja-DRB*W1201 in the repertoire of each monkey[82, 84, 85, 107]. A particularly useful aspect of this model for therapy development is that lesions developing in the brain white matter can be visualized and tentatively characterized with clinically relevant magnetic resonance imaging techniques[92, 105]. Longitudinal analysis of the brain white matter lesions with magnetic resonance imaging (MRI) showed a progressive increment of the volume and persistent inflammatory activity in the majority of the lesions. Furthermore, the characterization of the CNS pathology with MRI and previously described histological criteria[101] revealed that the majority of the lesions are in an early active stage[106].

The rhMOG-induced EAE model has been used to test whether antibodies targeting co-stimulatory molecules of antigen presenting cells (APC) and T-cells are a potential treatment for MS. The interaction of CD40 with its ligand CD154 plays an important role in various immunopathogenic processes that operate in EAE, including B-cell activation, antigen-presenting cell (APC) activation, initiation of antigen-specific T-cell responses and induction of macrophage effector functions[90, 93, 97, 7]. A study performed in 1996 confirmed that mice treated with an antibody against CD154 are protected against EAE[88]. However, a clinical trial in MS patients with antibody against CD154 was stopped due to unexpected side-effects that were not observed in the animal experiments[17].

The mouse monoclonal antibody (Mab) 5D12 (mu5D12) has been raised against human CD40. The 5D12 antibody appeared a potent inhibitor of CD40-CD40L mediated activation on several cell types and, unlike most other anti-CD40 Mabs, does not exert CD40 stimulatory activity[21, 22, 39]. Both the mouse anti-human CD40 antibody mu5D12 and the chimeric version of this antibody, ch5D12, displayed strong suppressive effects on the development of CNS white matter lesions and neurological deficit in the marmoset EAE model and showed no marked side-effects[23, 24]. The same studies showed that intravenously injected anti-CD40 Mab into EAE affected common marmosets can gain access to the brain white matter lesions where CD40 molecules are prominently expressed on infiltrated macrophages and activated microglia[95], as was found earlier in MS[88]. This has raised the question whether ch5D12 also has a therapeutic effect on already existing lesions.

't Hart et al monitored brain lesion development in 7 rhMOG-immunized monkeys by serial magnetic resonance imaging (MRI) at 2 weeks interval[76]. The results of this study demonstrated suppression of lesion inflammation in all 3 ch5D12-treated monkeys while lesion enlargement was diminished in 2 of the 3 ch5D12-treated monkeys.

Prevention of CD40 engagement with its ligand CD154 on activated T cells early in the disease process has a significant impact on the clinical and neuropathological expression of EAE in rodents[88, 89, 91, 94, 100] and non-human primate models[23, 24]. CD40 is prominently expressed within the CNS white matter lesions of MS patients as well as EAE-affected rodents[88] and non-human primates 95. That CD40 bearing APC within the CNS, such as infiltrated macrophages as well as perivascular and parenchymal glia cells, contribute significantly to the pathogenesis of EAE has been elegantly shown in bone marrow chimeric mice[83].

The results of 't Hart et al, Laman et al, and Boon et al.[76, 79, 81] indicate that antibody blockade of CD40 is a potentially effective treatment of MS. Importantly, the ch5D12 Mab has no apparent side effects in the marmoset EAE model nor in other primate species[80]. The beneficial clinical effect of anti-CD40 antibody was demonstrated in placebo-controlled experiments in two EAE models in marmosets, namely induced with human myelin[79] or rhMOG[81]. In addition, 't Hart et al have shown an inhibitory effect of anti-CD40 antibody treatment on already existing lesions[76].

Psoriasis is an inflammatory skin disease afflicting 1-2% of the population. In this disease, T cells and keratinocytes in the lesions are activated and express activation markers and co-stimulatory molecules. It is thought that some co-stimulatory molecules expressed on keratinocytes and T cells interact with each other and that these interactions contribute to disease activity[108-110]. One such set of molecules may be CD40, which is expressed on activated keratinocytes, and CD154 (CD40 ligand), which is transiently expressed on activated CD4+ T cells. CD40-CD154 ligation between T cells and keratinocytes may release from these cells inflammatory mediators that are seen in abundance in psoriatic lesions. CD40, CD154, and CD40-CD154 interactions have recently been reviewed[111]. Cultured keratinocytes also express CD40; expression is enhanced by IFN-treatment. Ligation of highly expressed CD40 on IFN-gamma treated keratinocytes (referred to as CD40++ keratinocytes throughout this paper) with CD154 results in up-regulation of ICAM and increased production of cytokines[112-114].

So far, only one report has appeared that implicates this ligation in the pathogenesis of psoriasis[113]. The cell types that express CD40 in psoriatic lesions were not identified in the latter study and their incidence and lesional status were not described. The presence of CD154+ T cells in psoriatic lesions was also not studied. Thus, it remains unknown whether CD154 acts as one of the signals for production by keratinocytes of chemokines and complement, which are found in abundance in psoriatic lesions[115].

Pasch et al recently demonstrated the presence and localization of CD40+ and CD154+ cells by immunohistochemistry in lesional and non-lesional skin from ten psoriasis patients[116]. Increased positivity for CD40 was observed on clusters of keratinocytes, and high expression of CD40 was shown on almost all CD1a+ Langerhans cells in normal, non-lesional, and lesional epidermis. In addition, high expression of CD40 was present on almost all CD83+ cells in psoriatic lesions; they were rarely seen in non-lesional and normal skin[116]. Also, a small proportion of T cells showed CD154 expression, in most patients in juxtaposition to CD40+ cells. These results raised the possibility that CD154+ T cells may ligate with CD40+ keratinocytes, Langerhans cells, and CD83+ dendritic cells, and release mediators from them in the lesion.

In addition, they demonstrated that CD40 ligation induces the release of chemokines (IL-8, RANTES, and MCP-1)[116]. In the same publication, Pasch et al. showed that the CD40-related release of the chemokines IL-8, MCP-1 and to a lesser extent of RANTES was inhibited by the antagonistic anti-CD40 antibody 5D12[116]. These data suggest that antagonist anti-CD40 mAb 5D12 may at least in part have an effect on the inflammation seen in psoriatic lesions. US2003/0165499 discloses a measurable anti-psoriatic effect of the 5D12 and other antagonistic anti-CD40 antibodies in a SCID mouse xenogeneic transplant model system that is used as a model for psoriasis treatment, showing that antagonistic anti-CD40 antibodies may be used for the treatment of psoriasis. A therapeutic effect of 5D12 in this in vivo system was demonstrated In a particularly preferred embodiment said autoimmune and/or an inflammatory disorder comprises inflammatory bowel disease. In another preferred embodiment a use of the invention is provided wherein said inflammatory bowel disease comprises ulcerative colitis (UC) or Crohn's disease (CD).

As illustrated above, a polypeptide according to the invention is suited for treatment of diverse inflammatory disorders, including autoimmune disorders and graft rejection. Therefore, the invention in one embodiment provides a method for ameliorating a symptom of an autoimmune disorder and/or an inflammatory disorder and/or for reducing graft rejection. In a further embodiment the invention provides use of a polypeptide according to the invention, a binding body according to the invention, an antibody according to the invention, a nucleic acid according to the invention and/or a cell according to the invention for the manufacture of a medicament for ameliorating a symptom of an autoimmune disorder and/or an inflammatory disorder and/or for reducing graft rejection. Ameliorating a symptom as used in the invention is defined as ameliorating at least one symptom of a disorder at least partially. The invention is of specific interest for autoimmune and/or inflammatory disorders for which at present no efficient treatment exists. Examples of these disorders are rheumatoid arthritis, systemic lupus erythematosus, multiple sclerosis, psoriasis, inflammatory bowel disease, bullous pemphigoides and atopic dermatitis. A polypeptide according to the invention, optionally comprised in a binding body or a cell of the invention and/or encoded by a nucleic acid of the invention, is specifically suited for ameliorating a symptom of an autoimmune and/or inflammatory disorder as defined properties of a polypeptide according to the invention allow for interfering with a CD40-CD40L pathway in a specific manner. Furthermore, since a binding body according to the invention is preferably deimmunized, a binding body according to the invention is present for a sustained period of time and thus shows its antagonizing activity in a patient for a considerable period of time. Therefore, the invention in one embodiment provides a use of a polypeptide according to the invention, a binding body according to the invention, an antibody according to the invention, a nucleic acid according to the invention and/or a cell according to the invention for the manufacture of a medicament for ameliorating a symptom of an autoimmune disorder and/or an inflammatory disorder and/or for reducing graft rejection, wherein said autoimmune and/or said inflammatory disorder is selected from the group of rheumatoid arthritis, systemic lupus erythematosus, multiple sclerosis, psoriasis, inflammatory bowel disease, bullous pemphigoides and atopic dermatitis.

BRIEF DESCRIPTION OF THE DRAWINGS

FIG. 5. Consensus DNA (SEQ ID NO: 45, SEQ ID NO: 47) and deduced amino acid sequences (SEQ ID NO: 46, SEQ ID NO: 48) of the murine 5D12 VH and VL region.

FIG. 7. Alignment of the 12 tested amino acid variants (Q5E (SEQ ID NO: 53), K13A (SEQ ID NO: 54), E16Q (SEQ ID NO: 55), T17S (SEQ ID NO: 56), I29L (SEQ ID NO: 57), 137V (SEQ ID NO: 58), P45L (SEQ ID NO: 59), M48L (SEQ ID NO: 60), STS60NSA (SEQ ID NO: 61), T68S (SEQ ID NO: 62), S79F (SEQ ID NO: 63), and T108S (SEQ ID NO: 64)) of deimmunised 5D12 VH compared with the parent murine sequence (ch5D12) (SEQ ID NO: 65) and the fully deimmunised sequence (D15D12) (SEQ ID NO: 66).

FIG. 8. FACS analysis using JY cells. PER.C6 cell supernatant of the transient expressed variants (Q5E, K13A, E16Q, T17S, I29L, 37V, P45L, M48L, STS60NSA, T68S, S79F, and T108S) of 5D12 was harvested after 48 h. As control also supernatant was harvested of cells transfected with either ch5D12 or D15D12 together with supernatant from mock (no plasmid) transfected cells. Binding of expressed antibodies was tested by FACS using JY cells together with anti-human FITC labelled secondary antibody (1/100 diluted). As FACS control JY cells were incubated with only the secondary FITC labelled antibody.

FIG. 9. Alignment of the additional V-L-I variants on positions 29 and 37 (29I-37V (SEQ ID NO: 67), 29V-37I (SEQ ID NO: 68), 29I-37L (SEQ ID NO: 69), 29V-37V (SEQ ID NO: 70), 29L-37L (SEQ ID NO: 71), 29V-37L (SEQ ID NO: 72), 29L-37V (SEQ ID NO: 73)) of deimmunised 5D12 VH compared with the parent chimeric sequence (ch5D12) (SEQ ID NO: 74), the fully deimmunised sequence (DI5D12; 291-371) (SEQ ID NO: 75) and PG102 (29L-37I) (SEQ ID NO: 76).

EXAMPLES

Example 1

Materials and Methods

Figure 1:
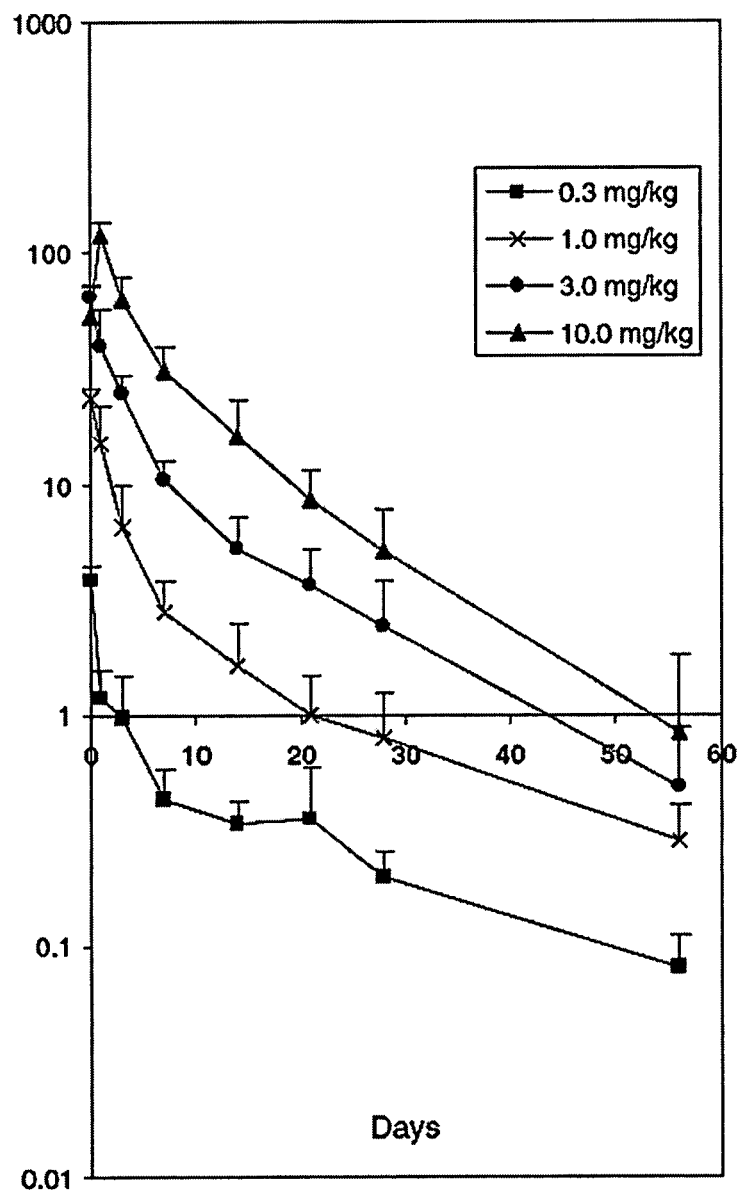
FIG. 1. ch5D12 serum concentration after single administration at day o at the four dose levels as indicated by the symbols. Values are given as µg ch5D12/mL serum and were determined by enzyme-linked immunosorbent assay as detailed in Ref[27].

Eighteen adult subjects (18-60 years of age) with a clinical diagnosis of Crohn's disease confirmed by radiological, endoscopic or histological evidence, and with a Crohn's Disease Activity Index (CDAI) score of at least 220 but not more than 450 (scored over 7 days prior to study drug administration) were selected for study inclusion. Subjects were allowed to have the following treatments before and during the study: mesalamine treatment for 8 or more weeks with the dose remaining stable for the 4 weeks before screening; a maximum of 30 mg of corticosteroids per day (or 9 mg budesonide per day) for 8 or more weeks, with the dose remaining stable 2 weeks before screening; mercaptopurine or azathioprine for 4 or more months with the dose remaining stable for 8 weeks before screening. Subjects could not have received treatment with cyclosporin A or methotrexate within 3 months before screening nor were they allowed to have prior exposure to treatment with Mabs. The average age of all subjects enrolled was 35.8 years of whom seven were males and 11 were females. All subjects were of Caucasian ethnicity. No apparent differences between patients in the different cohorts at inclusion were observed (Table 1), with the exception that in the lower three dose groups the majority of the subjects were females, while the highest dose group (10.0 mg/kg) consisted of only male subjects. There were no notable differences between the four cohorts with regard to baseline electrocardiogram (ECG), vital signs, physical examinations, history of Crohn's disease signs and symptoms, and baseline laboratory values. There were no significant differences regarding baseline characteristics amongst the four dose cohorts. The highest dose cohort however also showed the highest CDAI score at baseline. This study was approved by the Medical Ethical Boards of The University Hospitals Leuven, Belgium, Leiden University Medical Center, The Netherlands, Medizinische Klinik, Kiel, Germany, and Hadassah Medical Center, Jerusalem, Israel. All patients gave informed consent to the study.

Study Design and Treatment-Protocol ch5D12 is a molecularly engineered human IgG4 antibody containing the variable domains of the heavy and light chains of Mab 5D12 parent version. This Mab has been shown to bind to CD40-bearing cells and to antagonize CD40 mediated activation of various cells[20-27]. ch5D12 was administered in an open label, single dose, multi-centre trial, studying four dose levels. There were five subjects in each treatment group except for the final dose cohort in which only three subjects were enrolled. Single administration at dose levels of 0.3, 1.0, 3.0, and 10.0 mg/kg of ch5D12 was done intravenously. After completing recruitment into one dose group, recruitment into the next group was only started when safety had been established at the current dose level. Clinical disease activity was assessed at each visit weekly for the first 28-day period and a subsequent last visit at day 56. Two subjects (3.0 mg/kg dose cohort) withdrew from the study after the day 28 assessments but their data are included in the evaluation. Subjects were to remain stable on the same dose of their current medication during the course of the study. No un-allowed concomitant medication was used during the study. Response to ch5D12 treatment was defined as a decrease in CDAI of ≥100 points and clinical disease remission was defined as a CDAI of ≤150 (total score) and a decrease of CDAI of at least 100. All subjects who underwent an endoscopy at screening and at day 28 (n=11) were analysed for a decrease in their Crohn's Disease Endoscopic Index of Severity (CDEIS) scoring index. Biopsies were taken from these 11 patients prior to and at day 28 after the ch5D12 administration for histopathology and immunohistochemistry. Safety evaluations included physical examinations, vital signs, ECG, and laboratory data (chemistry, haematology and urinalysis) including, anti-ds-DNA, pANCA, and human anti-chimeric antibody (HACA) evaluations. HACA were determined by enzyme-linked immunosorbent assay (ELISA) as explained in Ref. (27).

Pharmacokinetics

Serum concentrations of ch5D12 were determined by ELISA as previously described[27]. To determine coating of CD40 by the injected ch5D12, blood was collected in heparin tubes and diluted twofold in PBS. Peripheral blood mononuclear cells (PBMC) were isolated by gradient centrifugation (Lymphoprep, Nycomed, Roskilde, Denmark) and 500 000 cells were stained with FITC-labelled ch5D12 and PerCP-labelled anti-$CD_{20}$ (Becton-Dickinson, Mountain View, Calif., USA) and incubated on ice for 30 min. As a background control for 5D12-FITC binding, a separate tube of PBMC was stained only with PerCP-labelled anti-CD20 antibody. Unbound antibodies were washed away, and cells were analysed using a flow cytometer (FACSort; Becton-Dickinson). Acquisition of events was conducted by gating and acquiring CD20-expressing cells for a total of 5000 events. If the number of CD20-expressing cells was lower for a sample set, care was taken to acquire the same number of events in both the unstained and stained preparation.

Histology and Immunohistochemistry

Mucosal biopsies from ileum and colon obtained during ileocolonoscopy prior to treatment on day o and on day 28 with a standard forceps were fixed in formalin 6% for routine analysis. Additional samples were immediately snap-frozen in Tissue-Tek optimum cutting temperature compound (Miles Laboratories Inc, Naperville, Ill., USA) in liquid nitrogen cooled isopentane. Samples were stored at −80° C. until further use. Formalin fixed samples were routinely paraffin processed. Five-micrometer thick sections were prepared and stained with haematoxylin and eosin. The sections were analysed using a Leitz Wetzlar microscope (Wetzler, Germany). A total of four semi-serial sections for each sample were analysed. The frozen samples were used for immunohistochemical analysis, which was performed using a panel of Mabs to assess the presence of different subsets of lymphocytes and monocytes/macrophages. The panel was completed with Mabs directed against CD40 and CD40L. Immunohistochemical staining was performed on cryostat sections, dried overnight at room temperature, and fixed in absolute acetone for 10 min. Re-hydrated slides were incubated for 30 min with the following Mabs; CD3 (clone: UCHT1, 1/10 dilution) (Dako, Glostrup, Denmark), CD4 (clone: MT310, 1/10 dilution) (Dako), CD8 (clone: 144B, 1/20 dilution) (Dako), CD19 (clone: HD37, 1/30 dilution) (Dako), CD40 (clone: 5D12, 1/100 dilution) (PanGenetics, Amsterdam, The Netherlands), CD68 (clone: Kp1, 1/50 dilution) (Dako), CD154 (clone: M90, 1/10 dilution) (Serotec, Oxford, UK). The secondary Mab was a biotin-labelled anti-mouse immunoglobulin (1/400 dilution; Dako) applied for 30 min. To efficiently block endogenous peroxidase, sections were also incubated in methanol solution containing 0.3% (v/v) $H_2O_2$ for 20 min. After three washes with PBS, the avidin/biotin peroxidase-labelled complex (Dako) was added. In between the incubations, the sections were washed in phosphate buffered saline at pH 7 for 15 min. The reaction product was visualized by incubating the section for 10 min in 0.05 m acetate buffer at pH 4.9, containing 0.05% 3-amino-g-ethyl-carbazole (Janssen, Beerse, Belgium) and 0.01% $H_2O_2$, resulting in a bright-red immunoreactive site. Afterwards, the slides were faintly counterstained with Harris haematoxylin, rinsed with distilled water and a cover-slip was applied with glycerol. Controls, which were negative, consisted of an omission of a primary or secondary antibody, use of chromogen alone, and use of irrelevant isotype-matched mouse IgG (vimentin; Dako).

Paraffin sections stained with haematoxylin and eosin, were all analysed by the same pathologist (K. G.) blinded for the origin of the samples. Disease activity was assessed using a histological numerical score[40] of which the maximum activity corresponded to 16. The immunohistochemically stained sections were also analysed in a blinded fashion. For 15 sets of biopsies, positively staining cells were counted in high power fields (magnification×40). The fields were chosen according to the highest density of stromal cells. The number was expressed as a percentage of the total number of mononuclear cells in the stroma. These counts were used for the construction of a scoring system whereby the intensity of the positively staining cells was subdivided into four categories: −, +/−, + and ++. The normal value for CD3+, CD4+, CD8+, CD19+ and CD68+ for both the ileum and colon is +. The normal value for CD40+ and CD154+ cells is negative (−).

Immunologic Safety Parameters

To assess any non-specific immunosuppression by ch5D12, proliferation of peripheral blood T cells in response to the phytohemagglutinin mitogen (PHA) was evaluated. PHA stimulation (1 µg/mL) was performed on isolated PBMC as previously reported.[41] In addition, percentages of circulating CD3+, CD4+, CD8+ and CD20+ cells were measured to exclude depletion of circulating cells. For flow cytometry, blood was collected at indicated times in heparin tubes, of which 100 µL whole blood in each test-tube was stained as follows (all Mabs were purchased from Becton-Dickinson): anti-CD3-FITC, anti-CD19-PE, anti CD45-PerCP, anti-CD45-FITC, anti-CD4-PE, anti-CD8-PE and anti-CD14-PE. The stained cells were then analysed in a FACScan flow cytometer (Becton-Dickinson). This protocol was conducted to calculate the ratio of CD4+ to CD8+ cells and to determine the proportion of B cells within the lymphocytic population. The percentages reported for CD3 and CD19 were percentages of T cells and B cells within the lymphocytic population, whereas, CD4 and CD8 cells were reported as percentages of CD3 cells. Only CD14 (monocytic population) is shown as a percentage of the total CD45 population.

Results

Pharmacokinetics

The mean peak levels of ch5D12 after a single i.v. injection were dose-dependent and dose-proportional (FIG. 1). After 24 h, approximately 50% of the administrated ch5D12 could be detected in serum in the highest three dose cohorts. For the 0.3 mg/kg cohort, only 15% was present in serum after 24 h. From non-human primate studies, a t1/2β of 8-10 days has been calculated[27] which was confirmed by the current human data. Complete coating of CD40 on peripheral blood B cells was not achieved by the infusion of 0.3 mg/kg as determined by an ex vivo competition assay using FITC-labelled ch5D12 (not shown). For the 1.0 mg/kg group, approximately 1 week of coating of CD40 on circulating B cells could be observed, while in the two highest dose groups this period increased to 2-3 weeks. This indicates that in the lowest dose group, antagonism of CD40 was incomplete, while complete antagonism was achieved in the 1.0 mg/kg cohort for 1 week and even longer in the higher dose groups.

Clinical Responses

Figure 2:
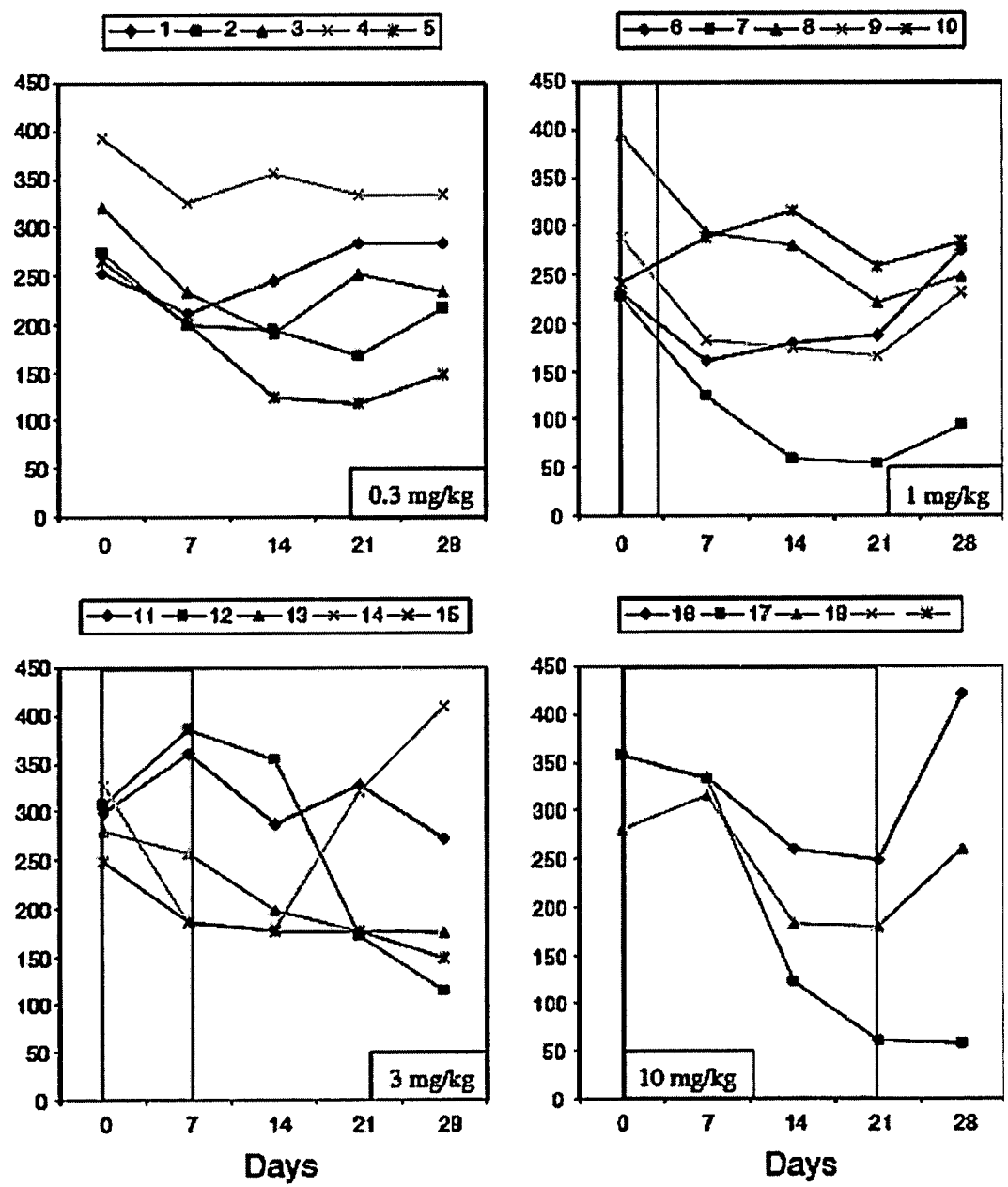
FIG. 2. Changes in Crohn's Disease Activity Index (CDAI) scores during the 28-day period after the ch5D12 infusion. The shaded area indicates the period that ch5D12 levels exceed the 10 µg/mL concentration (see also FIG. 1) which was found to be a functional antagonizing serum level in primates.[24-27] In the 0.3 mg/kg cohort, serum levels never exceeded the 10 µg/mL level.

The analysis of CDAI evolution indicates that 13 of 18 subjects (72%) experienced a favourable response after the ch5D12 infusion. Similarly, four of 18 subjects (22%) experienced a remission during that period. When evaluated at day 21, a favourable response was recorded in 10 of 18 subjects. Cohorts 2 and 4 showed the largest mean decrease in CDAI, and no clear dose-effect relations were observed (FIG. 2; Table 2). A post hoc repeated measure anova showed a statistically significant decrease in CDAI over the 56-day observation period (P<0.001). The difference between the cohorts was not statistically significant. Only in cohorts 3 and 4, CDEIS could be evaluated (as endoscopy was performed in only three subjects in cohort 1 and 2). In cohort 3, two of five subjects had a decrease in CDEIS, whereas in cohort 4, two of three subjects had a decrease. Remaining subjects in these two cohorts showed no change (not shown).

Histological Changes

In the patients from whom biopsies were taken (n=11), a single investigator performed evaluation of changes in histopathology and immunohistochemistry. The assessments performed on biopsy material show a clear influence of treatment upon microscopic activity of the disease as well as upon the intensity of the lamina propria mononuclear cell infiltrate.

Figure 3:
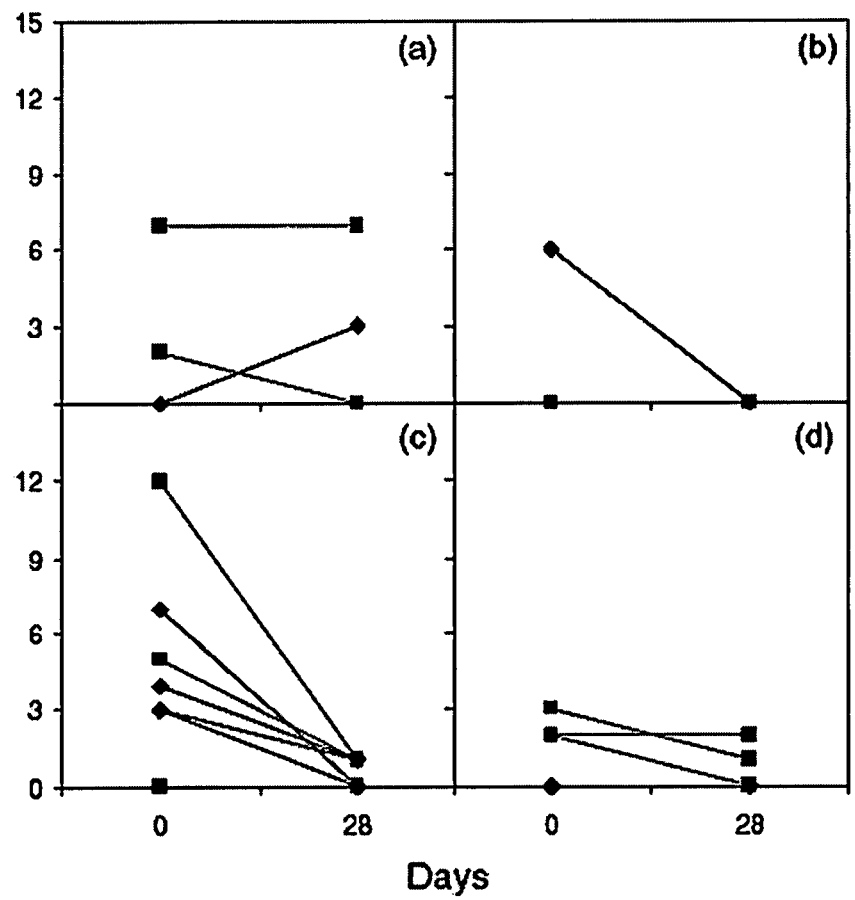
FIG. 3. Histological disease activity scores at day o and day 28. Maximum activity score is 16 and activity score was performed according to Ref.[40] Samples from the ileum (diamonds) from nine subjects and samples from the colon (squares) from 11 subjects were obtained at day o and day 28 and results are presented per dose level of ch5D12 [(a) 0.3 mg/kg; (b), 1.0 mg/kg; (c), 3.0 mg/kg and (d), 10.0 mg/kg].

The change from the baseline to day 28 histopathology activity score is shown in FIG. 3. Samples from the ileum of nine patients and samples from the colon of 11 patients at day o were available. In four cases, the ileum was not involved at screening while five patients had active ileal disease. The mean histology score at day 0 for those with active disease was 4.6 (range 3-7). The mean histology score for the five patients decreased to 1.0 (range 0-3) at day 28. In four of 11 patients, the colon was not involved at day o and the colonic samples from these patients remained normal at day 28. In seven patients the colon was clearly involved with a mean histology score at day 0 of 4.5 (range 2-12). This decreased at day 28 to a mean score of 1.7 (range 0-7). In five of seven patients, the score at day 28 was either 0 indicating a normal biopsy or 1 indicating only architectural abnormalities. In the lowest dose cohort (panel a), the colonic score of one subject decreased, but the other colonic scores in this group remained high and the ileum score even increased. In the higher dose cohorts (panels b-d), either the ileum or colon or both decreased in the activity score at day 28 after treatment with ch5D12. Conclusively, a positive response [as defined in Ref. (41)] was observed in 81% (9/11) of subjects. In addition, seven subjects with active disease at day o showed reduced neutrophil activity to the point that neutrophils were not present in their biopsies at day 28.

To assess which cells were targeted by treatment with ch5D12, an immuno-histochemical evaluation was performed per protocol on the available biopsies using T-cell (CD3, CD4 and CD8) and B-cell (CD19) markers and a macrophage marker (CD68). Results are listed in Table 3. No reduction was observed at day 28 in the lowest dose cohort while in all other cohorts decreased infiltration was observed. In the samples from the ileum at baseline, there was an increased CD3+ T cell number in six of nine cases. In the colon, an increased CD3+ T cell number was present in four of ii patients, all of whom also had active disease on routine histology. At day 28, the CD3+ T-cell numbers had normalized in all but one patient. In this patient (patient 001; lowest dose group; 0.3 mg/kg) there was a persistent CD3+ cell increase in the ileum and colon, in parallel with persistent inflammatory activity and granulomatous inflammation on routine histology. The CD4+ and CD8+ cells followed a similar pattern as CD3+.

The pattern for the CD19+ B cells was comparable with that observed for the T cells. At day o, there was an elevation of B cells in six of nine patients of whom ileal biopsies were available and in four of 11 samples from the colon. At day 28, the amount of the B cells had normalized in all cases except for the one patient from the low-dose group.

A similar decrease on day 28 was observed for CD68+ monocyte/macrophage cells. At day o, there was an increased amount of CD68+ monocyte/macrophage cells in five of nine patients of whom ileal biopsies were available and in four of 11 samples from the colon. Again all increases had normalized on day 28, except for one low-dose cohort patient that remained high for CD68+ monocyte/macrophage cells in the colonic sample and even an increase in the ileac biopsy, showing this patient had still active disease at day 28.

Figure 4:
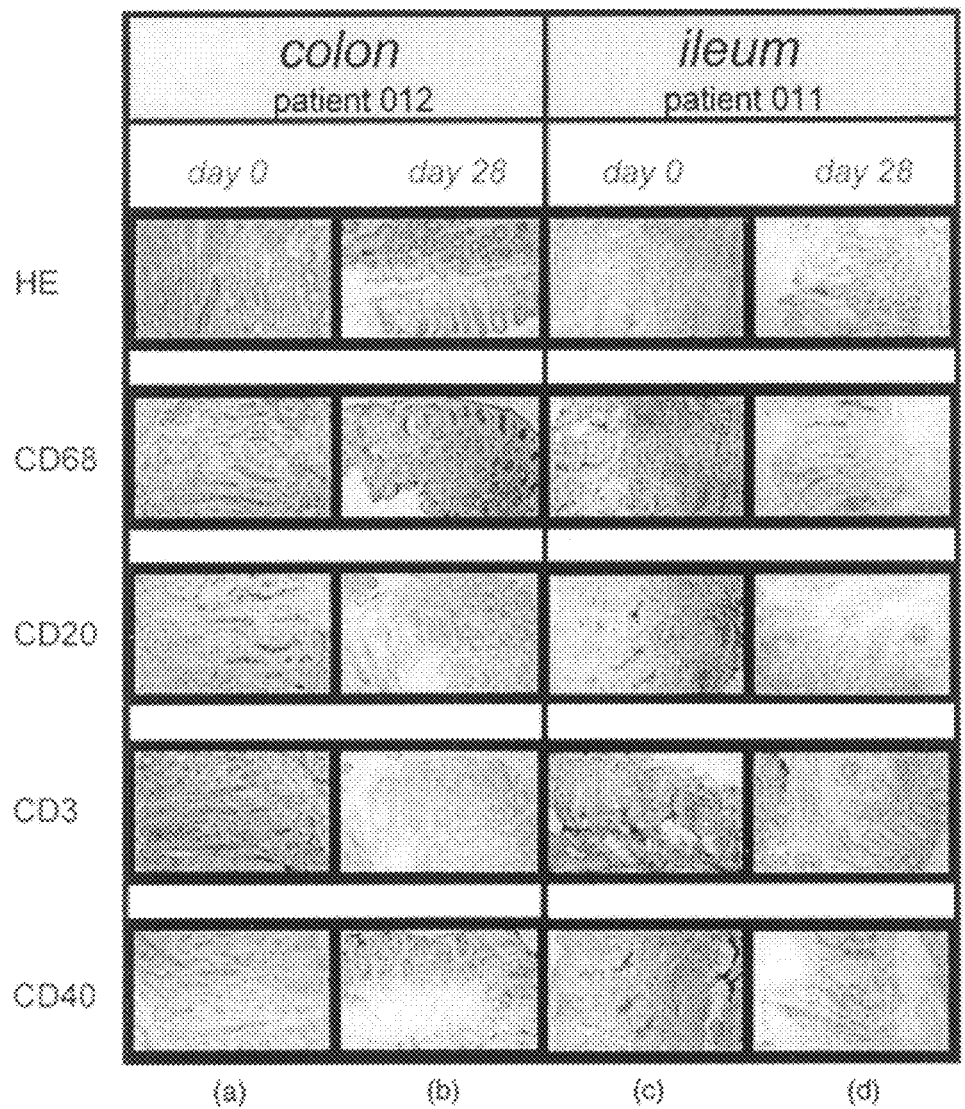
FIG. 4. Colon biopsies from patient 012 (3.0 mg/kg) and ileum biopsies from patient 011 (3.0 mg/kg) are shown as examples for the reduction of the inflammatory response. Samples were stained with antibodies recognizing all T lymphocytes (CD3), B cells (CD19), macrophages (CD68) and CD40(+) cells before (a, c) and on day 28 after ch5D12 administration (b, d). HE, haematoxylin-eosin.

FIG. 4 shows representative examples of the decrease of all three major cell types (T cells, B cells and monocyte/macrophage cells) in ileum biopsies of patient 011 (activity score: 7) and colonic biopsies of patient 012 (activity score: 12) before ch5D12 administration and at day 28 after ch5D12 administration.

Safety

No subjects withdrew from the study because of adverse events (AEs) with the majority of these AEs being mild to moderate in severity. An evaluation of AEs occurring at ≥5% of the total number of AEs revealed the most common AEs being pyrexia, arthralgia, myalgia and headache. Arthralgia, occurring frequently both at baseline and during the follow-up period, decreased in frequency over the course of the follow-up period. Flu-like symptoms and pruritic rashes occurred in four subjects, of whom only one subject experienced a moderate rash starting shortly after study drug administration (3.0 mg/kg). Overall, there is no clear dose response for any single AE, with the possible exception of headache/migraine. There were six serious adverse events (SAEs) noted in six subjects; no events occurred in the 0.3 mg/kg cohort, three events in the 1.0 mg/kg cohort, two events in the 3.0 mg/kg cohort and one event in the 10.0 mg/kg cohort. Five of the six SAEs were considered possibly study drug related, one event was considered not related. All but one event were gastrointestinal events (two sub-ileus both in 1.0 mg/kg; two Crohn's disease aggravated, 1.0 and 3.0 mg/kg subjects; and one abdominal pain aggravated in a 3.0 mg/kg subject). Two of these events however, occurred at such a time-point that a causal relationship to the study drug is very unlikely (one subject on the day of infusion and another subject after undergoing endoscopy 29 days after study drug administration). None of the observed abnormalities appear study drug or dose related.

Immunological Safety Parameters

As ch5D12 inhibits B-cell activation in vitro, total immunoglobulin levels were determined and found to be stable over the course of the follow-up period. To exclude the possibility that ch5D12 is able to deplete B cells from the circulation we performed subset analysis of PBMC over the course of the study. Percentages and absolute numbers of CD3, CD4, CD8 and CD14 positive cells were not affected by ch5D12 administration. Absolute counts of circulating CD19+ B cells transiently decreased shortly after ch5D12 administration and recovered to their original values after ch5D12 had been cleared from the circulation (not shown).

To study whether treatment with ch5D12 would cause a general immune suppressive effect, PBMC isolated at various time-points prior and after treatment were stimulated by the polyclonal T-cell activator PHA. Unfortunately, cells from the 10.0 mg/kg dose cohort were not frozen appropriately and were therefore unable to respond to PHA, including the cells obtained before ch5D12 administration. The stimulation index induced by incubation with PHA was highly variable but no trend towards a decrease after ch5D12 treatment was detected (data not shown).

Anti-ch5D12 antibodies were not detectable in the two lower dose cohorts throughout the entire study. In the 3.0 mg/kg cohort, one subject was found to have mounted an anti-ch5D12 response, although the signal was very low and could only be detected in the undiluted day 28 sample of this patient. In the highest dose group, another subject had anti-ch5D12 antibodies on day 28 and day 56 of the study. These could be detected with a 1:64 dilution. Therefore, only two subjects had a possible immune response to ch5D12 administration.

Discussion

In this open label, multi-centre trial, four dose levels of ch5D12 were administrated to subjects with moderate to severe Crohn's disease. Eighteen subjects were enrolled, with five subjects in each treatment group except for the final dose cohort in which only three subjects were enrolled. ch5D12 serum levels increased dose-dependently and the long serum half-life that was observed in cynomolgus monkeys[27] was confirmed in humans. This study shows the feasibility of antagonizing CD40-mediated cell activation using ch5D12, in the absence of major side effects. The CDAI analysis indicates that 72% of subjects experienced a clinical response and 22% experienced a remission during the study. These results are promising; however the open-label design and the absence of a control group make it impossible to definitely attribute the observed changes to administration of the study drug. However, we do have several arguments in favour of anti-inflammatory effect of ch5D12. First, the observed decrease in CDEIS amongst subjects in the two highest dose cohorts supports treatment efficacy. Secondly, the results of the histological and immunohistochemistry analyses done on biopsies, show that ch5D12 reduces inflammatory activity in colon or ileum. In the low-dose cohort no clear effect was observed. Subjects in the 10.0 mg/kg cohort had the lowest histological activity scores at day o and the reduction in activity score is therefore limited in this cohort. The highest scores at baseline were found in the 1.0 mg/kg and the 3.0 mg/kg groups and in these patients there was a clear reduction in histological scores at day 28.

Although two patients were identified having anti-ch5D12 antibodies in the current study, the levels of HACA antibodies remained very low and were only detectable at very low serum dilutions. It remains to be established whether anti-ch5D12 responses will be detected in subsequent studies.

This trial represents the first administration of anti-CD40 Mab in general and of ch5D12 in particular to humans. However, evidence of biological activity of Mab 5D12 has previously been obtained in vivo in the experimental autoimmune encephalomyelitis (EAE) model in marmoset monkeys. Administration of 5D12 starting 2-4 weeks after induction of disease had clear beneficial effects[23]. This in vivo proof of concept initiated recombinant humanization and further development of 5D12. The biological activity of ch5D12 was also evaluated in the marmoset EAE model. At day 50 after MOG-immunization, disease incidence in the placebo group was 100% (50% of the animals were killed because of their severity of EAE), while no disease signs were observed in the ch5D12-treated group[24]. Furthermore ch5D12 has shown functional activity in a rhesus monkey renal transplantation model[25] and when used as immune suppressive strategy to prevent immune responses against adenoviral particles and their products[26]. A tissue cross-reactivity study on human and cynomolgus tissues showed that ch5D12 bound to the cell surface of B cells and DCs in lymphoid organs. No unexpected cross-reactivity was observed on either human or cynomolgus tissues. A safety and tolerability evaluation for ch5D12 was performed in cynomolgus monkeys, in which weekly administration of ch5D12 for 4 weeks was shown to be safe and without any side-effects in all monkeys. In this study, functional evidence was obtained that ch5D12 can prevent B-cell activation and proliferation[27]. Collectively these studies showed that antagonist anti-human CD40 Mab ch5D12 has no unexpected cross-reactivity, is safe, limits immune reactivity in cynomolgus monkeys, and inhibits a prototype chronic inflammatory disease of the central nervous system in marmoset monkeys. Hence, the preclinical assessment supported further development for use in patients.

The CD40-CD154 (CD40L) co-stimulatory pathway has been validated in animal models as a promising clinical target for treatment of autoimmune disease and transplantation rejection.[15] Potentially the CD40-CD154 interaction can be inhibited by targeting either CD40 or CD154. All previous studies have focused on antagonizing CD154, which is selectively expressed on activated T cells and platelets.[8-11] Human clinical studies using an anti-human CD154 Mab have been halted because of thromboembolic events[12-14]. As this anti-CD154 Mab is constructed as a humanized IgG1, which binds extremely well to Fc-receptors, the anti-CD154 Mab may cross-link CD154 to Fc-receptors resulting in the formation of blood clots. Recently, CD40 was reported to be constitutively expressed on platelets and found to be functionally important using soluble CD154 as stimulus for platelet activation. These stimulatory effects that resulted in activation of platelets were abrogated by addition of anti-CD154 or anti-CD40 Mabs[42]. We confirmed the non-stimulatory characteristics of ch5D12 also in experiments with human platelets, as addition of ch5D12 to prestimulated platelets using sub-optimal concentration of ADP or collagen was without any effect on the activation status of the platelets (M. F. Hoylaerts, unpublished observations, Leuven, Belgium). Furthermore, the $IgG_4$ Fc part of the ch5D12 Mab backbone has reduced capability to bind to Fc-receptors expressed on platelets as compared with an $IgG_1$ backbone. Further discrimination between the two approaches comes from the fact that ch5D12 targets B cells, monocytes, macrophages and DC, while an anti-CD154 Mab targets mainly activated T cells, resulting in markedly different clinical strategies. No indications of thromboembolism in any of the patients treated in this study were observed.

The effect of ch5D12 is largely based on the interference with CD40 mediated cell activation. CD40 triggering induces cytokine and chemokine secretion by macrophages and DC, and enhances the antigen presenting capacity of the latter. As ch5D12 antagonizes the CD40 receptor through which TNF-α production is induced[39], it might also antagonize TNF-α secretion which undoubtedly is an important cytokine in Crohn's disease[43]. However, also a number of other inflammatory cytokines, such as IL-8 and IL-1239, are induced by CD40 triggering and therefore ch5D12 might have anti-inflammatory properties in addition to the prevention of TNF-α production. Whether the effects observed depend mainly on a reduced T-cell activation, or a reduced release of cytokines and chemokines, awaits further investigation.

This first-into-man study with ch5D12 shows promising clinical benefit in the absence of serious side-effects. Further clinical studies will be needed to establish the role and optimal dosing scheme for ch5D12 in maintenance of remissions and in the safety monitoring of multiple infusions. Obviously, therapeutic benefit by antagonizing CD40 will not be limited to Crohn's disease and can potentially be extended to many other inflammatory disorders.

Example 2

Material and Methods

Generation of Chimeric Version of 5D12

Starting from the 5D12 hybridoma cell line the murine variable regions of 5D12 were cloned. Briefly, from lysated cells using Qiagen total RNA was isolated. By RT-PCR using the oligo's 5' CAG GTS MAR CTS SAG SAG TC W GG 3' (SEQ. ID. NO.: 13) and 5' GCA TGT ACT AGT AAT TTT TVT TGT CCA CYT TGG TGC T 3' (SEQ. ID. NO.: 14) to amplify the VH region and using the oligo's 5'CGA TAC GAS MTY CAG CTG ACC CAG TCT CCA 3' (SEQ. ID. NO.: 15) and 5'GAC TCA TCT AGA TAC ACT CAT TCC TGT TGA AGC TCT TG 3' (SEQ. ID. NO.:16) to amplify the VL region of mu5D12. After sequence analysis the consensus sequences for the V regions were determined. Subsequently the V-regions were recloned in pcDNA3002 (Marissen et al, J. of Virol, 2005: 79:4672-4678), together with genomic sequences encoding human $IgG_4$ and human kappa to construct a chimeric $IgG_4$ immunoglobulin expression plasmid.

Generation of Deimmunized Version of 5D12

In collaboration with Biovation using their proprietary DeImmunisation technology within the V regions potential T-cell epitopes were identified. Helper T cell epitopes comprise short amino acid sequences within proteins with the capacity to bind to MHC class II molecules. By removal of the T cell epitopes the antibody can no longer trigger T cell help and the subsequent immunogenicity against it. Identification was done using Peptide Threading. The Peptide Threading approach is a computer-based method for predicting the binding of peptides (small amino acid sequences) to 18 different human MHC class II molecules based on known structures solved by X-ray crystallography. Furthermore an analysis was done to search the V regions for the presence of known human T cell binding peptides from a database (www.wehil. wehi.edu.au).

Based on the primary murine V region amino acid sequences, surface humanized (veneered) V regions were designed. Within these veneered VH sequence 8 potential T-cell epitopes and within the veneered VL region 4 T-cell epitopes were identified. Identified T-cell epitopes were removed by amino acid substitution. Based on this analysis the DNA sequences encoding the deimmunized VH and VL region were synthesized and recloned in the pcDNA3002-$hIgG_4$-kappa expression plasmid.

Site-Directed Mutagenesis

To restore the murine sequences within the VH region of deimmunized pcDNA3002 expression plasmid the Quick-Change Site-Directed Mutagenesis kit of Stratagene was used according to the manufacturer's protocol. In table 4 the used oligonucleotides are shown. Briefly, the plasmid was denatured followed by annealing of the sense and anti-sense primers containing the desired mutation. By cycling (30 sec 95° C.; 30 sec 55° C.; 600 sec 68° C.) for 16 times using a Biometra T gradient PCR machine the mutagenic sequences were incorporated. The non-mutated parental plasmid was digested using DpnI, which only cuts methylated DNA. Subsequently the PCR mixture containing the mutated plasmid was transformed in XL1-Blue competent cells. Colonies were picked and analyzed by DNA sequences for the correct plasmid.

A second set of experiments focused on generating additional variants of positions 29 and 37 specifically by substitution of I for structurally related V or L. In a similar way as described above, plasmids were generated using the oligonucleotides as shown in table 6. Two mutagenesis rounds were required to create double mutants (Table 7). Plasmids were used to transform XL1-blue competent cells.

Expression in PER.C6™

Expression of the various versions of 5D12 was done transiently in PER.C6™ (Crucell). Briefly, the day before the transfection PER.C6™ were trypsinized and counted. Cells were plated in DMEM substituted with 10% FCS at a density of $4 \times 10^5$ cells per well in a T24 well plate. Next day medium was replaced with 0.5 ml fresh medium. For each well 1 µg of plasmid DNA was diluted into 50 µl of OPTI-MEM I, which was combined with equal volume OPTI-MEM I containing 3 µl LipoFectAMINE 2000 (LF2000) reagent (Invitrogen). Mixture was incubated for 20 min at room-temperature to allow DNA-LF2000 reagent complexes to form. Subsequently the DNA-LF2000 reagent complexes (100 µl) were directly added to each well. The transfected cells were incubated at 37° C. in a $CO_2$ incubator. After 48 h the supernatants were analyzed for antibody expression.

ELISA

The amount of expressed antibody was measured by a sandwich ELISA. Briefly, 96 wells EIA/RIA plates (Corning 3590) were coated o/n at 4° C. with polyclonal antibody anti-human IgG (Jackson 109-005-088) diluted 1/1000 in PBS (100 µl/well). After blocking with PBS containing 0.05% Tween and 1% BSA, plates were 3× washes with PBS-0.05% Tween. Subsequently as standard purified chimeric 5D12 was applied in titration starting at 400 ng/ml to zero in triple. Samples (transient supernatants) also applied in titration. All dilutions were done in PBS-0.05% Tween. Plates incubated for 1 hour at 37° C. After 3 times washing 1/5000 diluted detection antibody (anti-human kappa alkaline phosphatase labelled (Southern Biotech Associates 2060-04)) was applied to each well. Plates incubated for 1 hour at 37° C. After removal of incubation plates were 5 times washed. Staining was done with PNP substrate (Sigma N-2765) (1 mg PNP/ml substrate buffer—100 mM Tris/HCl, 100 mM NaCl, 5 mM $MgCl_2.6H_2O$ pH 9.5—). OD405 nm was measured on a BioRad 550 Titertek using 655 nm as reference.

FACS

By FACS analysis the antigen specificity of the expressed antibodies was analyzed. JY cells are EBV transformed human B-cells, which express CD40. Briefly, 100,000 JY cells were incubated with 100 µl supernatant from the transient expression experiment at 4° C. for 20 minutes. To remove unbound antibody cells were washed with PBS containing 0.05% NaAzide and 1% BSA. As secondary antibody 1/100 diluted FITC labeled anti-human IgG (Jackson 109-095-127) was used. After 20 minutes incubation at 4° C. cells were washed. Finally cell samples were measured on a FACScan (BD).

Results

After analysis of several clones the consensus sequence was determined for the murine V regions of 5D12 (FIG. 5).

Figure 6:
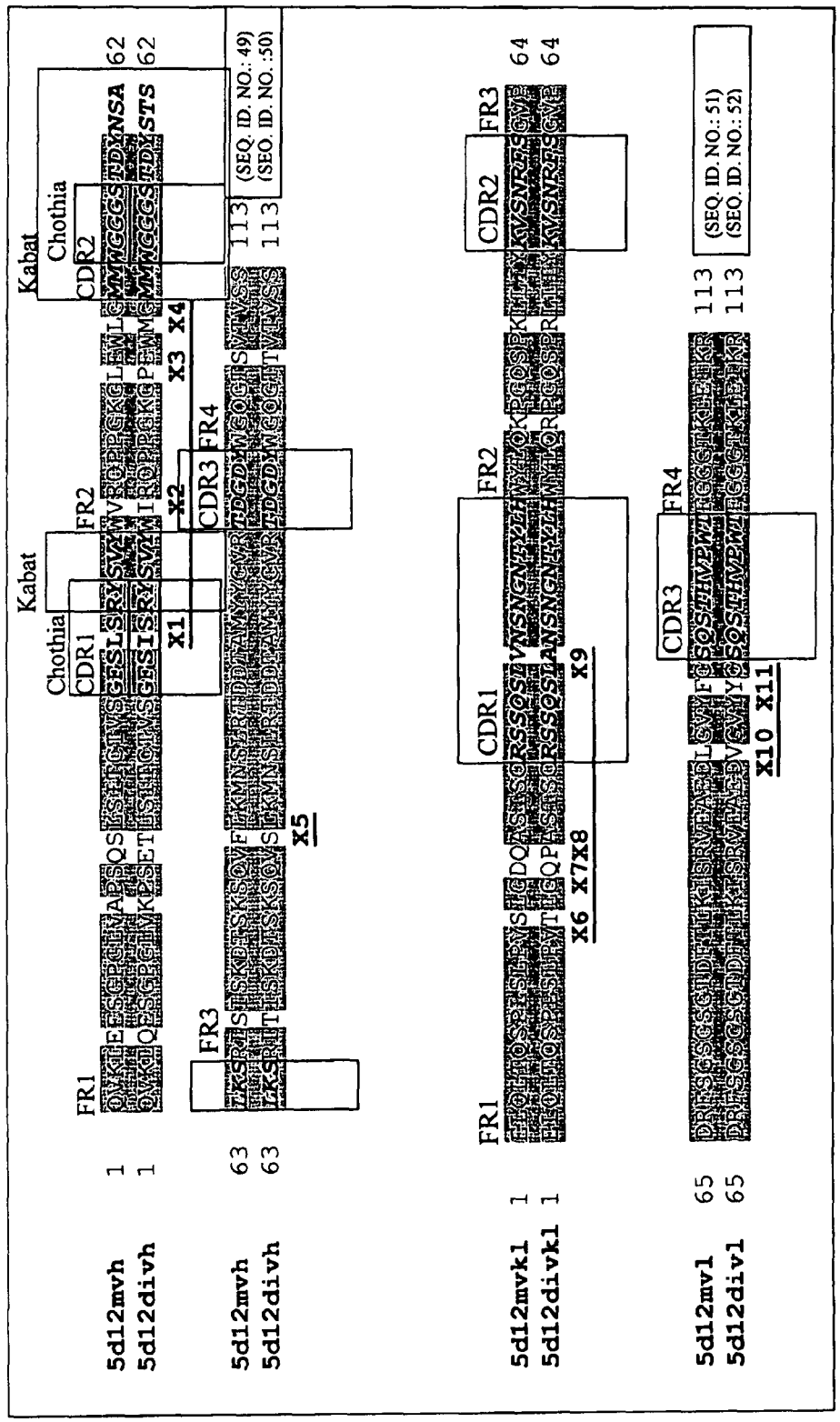
FIG. 6. Amino acid comparison of murine V regions (SEQ ID NO: 51) with veneered and deimmunised V regions of 5D12 (SEQ ID NO: 52).

By human surfacing the V regions were redesigned, retaining critical murine amino acids. By the Peptide Threading method and the database search potential T-cell epitopes within these redesigned sequences were determined. Within the VH region 8 (first base of potential epitope: position 27, 30, 43, 46, 57, 61, 77 and 83) and within the VL region 4 (position 7, 13, 28 and 86) potential epitopes were identified. Based on the T-cell epitope mapping and the veneering process the optimal deimmunized VH and VL amino acid sequences were defined (FIG. 6). To remove the T-cell epitope at position 61 in the VH region special attention was taken not to introduce a potential N-glycosylation site (N—X-T/S): NSA was substituted with STS. In this final design 12 positions in the VH region were changed (counting position 60-62 as 1 change). For the VL region 8 positions were changed.

From preliminary experiments comparing the expression levels of fully deimmunized 5D12 (DI5D12) compared to ch5D12 (renamed PG100) it was found that due to the introduced mutations DI5D12 was expressed at lower levels as compared to the parent sequence (data not shown).

In principal each substitution can influence the characteristics of the expressed antibody. Therefore to investigate the influence of each changed position in the VH region on the characteristics of the antibody 12 additional variants were designed (FIG. 7). In each variant 1 position was changed back to the original murine amino acid sequence.

To test the expression levels and the functionality of the various versions 14 pcDNA3002 expression plasmids were constructed. Each plasmid contains the human IgG$_4$ backbone to which the VH regions were linked and the human kappa region to which the VL regions were linked. One plasmid encoded for ch5D12, in which the murine V regions were used. The other 13 plasmids are deimmunized versions, in which the deimmunized VL region is used in combination with the deimmunized VH region or one of the 12 VH variants shown in FIG. 7. Subsequently PER.C6 cells were transfected with the 14 plasmids using LipoFectamine-2000. Also included were negative mock transfections (no plasmid). After 48 hour the transient supernatants from each transfection were harvested and analysed for antibody expression. In FIG. 8 the FACS data are shown. Clearly all tested constructs bind to JY cells, indicating that the CD40 binding specificity of 5D12 is preserved.

Furthermore the FACS data indicate that the produced antibody levels are different. Clearly there is a difference in expression level between DI5D12 and ch5D12 (PG100). Variants Q5E, K13A, E16Q, T17S, STS60NSA and T68S show the same expression characteristics as DI5D12. The other variants seem to increase the expression levels. To exactly determine the various expression levels, all supernatants were analysed by quantitative ELISA measuring antibody levels. As shown in table 5, the tested variants can be divided in 3 groups: no or low improvement on the expression level (Q5E, K13A, E16Q, T17S and STS60NSA), variants P45L, M48L, S79F and T108S restore the expression levels as compared with ch5D12 (PG100) up to 40%, while the I29L and I37V variants restore the level above 50%. Especially the substitution at position 29 (I to L) seems to have large influence on the expression levels. The I29L variant was subsequently renamed PG102 antibody.

The observation that substitution at position 29 (I to L) and 37 (I to V) both have large influence on the expression levels was among others unexpected because amino acids I, L and V are structurally closely related and the 3 together form the group of branched-chain amino acids. In a subsequent study it was further established what the effect of combined substitutions of the amino acids I at positions 29 and 37 with structurally related amino acids V or L was. FIG. 9 shows the V-L-I variants that were designed in alignment with ch5D12 (PG100), DI5D12 and PG102 (I29L variant).

To test the expression levels and the functionality of these V-L-I variants, additional pcDNA3002 expression plasmids were constructed that contain the human IgG$_4$ backbone to which the VH region of one of the variants was linked and the human kappa region to which the VL regions were linked, as described above. Subsequently PER.C6™ cells were transfected with the plasmids using LipoFectamine-2000. After 48 hour the transient supernatants from each transfection were harvested and analysed for antibody expression. To exactly determine the various expression levels, all supernatants were analysed by quantitative ELISA measuring antibody levels. As shown in table 8, the various combinations of a V, L or I on positions 29 and 37 are associated with variable production levels. This further demonstrates that not just all V, L and I substitutions ultimately lead to higher production levels.

Discussion

By reducing the immunogenicity of a therapeutic antibody the characteristics can change. In this study it is shown that the deimmunization design result in an antibody which still has binding capacity to its antigen, however the antibody could only be produced at low levels. Most probably upon expression there is a problem in the assembly of the deimmunized VH and VL region. By changing each substituted position back to the original murine sequence within the VH region, it was revealed that some positions were essential for a proper expression of the antibody. Especially the sites which were based on the peptide threading approach had large influence on the expression level. The N-terminal changes, all introduced based on veneering had little influence. Remarkably the substitution of I by L in position 29 had the largest influence, which was unexpected as both amino acids are structurally closely related. The I29L variant was subsequently renamed PG102 antibody.

Subsequent studies demonstrated that various combinations of a V, L or I at positions 29 and 37 led to variations in production levels, demonstrating that although the 3 branched-chain amino acids V, L and I are structurally closely related, substitution of each of these on positions 29 and 37 has an impact on production levels of the complete antibodies.

Example 3

Materials and Methods

Construction, selection and development of a GS-CHO cell line for the production of PG102 (I29L variant).

Lonza Biologics (lonza) was requested by PanGenetics BV to undertake the construction, selection and evaluation of a GS-CHO cell line expressing the human recombinant IgG$_4$/kappa antibody PG102 (I29L variant). Cell lines were constructed by transfecting CHOK1SV host cells with vectors generated using Lonza's Glutamine Synthetase (GS) Gene Expression System (WO2003054172). The gene sequences were supplied by PanGenetics. The cell line CHOK1SV is a suspension variant of the Chinese hamster ovary (CHO) cell line CHOK1, which has been adapted to chemically defined, animal component-free (CDACF) medium (Bebbington et al (1192) Biotechnology 10:169-75; de la Cruz Edmonds M C et al (2006) Mol. Biotechnol. 34:179-90).

All reagents, media components and materials were obtained from accredited suppliers. The formulation of the feeds SF40 and SF41, medium CM42, and the medium supplement SPE were obtained from Lonza. The medium CD-CHO (Invitrogen) was also used with the addition of selective agent L-methionine sulphoximine (MSX) for routine subculture of CDACF adapted cell lines and with Phenol Red for transfection. The selective agent MSX was supplied by Sigma. These media and feeds do not contain antibiotics.

The construction of the GS expression vector encoding the genes for the PG102 was also performed at Lonza. The CHOK1SV host cells were obtained from a vial of Lonza's cryopreserved working cell bank 269-W.

Cell Culture, Concentration and Viability

Cells were revived from vials of cryopreserved stocks by rapidly warming to 37° C. and diluting into approximately 50 mL of growth medium. The cryoprotectants were removed by centrifuging the cells, discarding the supernatant and resuspending the cells in fresh growth medium.

For static culture, cells were grown in T25 flasks with a culture volume of 5 to 15 mL. These static cultures were placed in an incubator at 35.5 to 37.0° C. containing an atmosphere of 10% v/v CO$_2$ in air.

For suspension culture, cultures were expanded in a suitable volume of growth medium and subcultured every 4 days for growth in CDACF medium. The containers used were: 125 mL shake flasks (for a culture volume of 10 to 30 mL), 250 mL shake flasks (for a culture volume of 30 to 50 mL), 500 mL shake flasks (for a culture volume of 50 to 100 mL), 1 L roller bottles (for a culture volume of 100 to 200 mL), or 2 L roller bottles (for a culture volume of 200 to 400 mL). The headspace of each culture was gassed with 5% v/v $CO_2$ in air and the flasks sealed. The cultures were then incubated at 35.5 to 37.0° C. on a shaking platform rotating at 140±5 rpm.

Total and viable cell concentrations were obtained by aseptically removing a sample of culture, staining the non-viable cells with Trypan Blue and microscopic examination using a modified Fuchs-Rosenthal haemocytometer. When appropriate, samples were diluted prior to counting.

Alternatively, the total and viable cell concentrations were determined using a CASY-1 particle counter or a Vi-CELL XR automated cell counter. For the CASY-1 counter, a sample of culture was aseptically removed from each flask, diluted with Casyton buffer and the number of viable and total cells determined. Viable and non-viable cells were distinguished by size. Percentage viability was calculated as the ratio of viable cells to total cells multiplied by 100. For the Vi-CELL XR counter, 0.7 mL of cell culture was aseptically removed and an automated Trypan Blue count was performed. A series of camera pictures and a computer analysis algorithm are used to identify and count the viable and non-viable cells. For all counting methods, percentage viability was calculated as the ratio of viable to total cells multiplied by 100.

Transfection of CHOK1SV Host Cells

On the day of transfection, cells growing in non-selective medium were harvested by centrifugation and resuspended at a concentration of $1.43 \times 10^7$ viable cells/mL. For each transfection, approximately 0.7 mL of the cell suspension and 40 μg of plasmid DNA were added to an electroporation cuvette. The electroporation cuvette was then placed in the electroporation apparatus and a single pulse of 300 V, 900 μF was delivered. Following electroporation, the cells from the cuvette were distributed into 96-well plates at approximately 5000 host cells/well, using the medium CD-CHO/phenol red. The plates were incubated at 35.5 to 37.0° C. in an atmosphere of 10% v/v $CO_2$ in air. The day after transfection, 150 μL of the selective medium CD-CHO/phenol red/66.6 μM MSX, was added to each well. The final concentration of MSX in each well was 50 μM. The plates were monitored to determine when the non-transfected cells died to leave foci of transfected cells. Foci of transfected cells became apparent approximately 3 to 4 weeks after transfection. All the transfectants examined and progressed further came from wells containing only a single colony, as determined by visual assessment.

Assessment of Productivity of Cell Lines in Static Culture

The 96-well plates were incubated for approximately 3 to 4 weeks, following transfection to allow colony formation. The colonies were examined microscopically to verify that they were of a suitable size (covering greater than 60% of the bottom of the well), and that only one colony was present in each well. The culture supernatant was then assayed for antibody production using Lonza's ELISA assay for assembled antibody, described under "assembly ELISA". The percentage confluence of the well was assessed at the time of sampling. The value obtained by dividing the assay result by percentage confluence was used to rank the cell lines.

Cultures of high ranking cell lines were expanded into 24-well plates in the medium CD-CHO/phenol red/25 μM MSX and were left to reach confluence. On reaching confluence, this culture was used to inoculate a T25 flask in the medium CD-CHO/phenol red/25 μM MSX, whilst the remaining culture was re-fed with fresh CD-CHO/phenol red/25 μM MSX, and incubated for a further 14 days. At this point, culture supernatant was collected from the 24-well plates and the antibody concentration was measured using Lonza's ELISA assay for assembled antibody. A selection of the most productive cell lines was made. On reaching confluence in the T25 flasks, the selected cell lines were allowed to multilayer and then re-fed with CD-CHO/25 μM MSX. After feeding, the cultures were returned to the incubator for a further four to seven days until the medium turned orange/yellow again and the cells lifted from the flasks.

Expansion of Cell Lines to CDACF Suspension Culture

Suspension cultures were initiated from confluent T25 flask cultures. The suspension cultures were inoculated at a concentration of 0.05 to $0.2 \times 10^6$ viable cells/mL in 125 mL shake flasks containing CD-CHO/25 μM MSX medium. If the viable cell concentration did not reach $0.05 \times 10^6$ viable cells/mL after a maximum of 14 days in T25 flasks, 15 mL of each culture was automatically progressed into 15 mL of CD-CHO/25 μM MSX in 125 mL shake flasks. The cell lines were then serially subcultured into fresh CD-CHO/25 μM MSX medium, at an inoculation concentration of $0.2 \times 10^6$ viable cells/mL, on a 4 day subculture regime, until acceptable and reproducible growth characteristics were obtained.

Assessment of Growth and Productivity of Cell Lines in Suspension Culture

Fed-Batch Shake Flask Culture

Singlet cultures of each selected cell line were prepared in 500 mL shake flasks with 100 mL of cell suspension using CM42/4×SPE medium. The cultures were inoculated at $0.2 \times 10^6$ viable cells/mL and the headspace of each culture was equilibrated with 5% v/V $CO_2$ in air. The cultures were incubated at 35.5 to 37.0° C. on a shaking platform rotating at 140±5 rpm until the viable cell concentration, post peak, was less than or equal to $0.6 \times 10^6$ viable cells/mL or day 15 was reached ('overgrown'). At this point the cultures were harvested. The cell concentration was determined daily using a Vi-CELL automated cell counter. At a cell concentration of 1.4 to $2.2 \times 10^6$ viable cells/mL, a bolus addition of the nutrient feed SF40 was made. Further bolus additions were made at approximately 24, 48 and 72 hours after the initial addition. A second feed (SF41) was applied once cell concentrations greater than $4.0 \times 10^6$ viable cells/mL were obtained. Samples of cultures were taken at appropriate intervals, centrifuged and the supernatants stored at −20±5° C. until assayed for antibody concentration by Protein A HPLC. Harvest supernatants from each overgrown culture were stored at −20±5° C. The ten overgrown cultures with the highest antibody concentrations were further assessed for quality of the antibody produced. Samples were assessed for aggregate levels using the gel permeation high performance liquid chromatography (GP-HPLC) method before Protein A purification and antibody characterisation by reduced and non-reduced sodium dodecylsulphate poly acrylamide gel electrophoresis (SDS-PAGE) and isoelectric focusing (IEF) analysis and matrix assisted laser desorption ionisation time of flight mass spectrometry (MALDI TOF-MS) oligosaccharide analysis.

Cryopreservation

Cells were cryopreserved at key points throughout the work programme. The cells in growing cultures were recovered by centrifugation and resuspended in a cryopreservation mixture. This consisted of the appropriate growth medium (92.5% v/v) and dimethylsulphoxide (7.5% v/v).

Aliquots of cells were then distributed into labelled vials, each aliquot containing approximately 1.5 mL of cryopreservation medium and approximately 0.5 to $1.5 \times 10^7$ viable cells. The vials were then frozen in an automatic programmable cell freezing machine and subsequently transferred to liquid nitrogen refrigerators.

Generation Number

For each of the selected cell lines, the generation number of the cells was defined as zero at the point the culture was passaged into suspension. The generation number was subsequently calculated at each subculture using a procedure derived from the following equation (rounded down to the nearest 0.5 generation).

$$N_f = N_i + \left\{ \frac{1}{\text{Ln}2} \cdot \text{Ln}\frac{X_f}{X_i} \right\}$$

Where: $N_f$=Generation number at time f
$N_i$=Generation number at time i
$X_f$=Viable cell concentration (cells/mL) at time f
$X_i$=Viable cell concentration (cells/mL) at time i and f>i Data Analysis The time integral of the area under the growth curve (the time integral of the viable cell concentration (IVC); $10^9$ cells.h/L) was calculated by summing the area (approximated to a right angle trapezium) between adjacent cell concentration values. The areas were calculated by multiplying the mean of the two viable cell concentrations (cells/mL) by the elapsed time between the two determinations (h). This method is based on that described by Renard et al. (1988) in Biotechnology Letters 10 (2) pages 91-96.

Where appropriate the overall specific production rate ($q_p$ overall: mg/$10^9$ cells/h) was calculated by linear regression analysis of the antibody concentration (mg/L) against the time integral of viable cell concentration. The slope of this line is equal to $q_p$ overall. The harvest specific production rate ($q_p$ harvest) was calculated by dividing the harvest antibody concentration by the value of the IVC at harvest.

Assembly ELISA

The antibody concentration of supernatant samples was determined using an ELISA that measures assembled human IgG. This involved capture of assembled antibody in samples and standard onto a 96-well plate coated with goat anti-human IgG Fc. Bound antibody was revealed with goat anti-human light chain linked to horseradish peroxidase and the chromogenic substrate tetramethylbenzidine. Colour development was proportional to the mass of antibody present in the sample. The concentration was determined using a standard curve generated using an IgG standard (Lot number L07387/5/2)

Protein A HPLC

Product concentration was quantified by Protein A High Performance Liquid Chromatography (HPLC) on an Agilent 1100 HPLC. Antibody was selectively bound to a POROS Protein A immunodetection column. Unbound material was eluted from the column and the remaining bound antibody was released by decreasing the pH of the solvent. Elution was monitored by absorbance at 280 nm using a multiple-wavelength detector. Antibody was quantified (using Chemstation software) against an antibody standard (Lot L07385/4/10) and corrected for an extinction coefficient of $E_{208\,nm}^{0.1\%}=1.52$.

Protein A Affinity Purification

Gravity fed rmp Protein A Sepharose columns (5 mL) were prepared. The columns were cleaned before use with 6 M guanidine HCl and equilibrated with 50 mM glycine/glycinate-250 mM NaCl buffer, pH 8.0. The pH of the column load material was adjusted to pH 8.0±0.1 before application to the column. The rmp Protein A affinity column was washed with equilibration buffer and eluted with 0.1 M glycine buffer, pH 3.5. The column eluates were neutralised to approximately pH 7.0 with 2 M Tris Base and dialysed against Dulbecco's phosphate buffered saline in preparation for IEF and SDS PAGE analyses.

SDS Page Analysis of Protein A Affinity Purified Antibody

The cell culture samples were prepared for analysis by protein A purification. Electrophoresis was carried out using 4 to 20% precast Novex polyacrylamide gels. For reducing SDS PAGE, samples were reduced using 2-mercaptoethanol and denatured by SDS at pH 8.0. Samples were heated for 2.0±0.5 minutes before they were loaded onto the gel (10 µg per lane). Non-reduced SDS PAGE was performed using the same gels and Novex non-reducing sample buffer (2-mercaptoethanol is not added). Samples were heated for a standard time of 1.0±0.5 minutes before they were loaded onto the gel (4 µg per lane). Following electrophoresis, proteins were visualised by staining for 75 minutes with Coomassie brilliant blue R250 and destained with methanol/acetic acid.

IEF Analysis of Protein A Affinity Purified Antibody

The cell culture samples were prepared for analysis by protein A purification. IEF analysis was carried out using pre-cast agarose IEF gels, pH 3 to pH 10. Approximately 10 µg protein sample per lane was loaded onto the gel and then pre-focused for 70 Vh. After removal of the sample application strip, electrophoresis was continued for 1500 Vh (1500 V, 20 mA, 25 W per gel). The IEF gels were fixed in a trichloroacetic acid:sulphosalisylic acid:methanol solution and then stained with Coomassie Brilliant Blue R250 (Lot numbers of Coomassie Blue 003/L11905/118 and 003/L11905/131). The gels were then destained and dried. (Lot numbers of destain 003/L11905/117 and 003/L11905/121).

GP-HPLC

The GP-HPLC method separates protein components according to their size. Large components, such as protein aggregates, are too large to penetrate the matrix particles to any great extent and therefore eluted from the column ahead of smaller components, such as protein monomer. Smaller components, such as fragments, penetrate the matrix more easily and eluted after the monomer. This technique was therefore used to separate antibody monomer from both aggregates and fragments. The monomeric component was identified by its characteristic retention time and position, relative to calibration markers.

Undiluted samples were injected to give 50 to 250 µg loads where the product concentration was 1 to 5 mg/mL (validated load range of Lonza's assay). The molecular mass range for the GF-250 column was 4 to 400 kDa.

Sample components were detected at 280 nm and peak chromatograms were analysed using Agilent Chemstation software. Integration was performed using the perpendicular drop method for aggregates and tangent skim for fragments. The proportion of sample components was determined by calculation of the peak areas of each component relative to the total integrated peak area.

MALDI TOF-MS Analysis

The oligosaccharide analysis of the PG102 antibody produced by each cell line was performed by MALDI TOF-MS using a Micromass™ MALDI-LR coupled with delayed extraction. The MALDI TOF-MS was operated in reflectron configuration with positive ion mode. The instrument was calibrated using a mixed N-glycan standard.

Antibody was purified from harvest supernatants using a POROS Protein A column. The purified fractions were collected and the disulphide bonds were reduced with dithiothreitol followed by alkylation of the reduced thiols using iodoacetate. Oligosaccharides were released using the enzyme N-glycanase (PNGaseF) and were sandwiched between two layers of super-dihydroxy benzoic acid (super-DHB) matrix on the target plate for MALDI TOF-MS analysis.

Results

Transfection of CHOK1SV Host Cells

The PG102 gene sequence was used by Lonza to constructed the double gene vector pPG102/DGV (not shown) that was used to transfect the CHOK1SV host cell line by electroporation. Six sets of transfections were performed using the vector pPG102/DGV and supernatants of 255 transfectants were screened for antibody production in 96-well plates by assembly ELISA. Detectable antibody levels were produced by 99.6% of the screened transfectants. Forty three high ranking transfectants were selected for further evaluation in 24-well plates.

Expansion of Static Cultures and Suspension Adaptation

Figure 10:
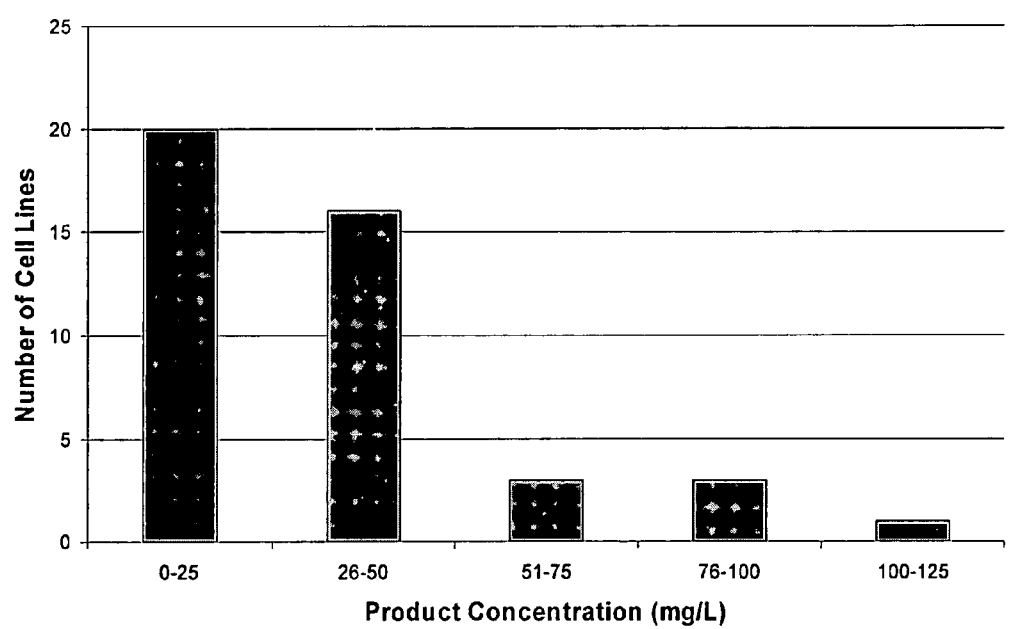
FIG. 10. Distribution of antibody productivity for GS-CHO cell lines producing the PG102 antibody and 'overgrown' 24-well plate cultures. Number of cell lines is plotted on the X-axis, antibody concentration ranges are plotted on the Y-axis (antibody concentration ranges are distributed in ascending groups starting at 0-25 ug/ml).

Cultures of the selected GS-CHO cell lines were first expanded into 24-well plates and then expanded into T25 static flasks. The remaining cells in the 24-well plates were fed with fresh medium and 'overgrown' before assessing the antibody productivity. The selected cell lines displayed a range of antibody concentrations from 8.3 to 120 mg/L (FIG. 10).

Cultures of the 23 cell lines with the highest product concentrations, as determined by assembly ELISA, were selected for further evaluation. The selected cultures were progressed into CDACF medium in suspension culture. All cell lines were successfully adapted to suspension culture and were selected for further evaluation in fed-batch cultures.

Evaluation of the Growth and Productivity Characteristics of Selected Cell Lines in Fed-Batch Shake Flask Culture The growth and productivity characteristics of the 23 selected cell lines were evaluated in fed-batch shake flask culture. Singlet cultures were prepared for each cell line. Two feeds, SF40 and SF41, were added to the cultures when the viable cell concentration met the feeding criteria. The protocol used for the feed regime mimics as closely as technically possible, Lonza's generic GS-CHO fermentation process. Growth and productivity data for the 23 selected cell lines are presented in Table 9. Protein A HPLC analysis of the harvested supernatants of the fed-batch shake flask cultures showed that four cell lines produced antibody concentrations of greater than 1000 mg/L. Cell line L107 produced the highest antibody concentration, 1674 mg/L.

Characterisation of the Antibody Purified From Fed-Batch Shake Flask Culture of Selected Cho Cell Lines Harvest samples of the ten cell lines with the highest antibody concentration were purified using rmp Protein A Sepharose chromatography prior to analysis. The Protein A purified antibodies were then analysed using SDS PAGE and IEF. Visual analysis of the Protein A purified samples analysed by SDS PAGE under non-reducing conditions showed all samples were comparable to each other, exhibiting an intact antibody band at approximately 200 kDa (data not shown). Additional minor bands were visible, although they may not all be visible on the gel image. Three bands with molecular mass between 116 and 200 kDa, one band with a molecular weight between 66 and 97 kDa, one band with a molecular weight between 37 and 55 kDa and two bands with molecular weights between 22 and 31 kDa were also observed. The extra band observed between 66 and 97 kDa is the half antibody, typical of $IgG_4$ antibodies under non-reducing conditions. The same half antibody is also observed in the $IgG_4$ inter assay control (IAC).

Protein A purified samples analysed by SDS PAGE under reducing conditions were also comparable to each other, exhibiting the heavy chain band at approximately 50 kDa and the light chain band at approximately 25 kDa (Data not shown). IEF analysis showed that the integrity of the Protein A purified antibody samples from the selected cell lines demonstrated comparable profiles, with six primary bands (3 major and 3 minor bands) in the pI range 8.15 to 9.30 for all cell lines except L97, M92 and M59. These three cell lines exhibited three major and two minor bands. Additional bands were observed in samples J3 and J4, although these may not all be visible on the gel image.

Oligosaccharide Analysis of Antibody

The oligosaccharide analysis of the antibody produced by each of the ten cell lines selected for further evaluation in fed-batch shake flask cultures was determined by MALDI TOF-MS The predominant oligosaccharide structures in the antibody obtained from the ten cell lines were G0F and G1F, which are typical N-linked oligosaccharide structures observed on antibodies. Relatively low levels of oligomannose structures were detected with the highest level of 6.7% of total glycans measured for antibody derived from cell line L52. Oligomannose-5 (man-5) structures were observed in all samples at a range of 1.1 to 4.6% of total glycans. All of the samples analysed contained comparable levels of oligosaccharides and relatively low concentrations of man-5 (data not shown).

GP-HPLC

When antibody produced by each of the ten cell lines selected for further evaluation was analysed by GP-HPLC, the lower molecular weight components (LMWC) were the least critical but a level of under 25% was preferable. All samples displayed levels of under 25%, with the exception of L52, which displayed a level of 27.1% (Table 10).

Two different calculations of proportions of aggregate would not usually be used, but was deemed necessary as LMWC levels varied so much between samples. Further analysis of the data, excluding the LMWC and looking only at monomer and larger peaks, demonstrated aggregate peak areas of less than 2.2% for all samples (Table 11). Levels of under 5% are considered acceptable.

Selection of Cell Lines

Three cell lines were selected for preparation of pre-seed stocks (PSS). The selection criteria used were a combination of high harvest antibody concentration, acceptable growth characteristics and acceptable product quality characteristics.

Figure 11A:
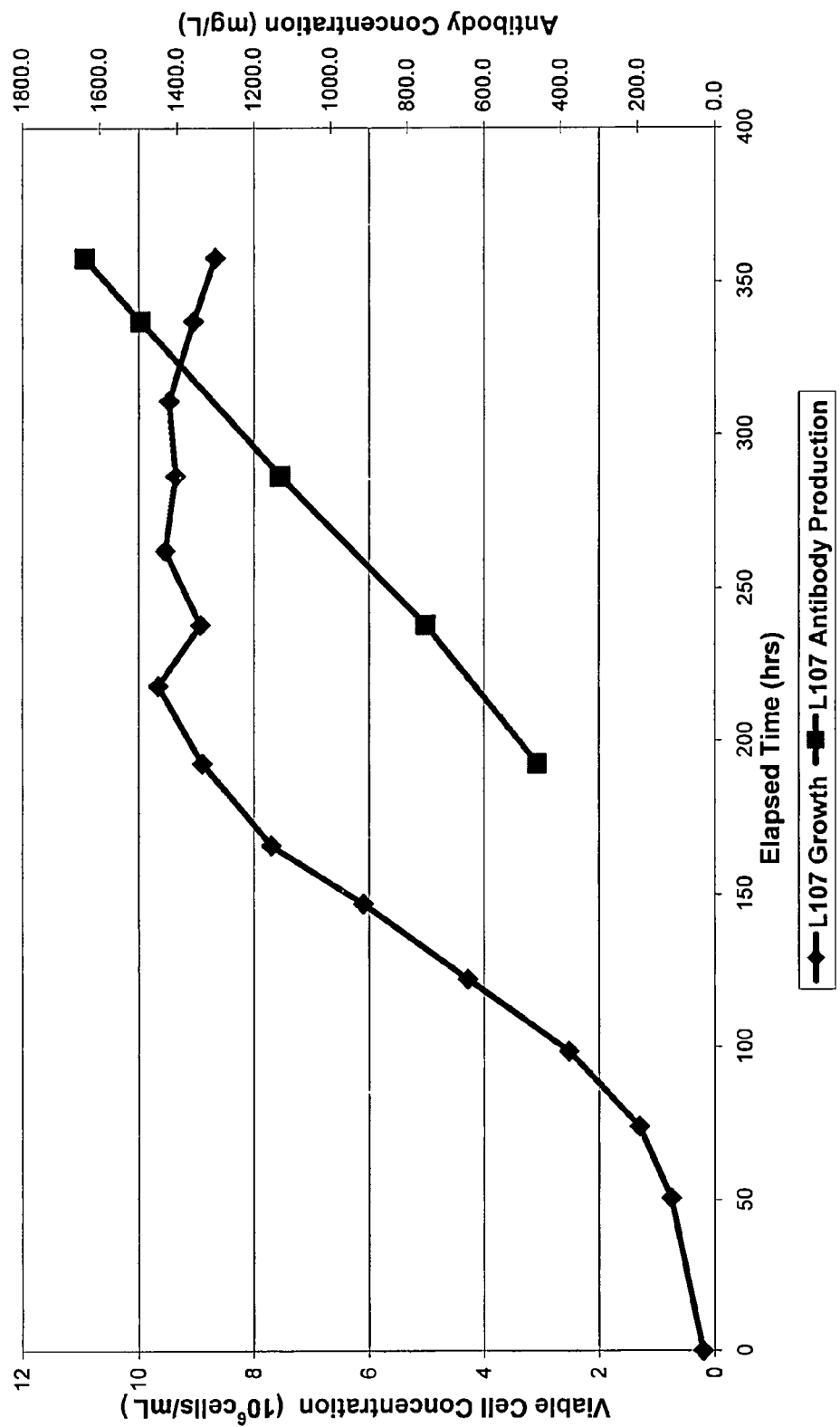
FIG. 11. Growth and antibody accumulation profiles for cell lines A) L107 (DC1; top panel), B) L25 (DC2; middle panel) and C) M95 (DC3; lower panel) in CDACF fed-batch shake flask culture.

Cell line L107 was selected as the lead cell line as it exhibited the highest harvest antibody concentration of the 23 cell lines evaluated, along with acceptable growth and product quality characteristics (FIG. 11A).

Figure 11B:
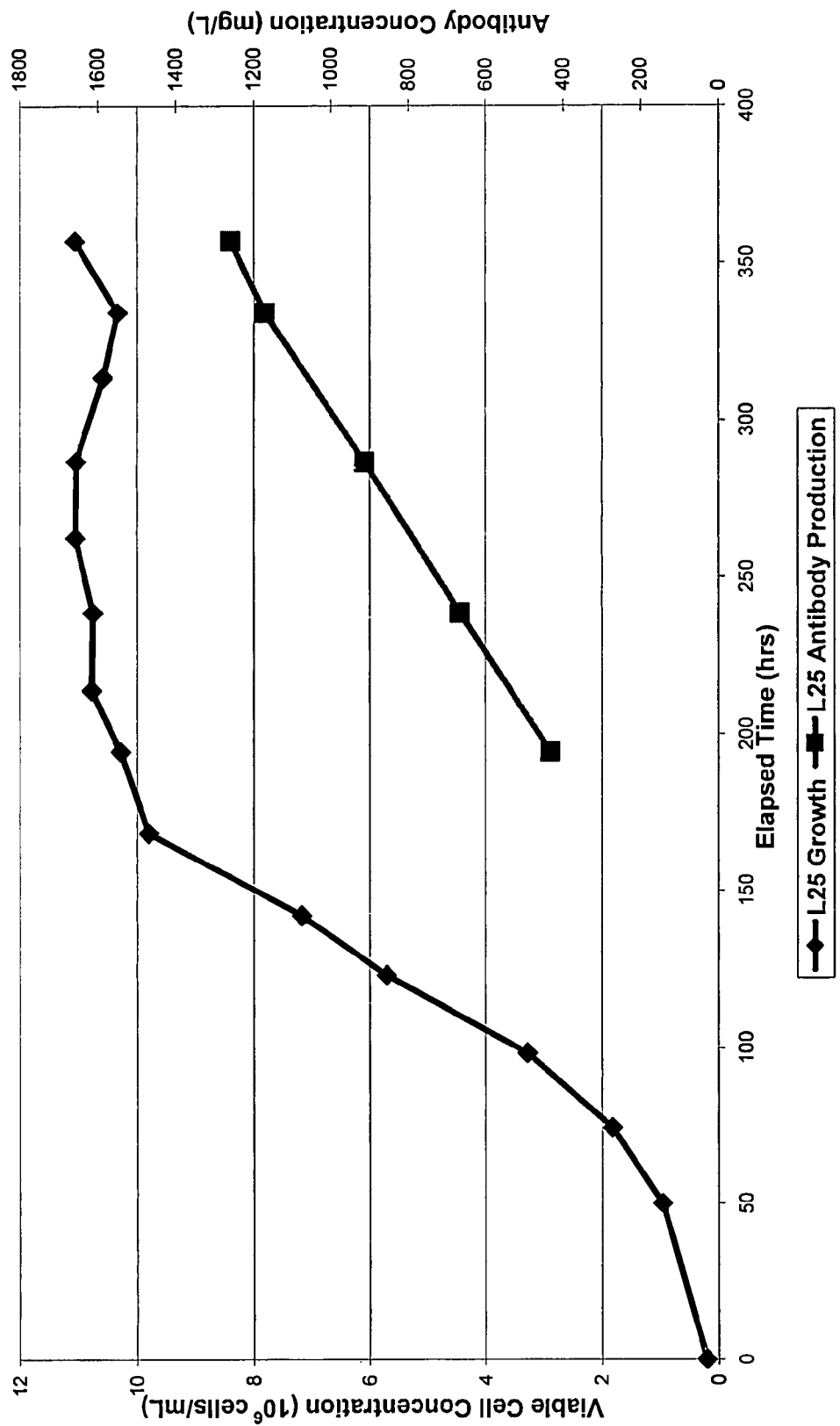

Cell line L25 exhibited the second highest harvest antibody concentration of the twenty three cell lines evaluated, along with acceptable growth and product quality characteristics (FIG. 11B). Therefore cell line L25 was selected as the first back-up cell line.

Figure 11C:
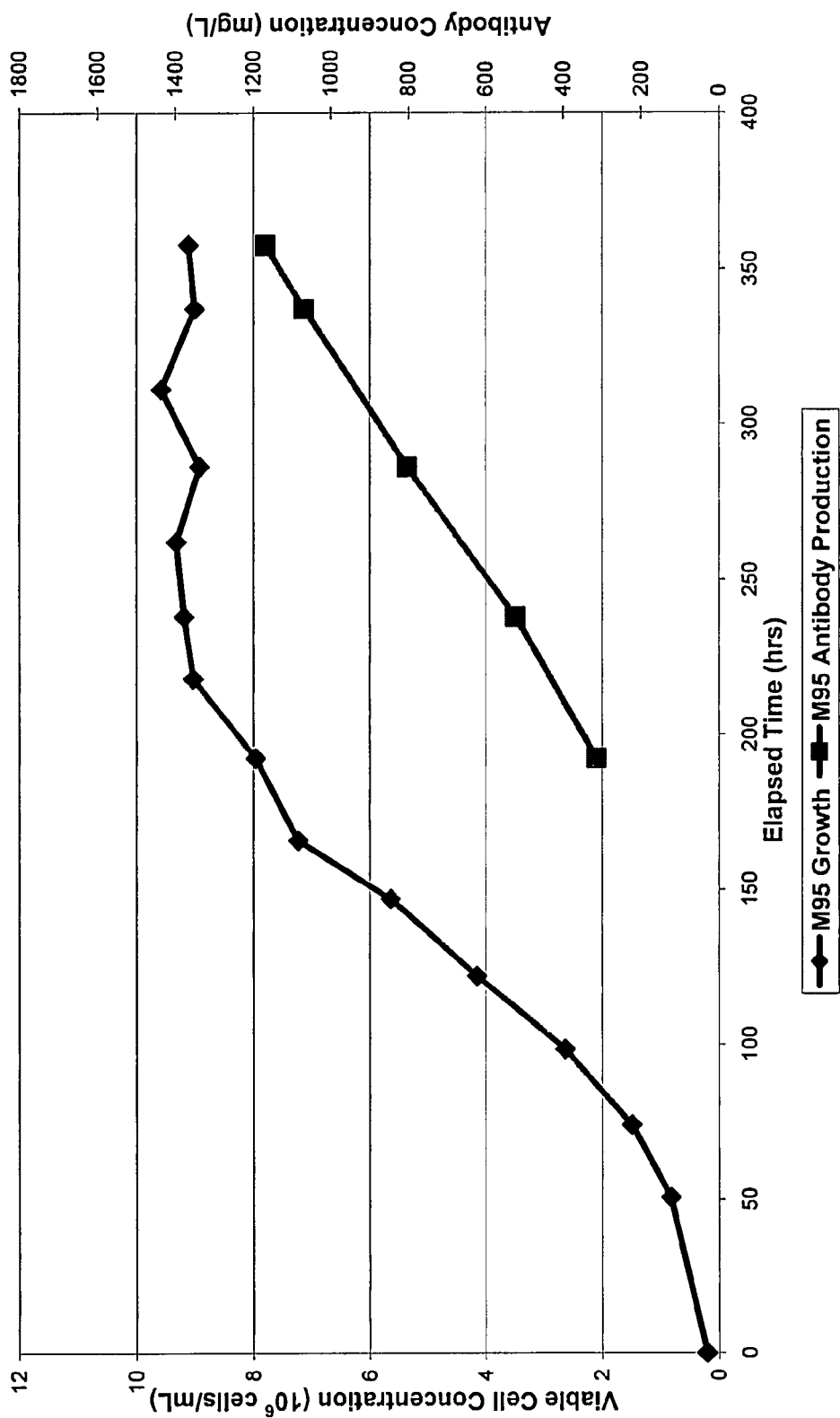

Cell line M95 exhibited the third highest harvest antibody concentration of the twenty three cell lines evaluated, and had acceptable growth and product quality characteristics (FIG. 11C). On this basis cell line M95 was selected as the second back-up cell line.

Cryopreservation of Pre-Seed Stocks

Pre-seed stocks (20 vials per stock) were cryopreserved for each of the three selected cell lines. These stocks were stored in vapour phase liquid nitrogen refrigerators. Cell lines L107, L25 and M95 were renamed DC1, DC2 and DC3 respectively.

Discussion

Lonza Biologics was requested to undertake the construction, selection and evaluation of a GS-CHO cell line expressing the human recombinant $IgG_4$/kappa antibody PG102.

The gene sequence was supplied by PanGenetics and vectors were generated using Lonza's Glutamine Synthetase (GS) Gene Expression System. The cell line CHOK1SV, a suspension variant of the Chinese hamster ovary (CHO) cell line CHO-K1 adapted to chemically defined, animal component-free medium, was transfected by electroporation.

From the CHOK1SV transfections, 254 cell lines were obtained that secreted the antibody. Forty three cell lines were evaluated for growth and productivity in 24-well plates. Antibody concentrations of up to 120 µg/mL were obtained. Twenty three cell lines were evaluated in singlet fed-batch shake flask cultures. Harvest antibody concentrations in the range of 121 to 1674 µg/mL were obtained. Harvest antibody concentrations in excess of 1000 mg/L were achieved for four cell lines. The ten cell lines with highest antibody concentrations were selected for product quality analysis. The product quality of purified antibody from each of the selected cell lines was comparable to each other by reduced and non-reduced sodium dodecylsulphate polyacrylamide gel electrophoresis and isoelectric focusing analysis. Oligosaccharide analysis of purified antibody from each of the ten selected cell lines showed relatively low (<4.6%) levels of oligomannose-5. GP-HPLC analysis showed that aggregate levels were below 1% for each of the top three cell lines.

Three cell lines (L107, L25 and M95) were selected for further evaluation based on growth, productivity and product quality data. Pre-seed stocks of 20 vials of each cell line were cryopreserved. The three cell lines were renamed DC1, DC2 and DC3 respectively.

Example 4

Determination of the Kinetics of ch5D12 (PG100) and PG102 (I29L Variant) Binding to Human Cd40-Fc by Surface Plasmon Resonance (Biacore)

Materials and Methods

The kinetics of ch5D12 (PG100) and PG102 (I29L variant) binding to human CD40 were compared by surface plasmon resonance at a constant temperature of 25.0° C., using a Biacore 3000 instrument. Recombinant human CD40 extracellular domain fused to human IgG1-Fc domain (huCD40-Fc; R&D Systems catalogue number 149-CD-50) was used as the target antigen in these experiments. HuCD40-Fc (1 µg/mL in 10 mM acetate buffer, pH 5.0) was coupled via the amine groups of Lys residues to carbodiimide-activated Biacore CM5 chips, resulting in an antigen immobilization level of 127.4 RU. For kinetic analyses, dilution series of ch5D12 (PG100) and PG102 (range 10.0 µg/mL to 0.313 µg/mL) were prepared in Biacore Running Buffer (HEPES-buffered saline containing EDTA and surfactant; HBS-EP). Kinetic analyses were performed at a flow rate of 30 µL/min. Samples were allowed to bind for 4 min and to dissociate for 5 min, at the same flow rate. The chip surface was then regenerated for 30 seconds using 30 mM NaOH and a baseline re-established in HBS-EP for 2.5 min before injection of the next sample. Alternate samples of PG102 and ch5D12 (PG100) were injected, increasing in concentration for the first set of replicates at each dilution and then decreasing for the second set of replicates.

BIAcore control software (Version 3.2) was used for data collection and BIAevaluation software (Version 4.1) was used for analysis of kinetic data. Binding parameters were calculated using two different models of molecular interaction: a bivalent analyte model and Langmuir 1:1 binding model.

Results

Maximum levels of observed binding for ch5D12 (PG100) and PG102 antibodies were 152.5 RU and 140.2 RU, respectively.

Figure 12:
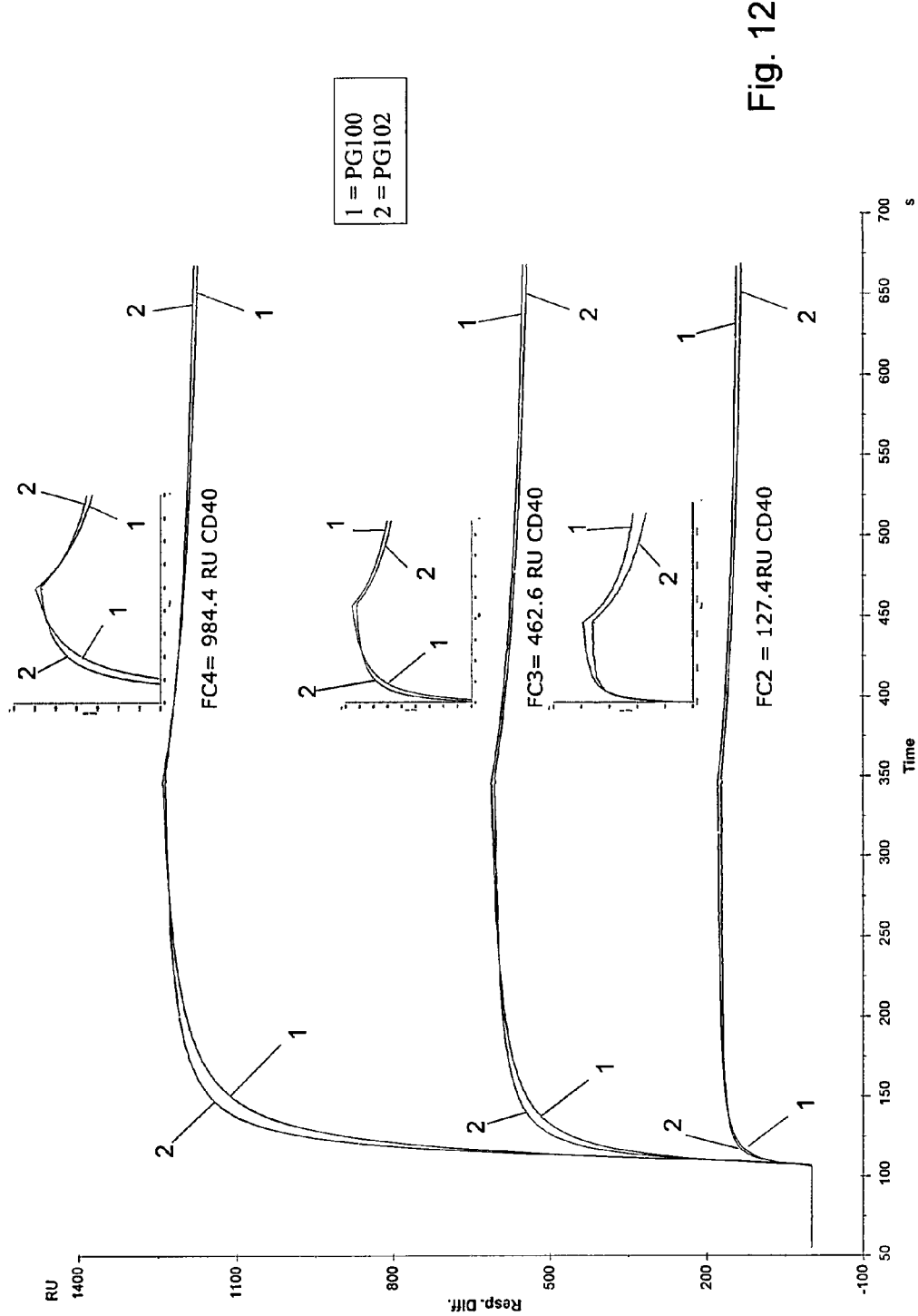
FIG. 12. Comparison of the binding of PG102(red) and ch5D12 (PG100)(blue) at 10 μg/mL to CD40 immobilised at 3 different levels.

The calculated kinetic rate constants according to the Langmuir and bivalent binding models (ka and kd, or ka1 and kd1, respectively) differed slightly for the two antibodies. Thus, PG102 displayed faster association and dissociation rates than ch5D12 (PG100) (FIG. 12), although the overall affinity (KD) of the two antibodies did not differ appreciably within models. Kinetic parameters from these experiments are summarised below:

| Langmuir (1:1) model: | | |
|---|---|---|
| | ch5D12 (PG100) | PG102 |
| ka | $1.88 \times 10^6 \, M^{-1}s^{-1}$ | $2.51 \times 10^6 \, M^{-1}s^{-1}$ |
| kd | $5.07 \times 10^{-4} \, s^{-1}$ | $5.96 \times 10^{-4} \, s^{-1}$ |
| KD | $2.71 \times 10^{-10} \, M$ | $2.37 \times 10^{-10} \, M$ |

| Bivalent binding (1:2) model: | | |
|---|---|---|
| | ch5D12 (PG100) | PG102 |
| ka1 | $6.41 \times 10^5 \, M^{-1}s^{-1}$ | $7.82 \times 10^5 \, M^{-1}s^{-1}$ |
| kd1 | $1.60 \times 10^{-3} \, s^{-1}$ | $2.47 \times 10^{-3} \, s^{-1}$ |
| ka2 | $1.21 \times 10^{-3} \, RUs^{-1}$ | $1.31 \times 10^{-3} \, RUs^{-1}$ |
| kd2 | $2.55 \times 10^{-3} \, s^{-1}$ | $2.24 \times 10^{-3} \, s^{-1}$ |
| KD | $5.29 \times 10^{-9} \, M$ | $5.41 \times 10^{-9} \, M$ |

Analysis of the Goodness of Fit for the two methods indicated that the data is better described by the bivalent binding model.

The calculated affinities of the two antibody variants differed between models, however, the estimates of the dissociation constants (KD) obtained for each antibody with the same model were comparable; $2.71 \times 10^{-10}$ M and $2.37 \times 10^{-10}$ M for ch5D12 (PG100) and PG102 respectively using the Langmuir model and $5.25 \times 10^{-9}$ M and $5.41 \times 10^{-9}$ M using the bivalent analyte model.

Example 5

Inhibition of ch5D12 (PG100) and PG102 Binding to JY Cells Using an Anti-Idiotype Antibody To demonstrate that PG102 (I29L variant) binds to the same epitope of CD40 as its parent molecule ch5D12 (PG100), an anti-idiotypic antibody was used to inhibit binding of PG102 or ch5D12 to CD40-expressing JY cells, measured by FACS.

Materials and Methods

JY cells expressing human CD40 were blocked with 5% human serum for 30 min at room temperature. The anti-idiotype antibody to murine mAb 5D12 (clone 173-36-1) was pre-incubated at varying concentration (0-10 µg/mL) with either ch5D12 (PG100) (1 µg/mL), PG102 (1 µg/mL), or negative control chimaeric anti-huCD86 antibody (chFUN-1; 1 µg/mL) in a total volume of 50 µL/tube and incubated for 15 min. JY cells were washed with FACS buffer (1× PBS, 1% BSA and 0.05% sodium azide) and supernatant was discarded. JY cells were resuspended in FACS buffer to a concentration of $2\times10^6$ cells/mL. 50 μL of the JY cell suspension was added to the pre-incubated antibody mixes to give a final volume of 100 μL/tube. Cells were incubated for 30 min at 4° C. before washing with 4 ml FACS buffer/tube and the supernatant discarded. The cell pellet was resupended in 100 μL of diluted goat-anti-human IgG-FITC (Jackson Immunoresearch Labs. Cat. No. 109-095-127) in FACS buffer (1:100) and incubated for 30 min at 4° C. Cells were washed with 4 ml FACS buffer and supernatant was discarded. The pellet was resuspended in 200 μL FACS buffer and bound antibody was measured using a FACScan flow cytometer (Becton Dickinson).

Results

Figure 13:
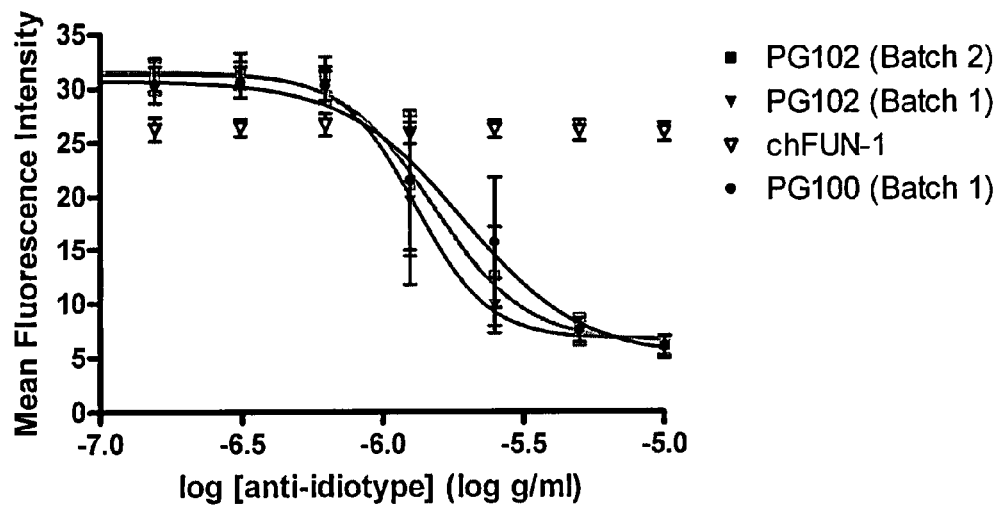
FIG. 13. Inhibition of CD40 mAb binding to JY cells expressing human CD40 by the anti-idiotype mAb 173-36-1. Anti-CD40 mAbs were assayed at a concentration of 1 μg/ml. Data indicate mean±s.e. mean of 4 separate determinations for each antibody.

The anti-idiotype mAb 173-36-1 inhibited PG102 and ch5D12 (PG100) binding to huCD40 expressed on JY cells in a concentration-dependent manner (FIG. 13). The binding of chFUN-1 to CD86 that is also expressed on JY cells was not influenced by mAb 173-36-1. There was no significant difference in the blocking effect of anti-idiotype mAb 173-36-1 on the binding of CD40-specific antibodies to CD40 on JY cells. For example, the calculated log IC50 values for mAb 173-3-1-mediated inhibition of ch5D12 (PG100) (Batch 1) and PG102 (Batch 2) were $-5.74\pm0.14$ and $-5.76\pm0.11$, respectively ($P>0.005$; both n=4). These values correspond to anti-idiotype concentrations of approximately 1.8 μg/mL ($-12$ nM). Table 12 shows a summary of calculated—logIC50 values for anti-idiotype-mediated inhibition of ch5D12 (PG100) and PG102 binding to JY cells.

Example 6

Binding of ch5D12 (PG100) and PG102 to CD-40Fc Determined by ELISA

Material and Methods

ELISA plates (Costar EIA/RIA plate, Corning catalogue number 3590) were coated with 100 μL/well huCD40-muIg (Ancell, catalogue number 504-020), diluted to 250 ng/mL in PBS and incubated overnight at 4° C. in a humid environment. Plates were washed 3 times with 200 μL/well wash buffer (0.05% Tween-20 in PBS). Subsequently, plates were blocked with 200 μL/well blocking buffer (5% BSA Fraction V [Roche, catalogue number 735094] in wash buffer) and incubated for 1 h at 37° C. (humid environment). Plates were washed 3 times with wash buffer. Test antibodies (ch5D12 (PG100), PG102, and negative control chimaeric anti-huCD86 antibody chFUN-1) were diluted in the range 0-1200 ng/mL in blocking buffer and transferred to assay plates in a final volume of 100 μL/well, followed by incubation for 1 h at 37° C. (humid environment). Plates were washed 3 times with wash buffer followed by addition of 100 μl/well goat anti-human kappa-AP detection antibody (Southern Biotech Associates catalogue number 2060-0) diluted 1:1000 in blocking buffer. Plates were incubated for 1 h at 37° C. in a humid environment before washing 3 times with wash buffer and a further single wash with PBS.

PNP substrate was prepared by adding 1 tablet p-Nitrophenyl Phosphate tablets (Sigma, catalogue number N-2765) in 15 mL PNP substrate buffer (12.1 g Tris, 5.84 g NaCl, 1.02 g $MgCl_2.6H_2O$ in 1 L $H_2O$ (adjusted to pH 9.6 with HCl). PNP substrate was added to assay plates at 100 μL/well. Plates were incubated for several minutes (max 30 min) at 37° C. to allow colour development before the reaction was stopped by addition of 3M NaOH. Colour intensity was determined at 405 nm using a micro plate reader (Biorad, model 550).

Results

Figure 14:
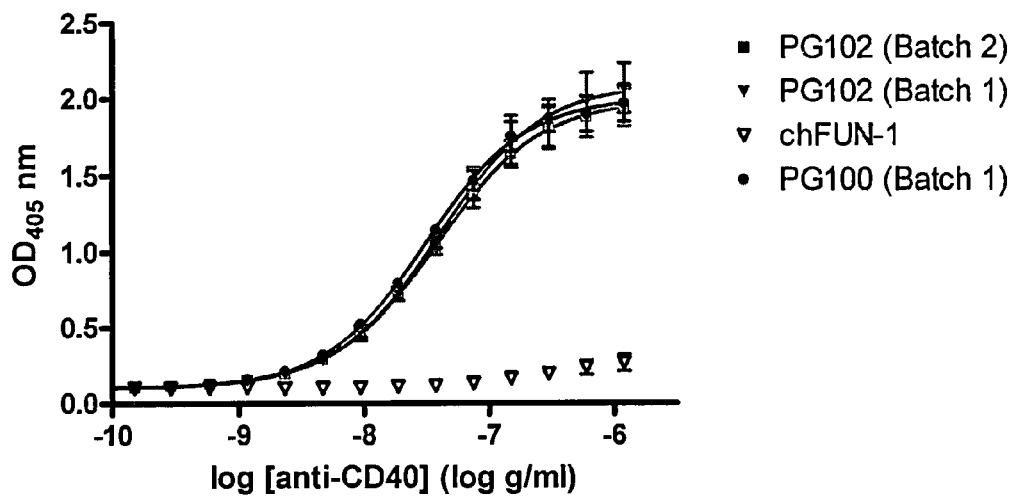
FIG. 14. CD40-Fc ELISA. Concentration-related binding of ch5D12 (PG100) and PG102 to human CD40-Fc. Plates were coated overnight with 250 ng/ml human CD40-Fc. The isotype control mAb, chFUN-1, is directed against human CD86. Data indicate mean±s.e. mean (all n=3).

In a number of independent experiments serially-diluted ch5D12 (PG100) and PG102 (I29L variant) were found to bind comparably to immobilized CD40-Fc (FIG. 14), whilst the anti-CD86 control antibody did not display appreciable binding to CD40-Fc. Calculated half-maximal binding concentrations for all experiments are summarized in Table 13. No significant difference was observed in the half-maximal binding concentration for any of the anti-CD40 antibody batches evaluated.

Example 7

Binding of ch5D12 (PG100) and PG102 to huCD40 Expressed on JY Cells Determined by FACS Materials and Methods CD40-expressing JY cells were washed with FACS buffer (1×PBS, 1% BSA and 0.05% sodium azide). Supernatant was discarded and JY cells were resuspended in FACS buffer to a concentration of $2\times10^6$ cells/mL. Thereafter, 50 μL of the JY cell suspension was added to 50 μL of each of the test antibodies (ch5D12 (PG100), PG102, and negative control chimaeric anti-huCD86 antibody chFUN-1) prepared in the concentration range 0-900 ng/mL and incubated for 30 min at 4° C. Cells were washed with 4 ml FACS buffer/tube and supernatant was discarded. Cell pellets were resuspended in 100 μL of goat anti-human IgG-FITC (Jackson Immunoresearch Labs. Catalogue number 109-095-127) diluted 1:100 in FACS buffer and incubated for 30 min at 4° C. Cells were washed with 4 ml FACS buffer and supernatant was discarded. The pellet was resuspended in 200 μL FACS buffer and bound antibody was measured using a FACScan flow cytometer (Becton Dickinson).

Results

Figure 15:
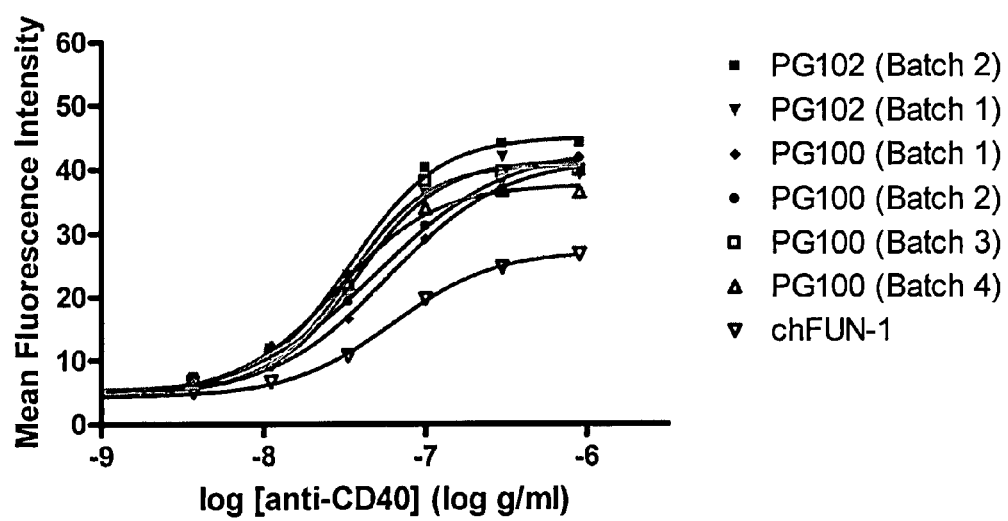
FIG. 15. FACS quantification of anti-CD40 mAb binding to JY cells. ch5D12 (PG100) and PG102 displayed comparable half-maximal binding concentrations. The anti-CD86 mAb, chFUN-1, also showed binding to JY cells in these experiments due to the surface expression of human CD86 by this cell line. Data indicate the mean of duplicate determinations for each antibody.

All tested batches of ch5D12 (PG100) and PG102 showed similar characteristics of binding to CD40 expressed on JY cells (FIG. 15) with comparable half-maximal antibody binding concentrations (Table 14). chFUN-1 also bound to JY cells, albeit with lower mean fluorescence intensity (MFI) than ch5D12 (PG100) and PG102. This is because JY cells also express human CD86.

Discussion

The CD40-binding characteristics of various PG102 (I29L variant) and ch5D12 (PG100) batches have been determined using in vitro cellular and ELISA-based assays. Binding of PG102 and ch5D12 (PG100) to JY cells expressing CD40 was inhibited with equal potency by the anti-idiotype mAb 173-36-1. Thus, the range of calculated mean –log IC50 values for PG102 and CH5D12 (PG100) batches was 5.51 to 6.11 (n=8), and 5.43 to 6.04 (n=10), respectively (p>0.05). Antibody 173-36-1 is directed against the variable regions of the ch5D12 (PG100) precursor, murine mAb 5D12, and did not inhibit binding of an anti-CD86 isotype control antibody. In further experiments the half-maximal binding concentration of PG102 and ch5D12 (PG100) was determined by ELISA analysis of antibody binding to human CD40-Fc, and by FACS analysis of binding to JY cells. In ELISA assays there was no significant difference between the half-maximal binding concentration of PG102 and ch5D12 (PG100) for any batch tested. For example, calculated mean −log half-maximal binding concentrations for the PG102 and ch5D12 (PG100) batches were 7.47±0.04 and 7.54±0.03, respectively (P>0.05, both n=4), corresponding to approximately 30 ng/ml. Similar half-maximal binding concentrations were observed in FACS experiments of PG102 and ch5D12 (PG100) binding to CD40 expressed on JY cells. These results indicate that PG102 and ch5D12 (PG100) share the same CD40-binding paratope, as demonstrated by the comparable potency characteristics of the anti-idiotype antibody for inhibition of PG102 and ch5D12 (PG100) binding to CD40. Furthermore, both antibodies display similar in vitro potencies for binding to human CD40 in ELISA and cell based assays. Together, the data presented suggest that the binding properties of PG102 and ch5D12 (PG100) to human CD40 are the same.

Example 8

Competitive Inhibition of ch5D12 (PG100)-PE and PG102-PE Binding to JY Cells Expressing Human CD40 Using Unlabelled Anti-CD40 Antibody Materials and Methods JY cells (Epstein—Barr virus-transformed human B lymphoblastoid cell line) were grown in Iscove's Modified Dulbecco's Medium (IMDM) containing 10% heat-inactivated foetal calf serum (FCS), 2 mM L-glutamine and 50 μg/mL gentamycin in an air-humidified atmosphere containing 5% $CO_2$, at 37° C. Cells were harvested on the day of flow cytometric measurements.

Unlabelled ch5D12 (PG100) (Batch 4) and PG102 (Batch 2) antibodies were used in these experiments. Both antibodies were also used in PE-labelled form for direct determination of binding to JY cells by flow cytometry. Antibodies were custom-labelled with PE by AbD Serotec (Oxford, UK). For each FACS analysis the following protocol was used. JY cells were harvested from cell culture and counted. Subsequently $1\times10^5$ CD40-expressing JY cells/200 μL incubation buffer (PBS, 1% BSA, 0.05% sodium azide) were incubated with 1 μg/mL labelled ch5D12 (PG100) or PG102 antibodies, in the presence of varying concentration (0-10 μg/mL) of unlabelled competing ch5D12 (PG100) or PG102, for 30 min at 4-8° C. Cells were washed followed by flow cytometric analysis in which the MFI at every concentration was determined using a FACScan flow cyometer (Becton & Dickinson). Five thousand events/sample were measured and analyzed using CellQuest® software (Becton & Dickinson).

Results

Figure 16:
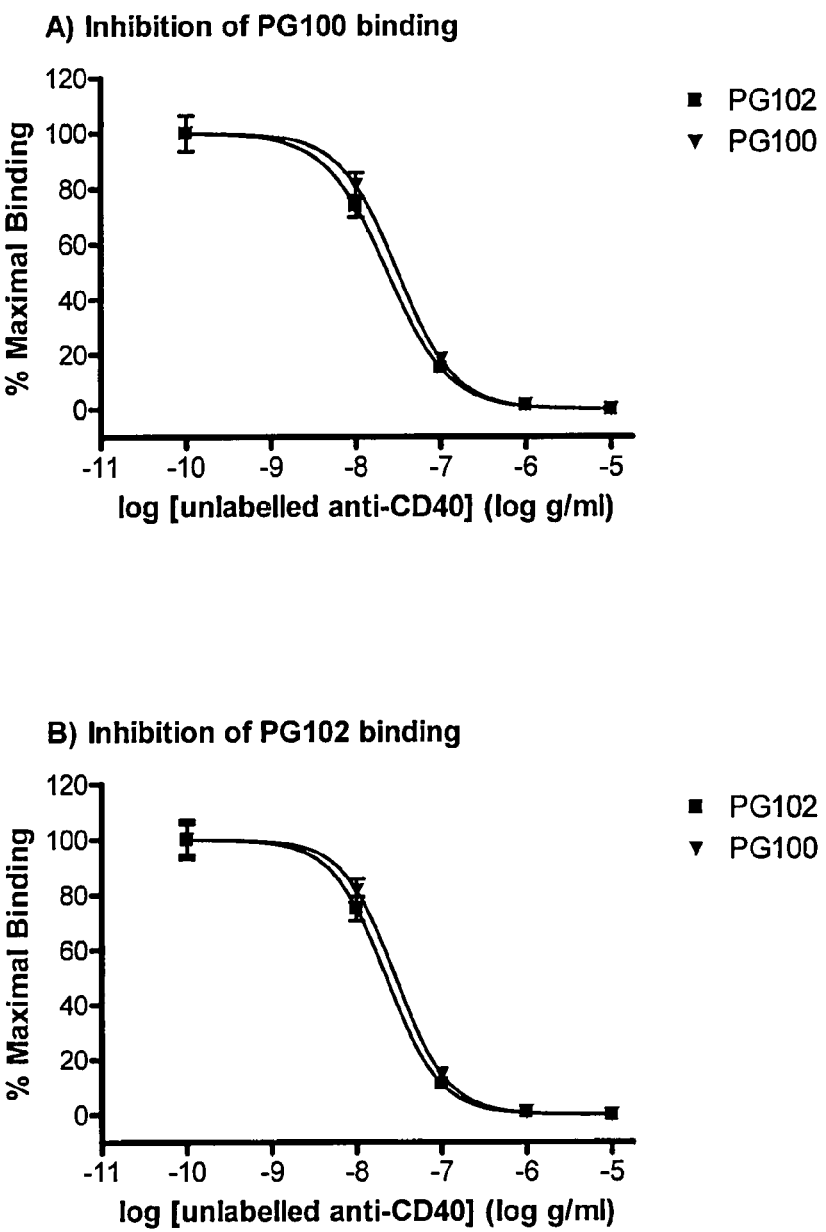
FIG. 16. Inhibition of ch5D12 (PG100)-PE and PG102-PE binding to JY cells by unlabelled ch5D12 (PG100) and PG102 antibodies. Labelled ch5D12 (PG100) (A) and PG102 (B) were incubated at 1 μg/ml in the presence of increasing concentration of competing unlabelled antibody. Labelled antibody binding was determined as mean fluorescence intensity (MFI) by flow cytometry. Maximal MFI for ch5D12 (PG100)PE and PG102PE binding was 369 fluorescence units (A) and 305 fluorescence units (B), respectively. Data indicate mean±s.e. mean of 4 separate experiments.

Unlabelled ch5D12 (PG100) and PG102 antibodies displayed similar inhibitory characteristics in these assays (FIG. 16). Mean −log IC50 values for inhibition of 1 μg/mL ch5D12 (PG100) binding by unlabelled ch5D12 (PG100) and PG102 were 7.50±0.03 and 7.63±0.03, respectively (both n=4), whilst mean −log IC50 values for inhibition of 1 ug/ml PG102 binding by unlabelled ch5D12 (PG100) and PG102 were 7.54±0.01 and 7.65±0.02, respectively (both n=4). These −log IC50 values correspond to PG102 and ch5D12 (PG100) concentrations of approximately 20-30 ng/mL (i.e. ~130-200 pM).

Example 9

Inhibition of IL-8 Release from THP-1 Cells

Materials and Methods

The functionality of PG102 was measured using a cell-based functional bioassay. Briefly, on day 1, THP-1 and Jurkat 39.8/50 human cells were cultured in Iscove's Modified Dulbecco's Medium (IMDM, BioWhittaker, catalogue number BE12-722F supplemented with 10% foetal bovine serum (Gibco, ref 10270-106) and 50 μg/mL gentamycin (Invitrogen, catalogue number 15750-045). THP-1 cells were pulsed with rhuIFN-γ at 1000 units/mL of cell culture.

On day 3 of the bioassay THP-1 and Jurkat 39.8/50 cells were required at a concentration of $4\times10^5$ cells/mL. The THP-1 and J39.8/50 cells were counted and their viability determined. Cells were then diluted to a concentration of approximately $1\times10^6$ cells/mL, Cell suspensions were mixed 1:1 and incubated at 37° C. in a humidified 5% $CO_2$ atmosphere for 48 h.

On day 3 the THP-1 and J39.8/50 cells were washed as follows (In the case of THP-1 cells the wash step was to remove the IFN-γ): 5 mL of IFN-γ pulsed THP-1 and J39.8/50 cell suspension were transferred to a 50 mL falcon tube. 40 mL of Hank's Balanced Salt Solution (HBSS) was added, and the cells were centrifuged at 1500 rpm (using IEC centrifuge) for 6 min. The supernatant was discarded. The cell pellet was resuspended in pre-warmed IMDM supplemented with 10% FCS. The THP-1 cells and J39.8/50 cells were adjusted to a concentration of $4\times10^5$ cells/mL.

For inhibition assays the test sample ch5D12 (PG100) or PG102 (I29L variant) was serially diluted in warmed IMDM medium supplemented with 10% foetal bovine serum to obtain final assay concentrations in the range 0-160 ng/mL. The THP-1, J39.8/50 and test sample(s) were added in triplicate to round bottomed cell culture plates (Nunclon™) in the following order: 50 μL of THP-1 cells (equivalent to $2\times10^4$ cells per well), 50 μL of the test sample and 50 μL J39.8/50 cells. The total volume was 150 μl per well. The cell culture plates were wrapped in porous cling film and incubated at 37° C. in a humidified 5% $CO_2$ atmosphere for 48 h.

On day 5, after a culture period of 48 h, 70 μL of cell culture supernatants were aspirated and transferred to a round bottomed microtitre plate. The harvested cell culture supernatants were assayed for IL-8 content using a commercial ELISA (Biosource, Human IL-8 cytoset, catalogue number CHC1304) in accordance with the manufacturer's instructions.

Results

Figure 17:
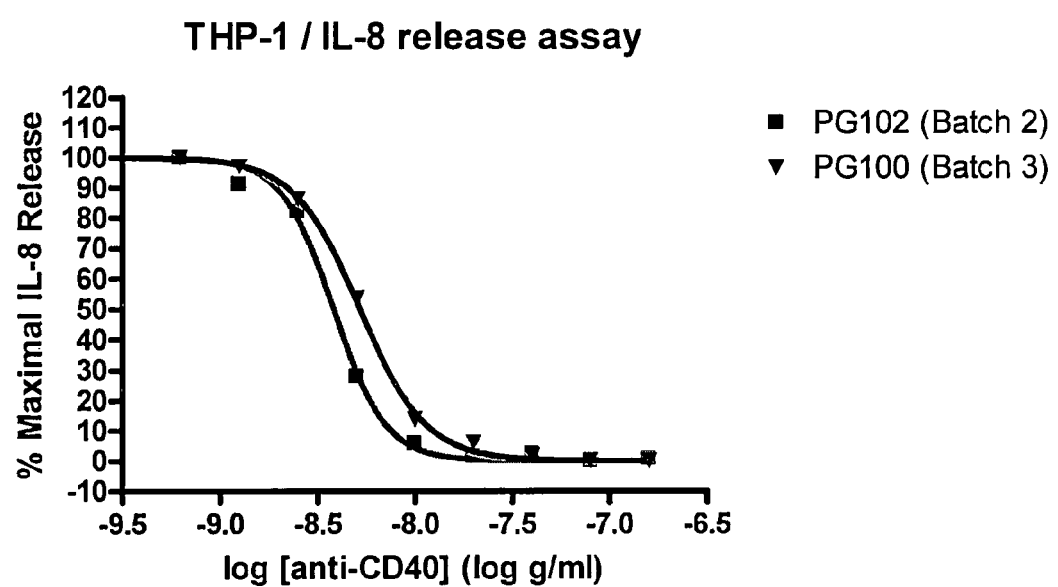
FIG. 17. Inhibition of IL-8 release by THP-1 cells after co-culture with Jurkat cells. THP-1 cells, pulsed with IFN-gamma, are co-cultivated with Jurkat cells in the presence of increasing concentrations ch5D12 (PG100) or PG102. The IL-8 release from THP-1 cells, induced by binding of Jurkat cells to THP-1 cells via CD40-CD40L, was measured by ELISA. Data indicate the result from a single experiment FIG. 18. Nucleic acid and amino acid sequence of an IgG$_4$ PG102 heavy (SEQ ID NO: 78) and light chain (SEQ ID NO: 80).

PG102 (I29l variant) and ch5D12 (PG100) showed similar inhibitory effects on evoked IL-8 release by THP-1 cells (FIG. 17). Calculated −log IC50 values for the two antibodies were 8.42 and 8.28, respectively. These values correspond to IC50 concentrations of approximately 30 μM.

Example 10

A previous tissue cross-reactivity study on human and cynomolgus tissues showed that ch5D12 (PG100) bound to the cell surface of B cells and DCs in lymphoid organs. No unexpected cross-reactivity was observed on either human or cynomolgus tissues. This study was repeated for PG102 and similar results were obtained (data not shown) indicating that ch5D12 (PG100) and PG102 bind to a variety of tissue sections in a similar fashion.

Also a previous safety and tolerability evaluation for ch5D12 was performed in cynomolgus monkeys, in which weekly administration of ch5D12 for 4 weeks was shown to be safe and without any side-effects in all monkeys. In this study, functional evidence was obtained that ch5D12 can prevent B-cell activation and proliferation[27]. Safety studies were repeated for PG102 using a more prolonged protocol. Briefly, a 13 week intravenous toxicity study in cynomolgus monkey with a 14 week recovery period was designed, using 3 dose levels (o, 25 and 100 mg/kg i.v.) and 26 monkeys (6 monkeys (3M, 3F) per treatment group, plus 4 monkeys (2M, 2F) as recovery groups in each active treatment arm). The following measurements were done: TK, anti-PG102 response, flow cytometry (including CD40 coating of PBMC), lymph node biopsy and standard toxicology assessments such as haematology and immunohistochemistry.

The results of this study demonstrated that there is no toxicity observed for any of the dose levels tested. PG102 was safe and well-tolerated.

Collectively these studies demonstrate that antagonist anti-human CD40 Mab PG102, as its parent antibody ch5D12 (PG100), has no unexpected cross-reactivity, and is safe and well tolerated in vivo.

TABLE 1

Baseline demographics by cohort

| Cohort | Dose of ch5D12 (mg/kg) | Gender M/F | Mean age | Mean weight (kg) | Mean length (cm) | Mean BMI | Mean CDAI | Mean CDEIS |
|---|---|---|---|---|---|---|---|---|
| 1 | 0.3 | 1/4 | 30 | 57 | 164 | 21 | 301 | 16 (n = 2) |
| 2 | 1.0 | 2/3 | 43 | 72 | 169 | 25 | 276 | 14 (n = 1) |
| 3 | 3.0 | 1/4 | 34 | 65 | 168 | 23 | 292 | 15 (n = 5) |
| 4 | 10.0 | 3/0 | 34 | 70 | 170 | 24 | 331 | 15 (n = 3) |
| Total | | 7/11 | 35 | 65 | 167 | 23 | 300 | 15 (n = 11) |

BMI, body mass index; CDAI, Crohn's Disease Activity Index; CDEIS, Crohn's Disease Endoscopic Index of Severity.

TABLE 2

Decreases In Crohn's Disease Activity Index scores after ch5D12 treatment

| Subject | CDAI at screening | Decrease in CDAI at day 28 | Max CDAI decrease[a] | Day of max CDAI decrease | Remission (yes/no)[b] | Day of remission |
|---|---|---|---|---|---|---|
| Cohort 1: 0.3 mg/kg ch5D12 | | | | | | |
| 001 | 253 | −30 | 41 | 7 | No | — |
| 002 | 274 | 57 | 107 | 21 | No | — |
| 003 | 320 | 86 | 129 | 14 | No | — |
| 004 | 392 | 58 | 66 | 7 | No | — |
| 005 | 265 | 117 | 149 | 14 | Yes | 14 |
| Mean | 301 | 58 | 98 | 12.6 | | |
| Cohort 2: 1 mg/kg ch5D12 | | | | | | |
| 006 | 232 | −43 | 69 | 7 | No | — |
| 007 | 228 | 133 | 175 | 21 | Yes | 21 |
| 008 | 394 | 144 | 172 | 21 | No | — |
| 009 | 288 | 56 | 123 | 21 | No | — |
| 010[c] | 241 | −42 | No decrease | — | No | — |
| Mean | 277 | 50 | 108 | 14 | | |
| Cohort 3: 3 mg/kg ch5D12 | | | | | | |
| 011 | 299 | 27 | 27 | 28 | No | — |
| 012 | 308 | 194 | 194 | 28 | Yes | 28 |
| 013 | 280 | 106 | 106 | 28 | No | — |
| 014 | 327 | −84 | 147 | 14 | No | — |
| 015 | 249 | 103 | 103 | 28 | No | — |
| Mean | 293 | 69 | 115 | 25.2 | | |
| Cohort 4: 10 mg/kg ch5D12 | | | | | | |
| 016 | 357 | −65 | 109 | 21 | No | — |
| 017 | 358 | 302 | 301 | 28 | Yes | 14 |
| 018 | 280 | 20 | 102 | 21 | No | — |
| Mean | 332 | 86 | 171 | 23.3 | | |

[a]Maximal decrease in CDAI over the 28-day observation period after ch5D12 infusion.
[b]Remission was defined as a total CDAI score of ≤150 and a decrease of >100.
[c]All subjects showed a decrease in their CDAI score except for subject 010 (1.0 mg/kg cohort). This subject had a screening score of 241.4 and the CDAI score never dropped below the value obtained at screening.
CDAI, Crohn's Disease Activity Index.

TABLE 3

| | | | Immunohistochemistry scoring[a] | | | | | | | | |
|---|---|---|---|---|---|---|---|---|---|---|---|
| | | | CD3 | | CD4 | | CD8 | | CD19 | | CD68 | |
| Subject ID | Cohort (mg/kg) | Sample origin | 0 | 28 | 0 | 28 | 0 | 28 | 0 | 28 | 0 | 28 |
| 001 | 0.3 | Ileum | ++ | ++ | ++ | ++ | ++ | ++ | ++ | ++ | + | ++ |
| | | Colon | ++ | ++ | ++ | ++ | ++ | ++ | ++ | ++ | ++ | ++ |
| 005 | 0.3 | Ileum | NS | NS | NS | NS | NS | NS | NS | NS | NS | NS |
| | | Colon | ++ | + | ++ | + | ++ | + | ++ | + | ++ | + |
| 009 | 1.0 | Ileum | ++ | + | ++ | + | ++ | + | ++ | + | ++ | + |
| | | Colon | + | + | + | + | + | + | + | + | + | + |
| 011 | 3.0 | Ileum | ++ | + | ++ | + | ++ | + | ++ | + | ++ | + |
| | | Colon | + | + | + | + | + | + | + | + | + | + |
| 012 | 3.0 | Ileum | ++ | + | ++ | + | ++ | + | ++ | + | ++ | + |
| | | Colon | ++ | + | ++ | + | ++ | + | ++ | + | ++ | + |
| 013 | 3.0 | Ileum | ++ | + | ++ | + | ++ | + | ++ | + | ++ | + |
| | | Colon | + | + | + | + | + | + | + | + | + | + |
| 014 | 3.0 | Ileum | ++ | + | ++ | + | ++ | + | ++ | + | ++ | + |
| | | Colon | + | + | + | + | + | + | + | + | + | + |
| 015 | 3.0 | Ileum | NS | NS | NS | NS | NS | NS | NS | NS | NS | NS |
| | | Colon | + | + | + | + | + | + | + | + | + | + |
| 016 | 10 | Ileum | + | + | + | + | + | + | + | + | + | + |
| | | Colon | + | + | + | + | + | + | + | + | + | + |
| 017 | 10 | Ileum | + | + | + | + | + | + | + | + | + | + |
| | | Colon | + | + | + | + | + | + | + | + | + | + |
| 018 | 10 | Ileum | + | + | + | + | + | + | + | + | + | + |
| | | Colon | ++ | + | ++ | + | ++ | + | ++ | + | ++ | + |

Lymphocyte results: 0 = screening. 28 = day 28.

NS, no sample.

[a] All available biopsies were stained with antibodies recognizing all T lymphocytes (CD3), T-helper cells (CD4), cytotoxic T cells (CD8), B cells (CD19) and macrophages (CD68). The value for CD3+, CD4+, CD8+, CD19+ and CD68+ for both the ileum and colon from non-inflamed tissue is single positive (+).

TABLE 4

| primer | sequence 5'-3' |
|---|---|
| Q5E | ctcccaggttaagcttgaggagtctggacctgg (SEQ. ID. NO.: 17) |
| Q5Erev | ccaggtccagactcctcaagcttaacctgggag (SEQ. ID. NO.: 18) |
| K13A | gacctggcctggtggcaccctcagagaccc (SEQ. ID. NO.: 19) |
| K13Arev | gggtctctgagggtgccaccaggccaggtc (SEQ. ID. NO.: 20) |
| E16Q | cctggtgaaaccctcacagaccctgtccatcac (SEQ. ID. NO.: 21) |
| E16Qrev | gtgatggacagggtctgtgagggtttcaccagg (SEQ. ID. NO.: 22) |
| T17S | gtgaaaccctcagagagcctgtccatcacatgc (SEQ. ID. NO.: 23) |
| T17Srev | gcatgtgatggacaggctctctgagggtttcac (SEQ. ID. NO.: 24) |
| I29L | gcactgtctctgggttctcactctccagatatagtgtatac (SEQ. ID. NO.: 25) |
| I29Lrev | gtatacactatatctggagagtgagaacccagagacagtgc (SEQ. ID. NO.: 26) |
| I37V | gatatagtgtatactgggttcgccagcctccagg (SEQ. ID. NO.: 27) |
| I37Vrev | cctggaggctggcgaacccagtatacactatatc (SEQ. ID. NO.: 28) |
| P45L | cctccaggaaagggtctggagtggatgggaatg (SEQ. ID. NO.: 29) |
| P45Lrev | cattcccatccactccagaccctttcctggagg (SEQ. ID. NO.: 30) |
| M48L | gggtccggagtggctgggaatgatgtg (SEQ. ID. NO.: 31) |
| M48Lrev | cacatcattcccagccactccggaccc (SEQ. ID. NO.: 32) |
| STS60NSA | gtggtggttccacagactataattcagctctcaaatccagactgacc (SEQ. ID. NO.: 33) |
| STS60NSArev | ggtcagtctggatttgagagctgaattatagtctgtggaaccaccac (SEQ. ID. NO.: 34) |

TABLE 4-continued

| primer | sequence 5'-3' |
|---|---|
| T68S | ctcaaatccagactgagcatcagcaaggacacc (SEQ. ID. NO.: 35) |
| T68Srev | ggtgtccttgctgatgctcagtctggatttgag (SEQ. ID. NO.: 36) |
| S79F | cacctcgaagagccaggtcttcttaaaaatgaacagtctgc (SEQ. ID. NO.: 37) |
| S79Frev | gcagactgttcattttaagaagacctggctcttcgaggtg (SEQ. ID. NO.: 38) |
| T108S | gggtcaaggaacctcggtcaccgtctc (SEQ. ID. NO.: 39) |
| T108Srev | gagacggtgaccgaggttccttgaccc (SEQ. ID. NO.: 40) |

Mutagenic oligonudeotides. Oligonucleotides used to introduce the mutations at amino acid postion 5, 13, 16, 17, 29, 37, 45, 48, 60, 68, 79 and 108. For each position is a sense and a antisense ("rev") oligonucletide necessary.

TABLE 5

| variant | FACS MFI | ELISA ng/ml | ratio |
|---|---|---|---|
| Q5E | 39 | 444 | |
| K13A | 31 | 267 | |
| E16Q | 39 | 420 | |
| T17S | 33 | 482 | |
| I29L | 108 | 1331 | |
| I37V | 96 | 1175 | |
| P45L | 82 | 566 | |
| M48L | 80 | 525 | |
| STS60NSA | 62 | 308 | |
| T68S | 35 | 295 | |
| S79F | 96 | 869 | |
| T108S | 99 | 648 | |
| CH5D12 | 103 | 2187 | |
| DI5D12 | 50 | 392 | |
| mock | 11 | n.d. | |
| blank | 10 | n.d. | |

Overview expression data as measured by FACS and quantitative ELISA. For each $_5D_{12}$ variant (Q$_5$E, K$_{13}$A, E$_{16}$Q, T$_{17}$S, I$_{29}$L, I$_{37}$V, P$_{45}$L, M$_{48}$L, STS$_{60}$NSA, T$_{68}$S, S$_{79}$F, and T$_{108}$S) together with ch$_5$D$_{12}$ and DI$_5$D$_{12}$ the MFI value (as determined by FACS) and the antibody concentration in the harvested supernatant (as determined by ELISA) is shown. Also MFI values shown for mock transfection and medium control. Ratio is calculated using the ELISA data compared with ch$_5$D$_{12}$ value (stated as 100%).

TABLE 7

The creation of double mutants required 2 mutagenesis rounds. Below it is listed which primer sets were used in step 1 and step 2 respectively to come to the additional DI5D12 variants.

| Mutant | Step 1 | Step 2 |
|---|---|---|
| PG102 [29L-37I (LI)] | I29L + I29Lrev | n.a. |
| 29I-37V (IV) | I37V + I37Vrev | n.a. |
| 29V-37I (VI) | I29V + I29Vrev | n.a. |
| 29I-37L (IL) | I37L + I37Lrev | n.a. |
| 29V-37V (VV) | I29V + I29Vrev | I37V + I37Vrev |
| 29L-37L (LL) | I29L + I29Lrev | I37L + I37Lrev |
| 29V-37L (VL) | I29V + I29Vrev | I37L + I37Lrev |
| 29L-37V (LV) | I29L + I29Lrev | I37V + I37Vrev |

TABLE 6 mutagenic oligonucleofides. Oligonucleotides used to introduce the mutations at amino acid positions 29 and 37. Sense and antisense (rev) oligonucleotides are listed.

| Primer | sequence 5'-3' |
|---|---|
| I29V | gcactgtctctgggttctcagtctctagatatagtgtatac (SEQ. ID. NO.: 41) |
| I29Vrev | gtatacactatatctagagactgagaacccagagacagtgc (SEQ. ID. NO.: 42) |
| I29L | gcactgtctctgggttctcactctccagatatagtgtatac |
| I29Lrev | gtatacactatatctggagagtgagaacccagagacagtgc |
| I37L | gatatagtgtatactggctgcgccagcctccagg (SEQ. ID. NO.: 43) |
| I37Lrev | cctggaggctggcgcagccagtatacactatatc (SEQ. ID. NO.: 44) |
| I37V | gatatagtgtatactgggttcgccagcctccagg |
| I37Vrev | cctggaggctggcgaacccagtatacactatatc |

TABLE 8

Expression data as measured by quantitative ELISA. For each additional 5D12 variant (29I-37V, 29V-37I, 29I-37L, 29V – 37V, 29L-37L, 29V-37L and 29L-37V), together with ch5D12 (PG100), DI5D12 and PG102 (I29L variant), the antibody concentration in the harvested supernatant is shown.

| variant | name | ELISA (ng/ml) |
|---|---|---|
| 29L-37V | ch5D12 (PG100) | 2846 |
| 29I-37I | DI5D12 | 587 |
| 29L-37I | PG102 | 2226 |
| 29I-37V | | 1728 |
| 29V-37I | | 928 |
| 29I-37L | | 729 |
| 29V-37V | | 2027 |
| 29L-37L | | 1115 |
| 29V-37L | | 891 |
| 29L-37V | | 4263 |

TABLE 9

Summary of growth & productivity data of CHO cell lines in CDACF fed-batch shake flask cultures

| Culture ID | Maximum Viable Cell Concentration $10^6$ cells/mL | Time Integral of Viable Cell Concentration $10^9$ cells · h/L | Product Concentration at Harvest mg/L | Specific Production Rate ($q_P$ harvest) mg/$10^9$ cells/h | Specific Production Rate ($q_P$ overall) mg/$10^9$ cells/h |
|---|---|---|---|---|---|
| L107 (DC1) | 9.66 | 2201 | 1674 | 0.76 | 0.78 |
| L25 (DC2) | 11.06 | 2610 | 1258 | 0.48 | 0.48 |
| M95 (DC3) | 9.58 | 2146 | 1173 | 0.55 | 0.58 |
| L52 | 13.45 | 2989 | 1001 | 0.33 | 0.34 |
| L73 | 5.95 | 1325 | 936 | 0.71 | 0.77 |
| L45 | 10.48 | 2096 | 915 | 0.44 | 0.45 |
| J3 | 9.20 | 2012 | 888 | 0.44 | 0.48 |
| J4 | 11.02 | 2037 | 871 | 0.43 | 0.45 |
| L97 | 7.55 | 1821 | 819 | 0.45 | 0.53 |
| M92 | 7.82 | 1665 | 807 | 0.48 | 0.53 |
| M59 | 14.65 | 3270 | 792 | 0.24 | 0.24 |
| L102 | 6.20 | 1282 | 733 | 0.57 | 0.60 |
| M58 | 8.78 | 1970 | 662 | 0.34 | 0.39 |
| G20 | 5.73 | 1391 | 658 | 0.47 | 0.52 |
| L65 | 3.74 | 878 | 651 | 0.74 | 0.90 |
| L56 | 8.52 | 1728 | 546 | 0.32 | 0.30 |
| M63 | 10.79 | 2465 | 444 | 0.18 | 0.18 |
| G7 | 9.87 | 2058 | 376 | 0.18 | 0.20 |
| G11 | 5.04 | 1145 | 310 | 0.27 | 0.30 |
| L1 | 5.78 | 1163 | 263 | 0.23 | 0.21 |
| M15 | 11.23 | 2654 | 121 | 0.05 | 0.04 |
| M54 | 9.95 | 2278 | 276 | 0.12 | 0.15 |
| M56 | 11.56 | 2347 | 27 | 0.01 | 0.01 |

TABLE 10

GP-HPLC Analysis (including LMWC)

| Sample Number | Culture ID | Relative Peak Area (%) | | | |
|---|---|---|---|---|---|
| | | Total Aggregate | Monomer | Fragment | LMWC |
| 1 | L107 | 0.62 | 84.8 | ND | 14.58 |
| 2 | L25 | 0.65 | 76.5 | ND | 22.88 |
| 3 | M95 | 0.74 | 84.7 | ND | 14.60 |
| 4 | L52 | 0.94 | 72.0 | ND | 27.07 |
| 5 | L73 | 1.48 | 87.9 | ND | 10.63 |
| 6 | J3 | 1.01 | 92.5 | ND | 6.48 |
| 7 | J4 | 1.68 | 73.4 | 0.04 | 24.91 |
| 8 | L97 | 1.66 | 84.4 | ND | 13.92 |
| 9 | M92 | 1.18 | 89.4 | ND | 9.42 |
| 10 | M59 | 1.55 | 84.8 | ND | 13.63 |

ND = Not Detected

TABLE 11

GP-HPLC Analysis (IgG products only)

| Sample Number | Culture ID | Relative Peak Area (%) without LMWC | | |
|---|---|---|---|---|
| | | Total Aggregate | Monomer | Fragment |
| 1 | L107 | 0.72 | 99.3 | ND |
| 2 | L25 | 0.84 | 99.2 | ND |
| 3 | M95 | 0.87 | 99.1 | ND |
| 4 | L52 | 1.28 | 98.7 | ND |
| 5 | L73 | 1.66 | 98.3 | ND |
| 6 | J3 | 1.08 | 98.9 | ND |
| 7 | J4 | 2.24 | 97.7 | 0.05 |
| 8 | L97 | 1.93 | 98.1 | ND |
| 9 | M92 | 1.30 | 98.7 | ND |
| 10 | M59 | 1.79 | 98.2 | ND |

ND = Not Detected

TABLE 12

Summary of calculated −log IC50 values for anti-idiotype-mediated inhibition of ch5D12 (PG100) and PG102 binding to JY cells. Data indicate the mean ± s.e. mean of n determinations. There was no significant difference in the inhibitory potency of the anti-idiotype with any of the antibody batches tested ($p > 0.05$, ANOVA followed by Tukey's test for multiple comparisons).

| Anti-CD40 mAb (batch) | −log IC50 | n |
|---|---|---|
| ch5D12 (PG100) (Batch 1) | 5.74 ± 0.14 | 4 |
| ch5D12 (PG100) (Batch 2) | 5.64 ± 0.01 | 2 |
| ch5D12 (PG100) (Batch 3) | 5.55 ± 0.06 | 2 |
| ch5D12 (PG100) (Batch 4) | 5.63 ± 0.02 | 2 |
| PG102 (Batch 1) | 5.85 ± 0.12 | 4 |
| PG102 (Batch 2) | 5.76 ± 0.11 | 4 |

TABLE 13

Summary of calculated −log half-maximal binding concentration values for ch5D12 (PG100) and PG102 binding to human CD40-Fc, as determined by ELISA. Data indicate the mean ± s.e. mean of n determinations. There was no significant difference in the binding of any antibody batch tested (p > 0.05, ANOVA followed by Tukey's test for multiple comparisons). For reference, a −log half-maximal binding concentration of 7.45 corresponds to a concentration of approximately 35 ng/ml (~200 pmol).

| Anti-CD40 mAb (batch) | −log half-maximal binding concentration | n |
|---|---|---|
| ch5D12 (PG100) (Batch 1) | 7.54 ± 0.03 | 4 |
| ch5D12 (PG100) (Batch 2) | 7.53 ± 0.02 | 2 |
| ch5D12 (PG100) (Batch 3) | 7.48 ± 0.10 | 2 |
| ch5D12 (PG100) (Batch 4) | 7.37 ± 0.10 | 2 |
| PG102 (Batch 1) | 7.45 ± 0.04 | 4 |
| PG102 (Batch 2) | 7.47 ± 0.04 | 4 |

TABLE 14

Summary of calculated −log half-maximal binding concentration values for ch5D12 (PG100) and PG102 binding to JY cells expressing human CD40, as determined by ELISA. Data indicate the mean of duplicate determinations. For reference, a −log half-maximal binding concentration of 7.45 corresponds to a concentration of 35 ng/ml (~200 pmol).

| Anti-CD40 mAb (batch) | −log half-maximal binding concentration | n |
|---|---|---|
| ch5D12 (PG100) (Batch 1) | 7.26 | 2 |
| ch5D12 (PG100) (Batch 2) | 7.34 | 2 |
| ch5D12 (PG100) (Batch 3) | 7.49 | 2 |
| ch5D12 (PG100) (Batch 4) | 7.59 | 2 |
| PG102 (Batch 1) | 7.44 | 2 |
| PG102 (Batch 2) | 7.48 | 2 |

REFERENCES

1 Ranheim E A, Kipps T J. Activated T cells induce expression of B7/BB1 on normal or leukemic B cells through a CD40-dependent signal. J Exp Med (1993); 177: 925-35.

2 Hasbold J, Johnson-Leger C, Atkins C J, Clark E A, Klaus G G B. Properties of mouse CD40: cellular distribution of CD40 and B cell activation by monoclonal anti-mouse CD40 antibodies. Eur J Immunol (1994); 24: 1835-42.

3 Alderson M R, Armitage R J, Tough T W, Strockbine L, Fanslow W C, Spriggs M K. CD40 expression by monocytes: regulation by cytokines and activation of monocytes by the ligand for CD40. J Exp Med (1993); 178: 669-74.

4 Kiener P A, Moran-Davis P, Rankin B M, Wahl A F, Aruffo A, Hollenbaugh D. Stimulation of CD40 with purified soluble gp39 induces proinflammatory responses in human monocytes. J Immunol (1995); 155: 4917-25.

5 Shu U, Kiniwa M, Wu C Y, et al. Activated T cells induce interleukin-12 production by monocytes via CD40-CD40 ligand interaction. Eur J Immunol (1995); 25: 1125-8.

6 Cella M, Scheidegger D, Palmer-Lehmann K, Lane P, Lanzavecchia A, Alber G. Ligation of CD40 on dendritic cells triggers production of high levels of interleukin-12 and enhances T cell stimulatory capacity: T-T help via APC activation. J Exp Med (1996); 184: 747-52.

7 van Kooten C, Banchereau J. Functions of CD40 on B cells, dendritic cells and other cells. Curr Opin Immunol (1997); 9: 330-7.

8 Cayabyab M, Phillips J H, Lanier L L. CD40 preferentially costimulates activation of CD4+ T lymphocytes. J Immunol (1994); 152: 1523-31.

9 Hermann P, Van-Kooten C, Gaillard C, Banchereau J, Blanchard D. CD40 ligand-positive CD8+ T cell clones allow B cell growth and differentiation. Eur J Immunol (1995); 25: 2972-7.

10 Grewal I S, Flavell R A. CD40 and CD154 in cell-mediated immunity. Annu Rev Immunol (1998); 16: 111-35.

11 Henn V, Slupsky J R, Grafe M, et al. CD40 ligand on activated platelets triggers an inflammatory reaction of endothelial cells. Nature (1998); 391: 591-4.

12 van Kooten C, Banchereau J. CD40-CD40 ligand. J Leukoc Biol (2000); 67: 2-17.

13 Clegg C H, Rulffes J T, Haugen H S, et al. Thymus dysfunction and chronic inflammatory disease in gp39 transgenic mice. Int Immunol (1997); 9: 1111-22.

14 Stüber E, Strober W, Neurath M. Blocking the CD40L-CD40 interaction in vivo specifically prevents the priming of T helper 1 cells through the inhibition of interleukin 12 secretion. J Exp Med (1996); 183: 693-8.

15 Liu Z, Geboes K, Colpaert S, et al. Prevention of experimental colitis in SCID mice reconstituted with CD45RBhigh CD4+ T cells by blocking the CD40-CD154 interactions. J Immunol (2000); 164: 6005-14.

16 De Jong Y P, Comiskey M, Kalled S L, et al. Chronic murine colitis is dependent on the CD154/CD40 pathway and can be attenuated by anti-CD154 administration. Gastroenterology (2000); 119: 715-23.

17 Kawai T, Andrews D, Colvin R B, Sachs D H, Cosimi A B. Thromboembolic complications after treatment with monoclonal antibody against CD40 ligand. Nat Med (2000); 6: 114.

18 Buhler L, Alwayn I P, Appel J Z III, Robson S C, Cooper D K. Anti-CD154 monoclonal antibody and thromboembolism. Transplantation (2001); 71: 491.

19 Knosalla C, Gollackner B, Cooper D K. Anti-CD154 monoclonal antibody and thromboembolism revisited. Transplantation (2002); 74: 416-17.

20 de Boer M, Conroy J, Min H Y, Kwekkeboom J. Generation of monoclonal antibodies to human lymphocyte cell surface antigens using insect cells expressing recombinant proteins. J Immunol Meth (1992); 152: 15-23.

21 Kwekkeboom J, de Boer M, Tager J M, de Groot C. CD40 plays an essential role in the activation of human B cells by murine EL4B5 cells. Immunology (1993); 79: 439-44.

22 Kwekkeboom J, de Rijk D, Kasran A, Barcy S, de Groot C, de Boer M. Helper effector function of human T cells stimulated by anti-CD3 Mab can be enhanced by co-stimulatory signals and is partially dependent on CD40-CD40 ligand interaction. Eur J Immunol (1994); 24: 508-17.

23 Laman J D, 't Hart B A, Brok, H P M, et al. Protection of marmoset monkeys against EAE by treatment with a murine antibody blocking CD40 (mu5D12). Eur J Immunol (2002); 32: 2218-28.

24 Boon L, Brok H P M, Bauer J, et al. Prevention of experimental autoimmune encephalomyelitis in the common marmoset (*Callithrix jacchus*) using a chimeric antagonist Mab against human CD40 is associated with altered B-cell responses. J Immunol (2001); 167: 2942-9.

25 Haanstra K G, Ringers J, Sick E A, et al. Prevention of kidney allograft rejection using anti-CD40 and anti-CD86 in primates. Transplantation (2003); 75: 637-43.

26 Haegel-Kronenberger H, Haanstra K, Ziller-Remy C, et al. Inhibition of costimulation allows for repeated systemic administration of adenoviral vector in rhesus monkeys. Gene Ther (2004); 11: 241-52.

27 Boon L, Laman J D, Ortiz-Buijsse A, et al. Preclinical assessment of anti-CD40 Mab 5D12 in cynomolgus monkeys. Toxicology (2002); 174: 53-65.

28 Sartor R B. Pathogenesis and immune mechanisms of chronic inflammatory bowel disease. Am J Gastroenterol (1997); 92: 5S-11S.

29 Fiocchi C. Inflammatory bowel disease: etiology and pathogenesis. Gastroenterology (1998); 15: 182-205.

30 Burgio V L, Fais S, Boirivant M, Perrone A, Pallone F. Peripheral monocyte and naive T-cell recruitment and activation in Crohn's disease. Gastroenterology (1995); 109: 1029-38.

31 Rugtveit J, Brandtzaeg P, Halstensen T S, Fausa O, Scott H. Increased macrophage subset in inflammatory bowel disease: apparent recruitment from peripheral blood monocytes. Gut (1994); 35: 669-74.

32 Fuss I J, Neurath M, Boirivant M, et al. Disparate CD4+ lamina propria (LP) lymphokine secretion profiles in inflammatory bowel disease. J Immunol (1996); 157: 1261-70.

33 Mullin G E, Maycon Z R, Braun-Elwert L, et al. Inflammatory bowel disease mucosal biopsies have specialized lymphokine mRNA profiles. Inflam Bowel Dis (1996); 2: 16-26.

34 Pospai, D, Rene E, Fiasse R, et al. Crohn's disease stable remission after human immunodeficient virus infection. Dig Dis Sci (1998); 43: 412-9.

35 Stronkhorst A, Radema S, Yong S L, et al. CD4 antibody treatment in patients with active Crohn's disease: a phase 1 dose finding study. Gut (1997); 40: 320-7.

36 Sadlack B, Merz H, Schorle H, Schimpl A, Feller A C, Horak I. Ulcerative colitis-like disease in mice with a disrupted interleukin-2 gene. Cell (1993); 75: 253-61.

37 Kuhn R, Lohler J, Rennick D, Rajewsky K, Muller K. Interleukin-10-deficient mice develop chronic enterocolitis. Cell (1993); 75: 263-74.

38 Powrie F, Leach M M, Mauze S, Menon S, Caddle L B, Coffman R A. Inhibition of Th1 responses prevents inflammatory bowel disease in SCID mice reconstituted with CD45RBhi CD4+ T cells. Immunity (1994); 1: 553-62.

39 Liu Z, Colpaert S, D'Haens G R, et al. Hyperexpression of CD40 Ligand (CD154) in inflammatory bowel disease and its role in pathogenic cytokine production. J Immunol (1999); 163: 4049-57.

40 D'Haens G, Geboes K, Peeters M, Baert F, Penninckx F, Rutgeerts P. Early lesions caused by infusion of intestinal contents in excluded ileum in Crohn's disease. Gastroenterology (1998); 114: 262-7.

41 Cornillie F, Shealy D, D'Haens G, et al. Infliximab induces potent anti-inflammatory and local immunomodulatory activity but no systemic immune suppression in patients with Crohn's disease. Aliment Pharmacol Ther (2001); 15: 2041-2.

42 Inwald D P, McDowall A, Peters M J, Callard R E, Klein N J. CD40 is constitutively expressed on platelets and provides a novel mechanism for platelet activation. Circ Res (2003); 92: 1041-8.

43 Van Assche G, Rutgeerts P. Anti-TNF agents in Crohn's disease. Expert Opin Investig Drugs (2000); 9: 103-11.

44 Stüber E, Strober W, Neurath M. Blocking the CD40L-CD40 interaction in vivo specifically prevents the priming of T helper 1 cells through the inhibition of interleukin 12 secretion. J Exp Med (1996); 183:693-698.

45 Ranheim E A, Kipps T J. Activated T cells induce expression of B7/BB1 on normal or leukemic B cells through a CD40-dependent signal. J Exp Med (1993); 177:925-935

46 Hasbold J, Johnson-Leger C, Atkins C J, Clark E A, Klaus G G B. Properties of mouse CD40: cellular distribution of CD40 and B cell activation by monoclonal anti-mouse CD40 antibodies. Eur J Immunol (1994); 24:1835-1842.

47 Alderson M R, Armitage R J, Tough T W, Strockbine L, Fanslow W C, Spriggs M K. CD40 expression by monocytes: regulation by cytokines and activation of monocytes by the ligand for CD40. J Exp Med (1993); 178:669-674.

48 Kiener P A, Moran-Davis P, Rankin B M, Wahl A F, Aruffo A, Hollenbaugh D. Stimulation of CD40 with purified soluble gp39 induces proinflammatory responses in human monocytes. J Immunol (1995); 155:4917-4925.

49 Shu U, Kiniwa M, Wu C Y, Maliszewski C, Vezzio N, Hakimi J, Gately M, Delespesse G. Activated T cells induce interleukin-12 production by monocytes via CD40-CD40 ligand interaction. Eur J Immunol (1995); 25:1125-1128.

50 Cella M, Scheidegger D, Palmer-Lehmann K, Lane P, Lanzavecchia A, Alber G. Ligation of CD40 on dendritic cells triggers production of high levels of interleukin-12 and enhances T cell stimulatory capacity: T-T help via APC activation. J Exp Med (1996); 184:747-752.

51 van Kooten C, Banchereau J. Functions of CD40 on B cells, dendritic cells and other cells. Curr Opin Immunol (1997); 9:330-337.

52 Cayabyab M, Phillips J H, Lanier L L. CD40 preferentially costimulates activation of CD4+ T lymphocytes. J Immunol (1994); 152:1523-1531.

53 Hermann P, Van-Kooten C, Gaillard C, Banchereau J, Blanchard D. CD40 ligand-positive CD8+ T cell clones allow B cell growth and differentiation. Eur J Immunol (1995); 25:2972-2977.

54 Grewal I S, Flavell R A. CD40 and CD154 in cell-mediated immunity. Annu Rev Immunol (1998); 16:111-135.

55 Henn V, Slupsky J R, Grafe M, Anagnostopoulos I, Forster R, Muller-Berghaus G, Kroczek R A. CD40 ligand on activated platelets triggers an inflammatory reaction of endothelial cells. Nature (1998); 391:591-594.

56 Banchereau J, Bazan F, Blanchard D, Briere F, Galizzi J P, van Kooten C, Liu Y J, Saeland S. The CD40 antigen and its ligand. Annu Rev Immunol (1994); 12:881-922.

57 Foy T M, Aruffo A, Bajorath J, Buhlmann J E, Noelle R J. Immune regulation by CD40 and its ligand gp39. Annu Rev Immunol (1996); 14:591-617.

58 Kato T, Hakamada R, Yamane H, Nariuchi H. Induction of IL-12 p40 messenger RNA expression and IL-12 production of macrophages via CD40-CD40 ligand interaction. J Immunol (1996); 156:3932-3938.

59 Ludewig B, Graf D, Gelderblom H R, Becker Y, Kroczek R A, Pauli G. Spontaneous apoptosis of dendritic cells is efficiently inhibited by TRAP (CD40-ligand) and TNF-a, but strongly enhanced by interleukin-10. Eur J Immunol (1995); 25:1943-1950

60 Allen R C, Armitage R J, Conley M E, Rosenblatt H, Jenkins N A, Copeland N G, Bedell M A, Edelhoff S, Disteche C M, Simoneaux D K, Fanshow W C, Belmont J, Spriggs M K. CD40 ligand gene defects responsible for X-linked hyper-IgM syndrome. Science (1993); 259:990-993.

61 Xu J, Foy T M, Laman J D, Elliott E A, Dunn J J, Waldschmidt T J, Elsemore J, Noelle R J, Flavell R A. Mice deficient for the CD40 ligand. Immunity (1994); 1:423-431.

62 Grewal I S, Xu J, Flavell R A. Impairment of antigen-specific T-cell priming in mice lacking CD40 ligand. Nature (1995); 378:617-620.

63 Stout R D, Suttles J, Xu J, Grewal I S, Flavell R A. Impaired T cell-mediated macrophage activation in CD40 ligand-deficient mice. J Immunol (1996); 156:8-11.

64 Levy J, Espanol-Boren T, Thomas C, Fischer A, Tovo P, Bordigoni P, Resnick I, Fasth A, Baer M, Gomez L, Sanders E A, Tabone M D, Plantaz D, Etzioni A, Monafo V, Abinun M, Hammarstrom L, Abrabamsen T, Jones A, Finn A, Klemola T, DeVries E, Sanal O, Peitsch M C, Notarangelo L D. Clinical spectrum of X-linked hyper-IgM sysdrome. J Pediatr (1997); 131:47-54.

65 Soong L, Xu J C, Grewal I S, Kima P, Sun J, Longley B J Jr, Ruddle N H, McMahon-Pratt D, Flavell R A. Disruption of CD40-CD40 ligand interactions results in an enhanced susceptibility to *Leishmania amazonensis* infection. Immunity (1996); 4:263-273.

66 Campbell K A, Ovendale P J, Kennedy M K, Fanslow W C, Reed S G, Maliszewski C R. CD40 ligand is required for protective cell-mediated immunity to *Leishmania major*. Immunity (1996); 4:283-289.

67 Clegg C H, Rulffes J T, Haugen H S, Hoggatt I H, Aruffo A, Durham S K, Farr A G, Hollenbaugh D. Thymus dysfunction and chronic inflammatory disease in gp39 transgenic mice. Int Immunol (1997); 9:1111-1122.

68 Parker et al., Proc. Nat. Acad. Sci. USA (1995) 92:9560

69 Haanstra K G, Ringers J, Sick E A, Ramdien-Murli S, Kuhn E M, Boon L, Jonker M. Prevention of kidney allograft rejection using anti-CD40 and anti-CD86 in primates. Transplantation. (2003); 75(5):637-43.

70 Haanstra K G, Sick E A, Ringers J, Wubben J A M, Kuhn E M, Boon L, Jonker M. Costimulation blockade followed by a 12-week period of cyclosporine A facilitates prolonged drug-free survival of Rhesus Monkey kidney allografts. Transplantation. (2005); 79: 1623-1626.

71 Boon L, Brok H P, Bauer J, Ortiz-Buijsse A, Schellekens M M, Ramdien-Murli S et al. Prevention of experimental autoimmune encephalomyelitis in the common marmoset (*Callithrix jacchus*) using a chimeric antagonist monoclonal antibody against humanCD40 is associated with altered B cell responses. J Immunol (2001); 167:2942-2949.

72 Laman J D, 't Hart B A, Brok H, Meurs M, Schellekens M M, Kasran A et al. Protection of marmoset monkeys against EAE by treatment with a murine antibody blocking CD40 (mu5D12). Eur J Immunol (2002); 32:2218-2228.

73 Boon L, Laman J D, Ortiz-Buijsse A, den Hartog M T, Hoffenberg S, Liu P et al. Preclinical assessment of anti-CD40 Mab 5D12 in cynomolgus monkeys. Toxicology (2002); 174:53-65.

74 Kasran A, Boon L, Wortel C H, Hogezand R A, Schreiber S, Goldin E, Boer M, Geboes K, Rutgeerts P, Ceuppens J L. Safety and tolerability of antagonist anti-human CD40 Mab ch5D12 in patients with moderate to severe Crohn's disease. Aliment Pharmacol Ther. (2005); 22:111-22.

75 Haanstra K G, Sick E A, Ringers J, Wubben J A, Kuhn E M, Boon L, Jonker M. Costimulation blockade followed by a 12-week period of cyclosporine A facilitates prolonged drug-free survival of rhesus monkey kidney allografts. Transplantation. (2005); 79:1623-6.

76 't Hart B A, Blezer E L, Brok H P, Boon L, de Boer M, Bauer J, Laman J D. Treatment with chimeric anti-human CD40 antibody suppresses MRI-detectable inflammation and enlargement of pre-existing brain lesions in common marmosets affected by MOG-induced EAE. J Neuroimmunol. (2005); 163:31-9.

77 Koenen H J, den Hartog M T, Heerkens S, Fasse E, Ortiz-Buijsse A, van Neerven R J, Simons P J, Joosten I, Boon L. A novel bispecific antihuman CD40/CD86 fusion protein with t-cell tolerizing potential. Transplantation. (2004); 78:1429-38.

78 de Vos A F, Melief M J, van Riel D, Boon L, van Eijk M, de Boer M, Laman J D. Antagonist anti-human CD40 antibody inhibits germinal center formation in cynomolgus monkeys. Eur J. Immunol. (2004); 34:3446-55.

79 Laman J D, 't Hart B A, Brok H, Meurs M, Schellekens M M, Kasran A, Boon L, Bauer J, Boer M, Ceuppens J. Protection of marmoset monkeys against EAE by treatment with a murine antibody blocking CD40 (mu5D12). Eur J. Immunol. (2002); 32:2218-28.

80 Boon L, Laman J D, Ortiz-Buijsse A, den Hartog M T, Hoffenberg S, Liu P. Shiau F, de Boer M. Preclinical assessment of anti-CD40 Mab 5D12 in cynomolgus monkeys. Toxicology. (2002); 174:53-65.

81 Boon L, Brok H P, Bauer J, Ortiz-Buijsse A, Schellekens M M, Ramdien-Murli S, Blezer E, van Meurs M, Ceuppens J, de Boer M, 't Hart B A, Laman J D. Prevention of experimental autoimmune encephalomyelitis in the common marmoset (*Callithrix jacchus*) using a chimeric antagonist monoclonal antibody against human CD40 is associated with altered B cell responses. J. Immunol. (2001); 167:2942-9.

82 S. G. Antunes, N. G. de Groot, H. Brok, G. Doxiadis, A. A. Menezes, N. Otting and R. E. Bontrop, The common marmoset: a new world primate species with limited Mhc class II variability, Proc. Natl. Acad. Sci. U.S. A. (1998); 95: 11745-11750.

83 B. Becher, B. G. Durell, A. V. Miga, W. F. Hickey and R. J. Noelle, The clinical course of experimental autoimmune encephalomyelitis and inflammation is controlled by the expression of CD40 within the central nervous system, J. Exp. Med. (2001); 193: 967-974.

84 R. E. Bontrop, N. Otting, N. G. de Groot and G. G. Doxiadis, Major histocompatibility complex class II polymorphisms in primates, Immunol. Rev. (1999); 167: 339-350.

85 H. P. Brok, A. Uccelli, N. Kerlero De Rosbo, R. E. Bontrop, L. Roccatagliata, N. G. de Groot, E. Capello, J. D. Laman, K. Nicolay, G. L. Mancardi, A. Ben-Nun and B. A. 't Hart, Myelin/oligodendrocyte glycoprotein-induced autoimmune encephalomyelitis in common marmosets: the encephalitogenic T cell epitope pMOG24-36 is presented by a monomorphic MHC class II molecule, J. Immunol. (2000); 165: 1093-1101.

86 H. P. Brok, J. Bauer, M. Jonker, E. Blezer, S. Amor, R. E. Bontrop, J. D. Laman and B. A. 't Hart, Non-human primate models of multiple sclerosis, Immunol. Rev. (2001); 183: 173-185.

87 C. P. Genain and S. L. Hauser, Experimental allergic encephalomyelitis in the New World monkey *Callithrix jacchus*, Immunol. Rev. (2001); 183: 159-172.

88 K. Gerritse, J. D. Laman, R. J. Noelle, A. Aruffo, J. A. Ledbetter, W. J. Boersma and E. Claassen, CD40-CD40 ligand interactions in experimental allergic encephalomyelitis and multiple sclerosis, Proc. Natl. Acad. Sci. U.S. A. (1996); 93: 2499-2504.

89 A. M. Girvin, M. C. Dal Canto and S. D. Miller, CD40/CD40L interaction is essential for the induction of EAE in the absence of CD28-mediated co-stimulation, J. Autoimmun. (2002); 18:83-94.

90 I. S. Grewal and R. A. Flavell, A central role of CD40 ligand in the regulation of CD4+ T-cell responses, Immunol. Today (1996); 17:410-414.

91 L. M. Howard, A. J. Miga, C. L. Vanderlugt, M. C. Dal Canto, J. D. Laman, R. J. Noelle and S. D. Miller, Mechanisms of immunotherapeutic intervention by anti-CD40L (CD154) antibody in an animal model of multiple sclerosis, J. Clin. Invest. (1999); 103:281-290.

92 E. K. Jordan, H. I. McFarland, B. K. Lewis, N. Tresser, M. A. Gates, M. Johnson, M. Lenardo, L. A. Matis, H. F.

McFarland and J. A. Frank, Serial M R imaging of experimental autoimmune encephalomyelitis induced by human white matter or by chimeric myelin-basic and proteolipid protein in the common marmoset, AJNR Am. J. Neuroradiol. (1999); 20:965-976.

93 J. D. Laman, E. Claassen and R. J. Noelle, Functions of CD40 and its ligand, gp39 (CD40L), Crit. Rev. Immunol. (1996); 16:59-108.

94 J. D. Laman, C. B. Maassen, M. M. Schellekens, L. Visser, M. Kap, E. de Jong, M. van Puijenbroek, M. J. van Stipdonk, M. van Meurs, C. Schwarzler and U. Gunthert, Therapy with antibodies against CD40L (CD154) and CD44-variant isoforms reduces experimental autoimmune encephalomyelitis induced by a proteolipid protein peptide, Mult. Scler. (1998); 4: 147-153.

95 J. D. Laman, M. van Meurs, M. M. Schellekens, M. de Boer, B. Melchers, L. Massacesi, H. Lassmann, E. Claassen and B. A. 't Hart, Expression of accessory molecules and cytokines in acute EAE in marmoset monkeys (*Callithrix jacchus*), J. Neuroimmunol. (1998); 86:30-45.

96 J. Mestas and C. C. Hughes, Of mice and not men: differences between mouse and human immunology, J. Immunol. (2004); 172: 2731-2738.

97 S. A. Quezada, L. Z. Jarvinen, E. F. Lind and R. J. Noelle, CD40/CD154 interactions at the interface of tolerance and immunity, Annu. Rev. Immunol. (2004); 22:307-328.

98 C. S. Raine, B. Cannella, S. L. Hauser and C. P. Genain, Demyelination in primate autoimmune encephalomyelitis and acute multiple sclerosis lesions: a case for antigen-specific antibody mediation, Ann. Neurol. (1999); 46:144-160.

99 D. H. Sachs, Tolerance: of mice and men, J. Clin. Invest. (2003); 111:1819-1821.

100 E. B. Samoilova, J. L. Horton, H. Zhang and Y. Chen, CD40L blockade prevents autoimmune encephalomyelitis and hampers TH1 but not TH2 pathway of T cell differentiation, J. Mol. Med. (1997); 75: 603-608.

101 B. A. 't Hart, J. Bauer, H. J. Muller, B. Melchers, K. Nicolay, H. Brok, R. E. Bontrop, H. Lassmann and L. Massacesi, Histopathological characterization of magnetic resonance imaging-detectable brain white matter lesions in a primate model of multiple sclerosis: a correlative study in the experimental autoimmune encephalomyelitis model in common marmosets (*Callithrix jacchus*), Am. J. Pathol. (1998); 153:649-663.

102 B. A. 't Hart, M. van Meurs, H. P. Brok, L. Massacesi, J. Bauer, L. Boon, R. E. Bontrop and J. D. Laman, A new primate model for multiple sclerosis in the common marmoset, Immunol. Today (2000); 21:290-297.

103 B. 't Hart, S. Amor and M. Jonker, Evaluating the validity of animal models for research into therapies for immune-based disorders, Drug Discov. Today (2004); 9: 517-524.

104 't Hart et al., 2004b B. A. 't Hart, J. D. Laman, J. Bauer, E. D. Blezer, Y. van Kooyk and R. Q. Hintzen, Modelling of multiple sclerosis: lessons learned in a non-human primate, Lancet Neurol (2004); 3: 589-597.

105 B. A. 't Hart, J. Vogels, J. Bauer, H. P. Brok and E. Blezer, Non-invasive measurement of brain damage in a primate model of multiple sclerosis, Trends Mol. Med. (2004); 10: 85-91.

106 B. A. 't Hart, J. T. Vogelsj J. Bauer, H. P. M. Brok and E. Blezer, Non-invasive measurement of brain damage in a primate model of multiple sclerosis, Trends Mol. Med. (2004); 10: 85-91.

107 P. Villoslada, K. Abel, N. Heald, R. Goertsches, S. L. Hauser and C. P. Genain, Frequency, heterogeneity and encephalitogenicity of T cells specific for myelin oligodendrocyte glycoprotein in naive outbred primates, Eur. J. Immunol. (2001); 31: 2942-2950.

108 Bata-Csorgo Z, Hammerberg C, Voorhees J J, Cooper K D. Intralesional T-lymphocyte activation as a mediator of psoriatic epidermal hyperplasia. J Invest Dermatol (1995); 105(1 Suppl): 89S-94S.

109 Bos J D, De Rie M A. The pathogenesis of psoriasis: immunological facts and speculations. Immunol Today (1999); 20: 40-46.

110 Lebwohl M. Psoriasis. Lancet (2003); 361: 1197-1204.

111 van Kooten C, Banchereau J. CD40-CD40 ligand. J Leukoc Biol (2000); 67: 2-17.

112 Peguet-Navarro J, Dalbiez-Gauthier C, Moulon C, et al. CD40 ligation of human keratinocytes inhibits their proliferation and induces their differentiation. Immunol (1997); 158: 144-152.

113 Denfeld R W, Hollenbaugh D, Fehrenbach A, et al. CD40 is functionally expressed on human keratinocytes. Eur J Immunol (1996); 26: 2329-2334.

114 Gaspari A A, Sempowski G D, Chess P, Gish J, Phipps R P. Human epidermal keratinocytes are induced to secrete interleukin-6 and co-stimulate T lymphocyte proliferation by a CD40-dependent mechanism. Eur J Immunol (1996); 26: 1371-1377.

115 Pasch M C, Bos J D, Asghar S S. Activation of complement from psoriasis. Clin Exp Dermatol (1998); 23: 189-190.

116 Pasch M C, Timar, K, van Meus M, Heyendaal V M R, Bos J D, Laman J D, Ashgar S S. In situ demonstration of CD40- and CD154-positive cells in psoriatic lesions and keratinocyte production of chemokines by CD40 ligation in vitro. J. Pathol (2004); 203:839-848.

The invention claimed is:

1. A polypeptide comprising an amino acid sequence

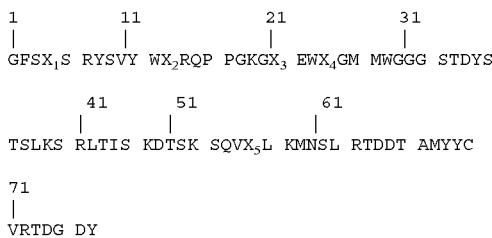

```
1           11          21          31
|           |           |           |
GFSX₁S RYSVY WX₂RQP PGKGX₃ EWX₄GM MWGGG STDYS 41          51          61
      |           |           |
TSLKS RLTIS KDTSK SQVX₅L KMNSL RTDDT AMYYC

71
|
VRTDG DY
``` wherein:
X₁ is G, A, V, L, I, P, F, M, W, C, N, Q, S, T, Y, D, E, K, R or H;
X₂ is G, A, V, L, I, P, F, M, W, C, N, Q, S, T, Y, D, E, K, R or H;
X₃ is G, A, V, L, I, P, F, M, W, C, N, Q, S, T, Y, D, E, K, R or H;
X₄ is G, A, V, L, I, P, F, M, W, C, N, Q, S, T, Y, D, E, K, R or H; and
X₅ is G, A, V, L, I, P, F, M, W, C, N, Q, S, T, Y, D, E, K, R or H
(SEQ ID NO: 1).

2. A polypeptide according to claim 1, wherein:
X₁ is G, A, V, L, P, F, M, W, C, N, Q, S, T, Y, D, E, K, R or H.

3. A polypeptide according to claim 1, wherein:
X₁ is G, A, V, L, P, F or M;
X₂ is G, A, V, L, I, P, F or M;
X₃ is G, A, V, L, I, P, F, M;
X₄ is G, A, V, L, I, P, F, M; and
X₅ is G, A, V, L, I, P, F, M, W, C, N, Q, S, T or Y.

4. A polypeptide according to claim 1, wherein:
X₁ is G, A, V, L or M;
X₂ is G, A, V, L, I or M;
X₃ is G, +A, V, L, I, P, F, M;
X₄ is G, A, V, L, I or M; and
X₅ is P, F, W, N, Q, S, T or Y.

5. A polypeptide according to claim 4, wherein:
X₁ is L;
X₂ is I;
X₃ is P;
X₄ is M; or X₅ is S.

6. A polypeptide according to claim 1, wherein:
X₁ is I and X₂ is V;
X₁ is L and X₂ is I;
X₁ is V and X₂ is V;
X₁ is L and X₂ is L; or
X₁ is L and X₂ is V.

7. A polypeptide according to claim 6, wherein
X₃ is P;
X₄ is M; and
X₅ is F or X₅ is S, preferably S.

8. A polypeptide according to claim 1, wherein:
X₁ is L; X₂ is V; X₃ is L; X₄ is L and X₅ is F.

9. A polypeptide comprising amino acid sequence

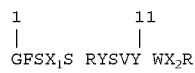

```
    1          11
    |          |
GFSX₁S RYSVY WX₂R
``` wherein:
X₁ is L and X₂ is I (SEQ ID NO: 3); or
X₁ is I and X₂ is V (SEQ ID NO: 4).

10. An anti-CD40 antibody comprising a polypeptide according to claim 1 or claim 8.

11. An anti-CD40 antibody according to claim 10, comprising a constant region of a human antibody, preferably an IgG constant region.

12. An anti-CD40 antibody according to claim 10, wherein said constant region is a region that is deficient in complement activation, preferably human IgG₄ constant region or a mutated human IgG₁ constant region.

13. An antagonistic anti-human CD40 monoclonal antibody comprising a polypeptide according to claim 1 or claim 8.

14. An antagonistic anti-human CD40 monoclonal antibody according to claim 13, wherein the antibody is deimmunized.

15. An antagonistic anti-human CD40 monoclonal antibody according to claim 13 comprising an amino acid sequence

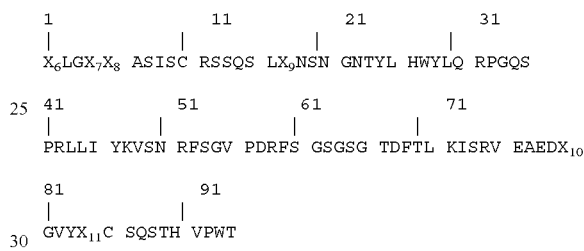

```
1              11          21          31
|              |           |           |
X₆LGX₇X₈ ASISC RSSQS LX₉NSN GNTYL HWYLQ RPGQS 41          51          61          71
|           |           |           |
PRLLI YKVSN RFSGV PDRFS GSGSG TDFTL KISRV EAEDX₁₀

81              91
|               |
GVYX₁₁C SQSTH VPWT
``` wherein:
X₆ is N, Q, S, T, Y, W or C;
X₇ is D, E, N, Q, S, T, Y, W or C;
X₈ is N, Q, S, T, Y, G, A, V, L, I, P, F, M, W or C;
X₉ is G, A, V, L, I, P, F, M;
X₁₀ is G, A, V, L, I, P, F, M; and
X₁₁ is N, Q, S, T, Y, G, A, V, L, I, P, F, M, W or C
(SEQ ID NO: 5).

16. An antagonistic anti-human CD40 monoclonal antibody according to claim 15 comprising an amino acid sequence

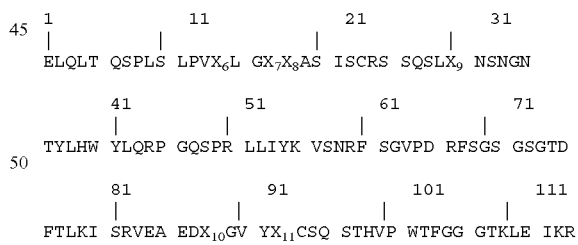

```
1              11          21          31
|              |           |           |
ELQLT QSPLS LPVX₆L GX₇X₈AS ISCRS SQSLX₉ NSNGN 41          51          61          71
      |           |           |           |
TYLHW YLQRP GQSPR LLIYK VSNRF SGVPD RFSGS GSGTD 81          91          101         111
      |           |           |           |
FTLKI SRVEA EDX₁₀GV YX₁₁CSQ STHVP WTFGG GTKLE IKR (SEQ ID NO: 6).
```

17. An antibody according to claim 15 or claim 16 wherein
X₆ is T or S, X₇ is D or Q, X₈ is Q or P, X₉ is V or A, X₁₀ is V or L and X₁₁ is F or Y.

18. An antibody according to claim 15 or claim 16, wherein:
X₆ is T, X₇ is Q, X₈ is P, X₉ is A, X₁₀ is V and X₁₁ is Y.

19. An antibody obtainable by a method for producing an antibody comprising culturing a cell comprising an antibody according to claim 15 or claim 16 and harvesting said antibody from said culture.

20. An antibody according to claim 19 that is purified.

21. A polypeptide comprising an amino acid sequence

```
 1          11          21          31
 |          |           |           |
QVKLQ ESGPG LVKPS ETLSI TCTVS GFSX1S RYSVY WX2RQP 41          51          61          71
 |          |           |           |
PGKGP EWX4GM MWGGG STDYS TSLKS RLTIS KDTSK 81          91          101         111
 |          |           |           |
SQVX5L KMNSL RTDDT AMYYC VRTDG DYWGQ GTTVT VSS.
``` wherein:
- $X_1$ is G, A, V, L, I, P, F, M, W, C, N, Q, S, T, Y, D, E, K, R or H;
- $X_2$ is G, A, V, L, I, P, F, M, W, C, N, Q, S, T, Y, D, E, K, R or H;
- $X_3$ is G, A, V, L, I, P, F, M, W, C, N, Q, S, T, Y, D, E, K, R or H;
- $X_4$ is G, A, V, L, I, P, F, M, W, C, N, Q, S, T, Y, D, E, K, R or H; and
- $X_5$ is G, A, V, L, I, P, F, M, W, C, N, Q, S, T, Y, D, E, K, R or H (SEQ ID NO. 2).

22. A polypeptide according to claim 21, wherein:
i. $X_1$ is G, A, V, L, P, F, M, W, C, N, Q, S, T, Y, D, E, K, R or H.

23. A polypeptide according to claim 21, wherein:
i. $X_1$ is G, A, V, L, P, F or M;
ii. $X_2$ is G, A, V, L, I, P, F or M;
iii. $X_3$ is G, A, V, L, I, P, F, M;
iv. $X_4$ is G, A, V, L, I, P, F, M; and
v. $X_5$ is G, A, V, L, I, P, F, M, W, C, N, Q, S, T or Y.

24. A polypeptide according to claim 21, wherein:
i. $X_1$ is G, A, V, L or M;
ii. $X_2$ is G, A, V, L, I or M;
iii. $X_3$ is G, A, V, L, I, P, F, M;
iv. $X_4$ is G, A, V, L, I or M; and
v. $X_5$ is P, F, W, N, Q, S, T or Y.

25. A polypeptide according to claim 24, wherein:
i. $X_1$ is L;
ii. $X_2$ is I;
iii. $X_3$ is P;
iv. $X_4$ is M; or $X_5$ is S.

26. A polypeptide according to claim 21, wherein:
i. $X_1$ is I and $X_2$ is V;
ii. $X_1$ is L and $X_2$ is I;
iii. $X_1$ is V and $X_2$ is V;
iv. $X_1$ is L and $X_2$ is L; or
v. $X_1$ is L and $X_2$ is V.

27. A polypeptide according to claim 26, wherein
i. $X_3$ is P;
ii. $X_4$ is M; and
iii. $X_5$ is F or $X_5$ is S, preferably S.

28. A polypeptide according to claim 21, wherein:
i. $X_1$ is L; $X_2$ is V; $X_3$ is L; $X_4$ is L and $X_5$ is F.

29. An anti-CD40 antibody comprising a polypeptide according to claim 21.

30. An anti-CD40 antibody according to claim 29, comprising a constant region of a human antibody, preferably an IgG constant region.

31. An anti-CD40 antibody according to claim 29, wherein said constant region is a region that is deficient in complement activation, preferably human $IgG_4$ constant region or a mutated human $IgG_1$ constant region.

32. An antagonistic anti-human CD40 monoclonal antibody comprising a polypeptide according to claim 21.

33. An antagonistic anti-human CD40 monoclonal antibody according to claim 32 further comprising an amino acid sequence

```
 1          11          21          31
 |          |           |           |
X6LGX7X8 ASISC RSSQS LX9NSN GNTYL HWYLQ RPGQS 41          51          61          71
 |          |           |           |
PRLLI YKVSN RFSGV PDRFS GSGSG TDFTL KISRV EAEDX10

81          91
 |          |
GVYX11C SQSTH VPWT
``` wherein:
- $X_6$ is N, Q, S, T, Y, W or C;
- $X_7$ is D, E, N, Q, S, T, Y, W or C;
- $X_8$ is N, Q, S, T, Y, G, A, V, L, I, P, F, M, W or C;
- $X_9$ is G, A, V, L, I, P, F, M;
- $X_{10}$ is G, A, V, L, I, P, F, M; and
- $X_{11}$ is N, Q, S, T, Y, G, A, V, L, I, P, F, M, W or C (SEQ ID NO: 5).

34. An antagonistic anti-human CD40 monoclonal antibody according to claim 32 further comprising an amino acid sequence

```
 1          11          21          31
 |          |           |           |
ELQLT QSPLS LPVX6L GX7X8AS ISCRS SQSLX9 NSNGN 41          51          61          71
 |          |           |           |
TYLHW YLQRP GQSPR LLIYK VSNRF SGVPD RFSGS GSGTD 81          91          101
 |          |           |
FTLKI SRVEA EDX10GV YX11CSQ STHVP WTFGG GTKLE

111
 |
IKR (SEQ ID NO: 6).
```

35. An antagonistic anti-human CD40 monoclonal antibody according to claim 33 or claim 34 wherein
$X_6$ is T or S, $X_7$ is D or Q, $X_8$ is Q or P, $X_9$ is V or A, $X_{10}$ is V or L and $X_{11}$ is F or Y.

36. An antagonistic anti-human CD40 monoclonal antibody according to claim 35, wherein:
$X_6$ is T, $X_7$ is Q, $X_8$ is P, $X_9$ is A, $X_{10}$ is V and $X_{11}$ is Y.

37. An antibody obtainable by culturing a cell comprising an antibody according to claim 33 or claim 34 and harvesting said antibody from said culture.

38. An antibody according to claim 37, wherein the antibody is purified.

* * * * *